US009668966B2

(12) United States Patent
Brooks et al.

(10) Patent No.: US 9,668,966 B2
(45) Date of Patent: *Jun. 6, 2017

(54) COSMETIC COMPOSITIONS COMPRISING MICROALGAL COMPONENTS

(71) Applicant: TerraVia Holdings, Inc., South San Francisco, CA (US)

(72) Inventors: Geoffrey Brooks, Reno, NV (US); Scott Franklin, Woodside, CA (US)

(73) Assignee: TerraVia Holdings, Inc., South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/931,517

(22) Filed: Nov. 3, 2015

(65) Prior Publication Data
US 2016/0120795 A1 May 5, 2016

Related U.S. Application Data

(63) Continuation of application No. 14/015,921, filed on Aug. 30, 2013, now Pat. No. 9,205,040, which is a continuation of application No. 13/128,217, filed as application No. PCT/US2009/063740 on Nov. 9, 2009, now Pat. No. 8,557,249.

(60) Provisional application No. 61/112,464, filed on Nov. 7, 2008.

(51) Int. Cl.
| A01N 65/00 | (2009.01) |
| A61K 36/02 | (2006.01) |
| A61K 8/99 | (2017.01) |
| A61K 8/92 | (2006.01) |
| A61K 8/97 | (2017.01) |
| A61Q 5/02 | (2006.01) |
| A61Q 19/00 | (2006.01) |
| A61Q 19/10 | (2006.01) |
| C12N 1/12 | (2006.01) |
| C12R 1/89 | (2006.01) |
| A61K 8/49 | (2006.01) |
| A61Q 5/12 | (2006.01) |
| A61Q 1/06 | (2006.01) |
| A61Q 15/00 | (2006.01) |

(52) U.S. Cl.
CPC ............... *A61K 8/99* (2013.01); *A61K 8/498* (2013.01); *A61K 8/922* (2013.01); *A61K 8/975* (2013.01); *A61Q 5/02* (2013.01); *A61Q 5/12* (2013.01); *A61Q 19/00* (2013.01); *A61Q 19/10* (2013.01); *C12N 1/12* (2013.01); *C12R 1/89* (2013.01); *A61K 2800/10* (2013.01); *A61K 2800/805* (2013.01); *A61Q 1/06* (2013.01); *A61Q 15/00* (2013.01)

(58) Field of Classification Search
None
See application file for complete search history.

(56) References Cited

U.S. PATENT DOCUMENTS

| 3,981,996 A | 9/1976 | Leigh |
| 3,983,008 A | 9/1976 | Shinozaki et al. |
| 4,373,434 A | 2/1983 | Alexander et al. |
| 4,417,415 A | 11/1983 | Cysewski et al. |
| 4,742,164 A | 5/1988 | Iguchi et al. |
| 4,901,635 A | 2/1990 | Williams |
| 4,906,746 A | 3/1990 | Barnier et al. |
| 5,089,481 A | 2/1992 | Muto et al. |
| 5,198,217 A | 3/1993 | Vedros |
| 5,338,673 A | 8/1994 | Thepenier et al. |
| 5,401,504 A | 3/1995 | Das et al. |
| 5,508,033 A | 4/1996 | Briand |
| 5,521,090 A | 5/1996 | Doncheck et al. |
| 5,643,585 A | 7/1997 | Arad et al. |
| 5,658,767 A | 8/1997 | Kyle |
| 5,680,812 A | 10/1997 | Linsgeseder |
| 5,685,218 A | 11/1997 | Kemper |
| 5,826,500 A | 10/1998 | Kemper |
| 5,878,747 A | 3/1999 | Enomoto et al. |
| 5,916,577 A | 6/1999 | Golz et al. |
| 6,166,231 A | 12/2000 | Hoeksema |
| 6,328,987 B1 | 12/2001 | Marini |
| 6,440,431 B1 | 8/2002 | Yoshida et al. |
| 6,551,596 B2 | 4/2003 | Kralovec |
| 6,680,062 B2 | 1/2004 | Muizzuddin et al. |
| 6,750,048 B2 | 6/2004 | Ruecker et al. |
| 6,767,899 B1 | 7/2004 | Kay et al. |
| 7,025,966 B2 | 4/2006 | Majmudar |
| 7,037,697 B2 | 5/2006 | Kumar et al. |
| 7,063,957 B2 | 6/2006 | Chen |

(Continued)

FOREIGN PATENT DOCUMENTS

| EP | 0996740 B1 | 9/2005 |
| EP | 2260829 A2 | 12/2010 |

(Continued)

OTHER PUBLICATIONS

U.S. Appl. No. 60/816,967, filed Jun. 28, 2006, Expired.
Database GNPD [Online] Mintel: Accession No. 2281904, "Day Protective Lotion SPF 15 PA++," Nu Skin Daily Health Care Product, Jan. 1, 2014.
Database GNPD [Online] Mintel: Accession No. 2341052, "Skin Best CC Cream SPF 25," Biotherm, Apr. 1, 2014.
Database GNPD [Online] Mintel: Accession No. 2425307, "Ampleur Luxury White W Protect UV SPF 50+/PA+++," Highside, May 1, 2014.
Dvir et al., "Soluble polysaccharide and biomass of red microalgal *Porphyridium* sp. alter intestinal morphology and reduce serum cholesterol in rats", *British J Nutrition* 84(4):469-476, (2000).
El-Sheekh et al., "Variation of Some Nutritional Constituents and Fatty Acid Profiles of Chlorella vulgaris Beijerinck Grown under Auto and Heterotrophic Conditions," International Journal of Botany, 5(2):153-159, (2009).

(Continued)

*Primary Examiner* — Kade Ariani
(74) *Attorney, Agent, or Firm* — Weaver Austin Villeneuve & Sampson, LLC.

(57) ABSTRACT

The invention provides cosmetic compositions comprising microalgal biomass, whole microalgal cells, and/or microalgal oil in combination with one or more other cosmetic ingredients, and methods of making such compositions. In preferred embodiments, the microalgal components of the cosmetic compositions are derived from microalgal cultures grown heterotrophically and which comprise at least 10% oil by dry weight.

18 Claims, 1 Drawing Sheet

(56) References Cited

U.S. PATENT DOCUMENTS

| | | |
|---|---|---|
| 7,135,290 B2 | 11/2006 | Dillon |
| 7,303,753 B2 | 12/2007 | Majmudar |
| 7,351,558 B2 | 4/2008 | Ruecker et al. |
| 7,662,598 B2 | 2/2010 | Ruecker et al. |
| 7,678,931 B2 | 3/2010 | Fichtali et al. |
| 7,781,193 B2 | 8/2010 | Ruecker et al. |
| 8,277,849 B2 | 10/2012 | Dillon et al. |
| 8,298,548 B2 | 10/2012 | Avila et al. |
| 8,557,249 B2 | 10/2013 | Brooks et al. |
| 8,927,522 B2 | 1/2015 | Coragliotti et al. |
| 8,932,652 B2 | 1/2015 | Dillon et al. |
| 9,095,733 B2 | 8/2015 | Avila et al. |
| 9,205,040 B2 | 12/2015 | Brooks et al. |
| 9,597,280 B2 | 3/2017 | Yaiser |
| 2001/0055627 A1 | 12/2001 | Guthrie et al. |
| 2002/0031524 A1 | 3/2002 | Kralovec |
| 2003/0064494 A1 | 4/2003 | Kumar et al. |
| 2003/0078233 A1 | 4/2003 | Arad et al. |
| 2003/0134803 A1 | 7/2003 | Cherr et al. |
| 2003/0198730 A1 | 10/2003 | Stewart |
| 2003/0207947 A1 | 11/2003 | Desouza et al. |
| 2004/0168648 A1 | 9/2004 | Ayers |
| 2004/0180126 A1 | 9/2004 | Kies |
| 2004/0185063 A1 | 9/2004 | Ray |
| 2004/0197790 A1 | 10/2004 | Stanton et al. |
| 2004/0228875 A1 | 11/2004 | Leclerc et al. |
| 2005/0042355 A1 | 2/2005 | Perlman et al. |
| 2005/0089501 A1 | 4/2005 | Berardesca et al. |
| 2005/0106657 A1 | 5/2005 | Rodriguez et al. |
| 2005/0123499 A1 | 6/2005 | Majmudar |
| 2005/0129831 A1 | 6/2005 | Fabritius |
| 2005/0171053 A1 | 8/2005 | Blakemore et al. |
| 2005/0239742 A1 | 10/2005 | Place et al. |
| 2005/0261240 A1 | 11/2005 | Maguire et al. |
| 2006/0122410 A1 | 6/2006 | Fichtali et al. |
| 2006/0183184 A1 | 8/2006 | Bosley et al. |
| 2006/0210523 A1 | 9/2006 | Majmudar |
| 2006/0233845 A1 | 10/2006 | Lukowski et al. |
| 2006/0286205 A1 | 12/2006 | Fichtali et al. |
| 2007/0166266 A1 | 7/2007 | Dillon et al. |
| 2007/0166449 A1 | 7/2007 | Dillon et al. |
| 2007/0166797 A1 | 7/2007 | Dillon et al. |
| 2007/0167396 A1 | 7/2007 | Dillon et al. |
| 2007/0167397 A1 | 7/2007 | Dillon et al. |
| 2007/0167398 A1 | 7/2007 | Dillon et al. |
| 2007/0191303 A1 | 8/2007 | Dillon et al. |
| 2007/0297996 A1 | 12/2007 | Tanner |
| 2008/0124286 A1 | 5/2008 | Lisson |
| 2008/0206274 A1 | 8/2008 | Majmudar et al. |
| 2008/0299147 A1 | 12/2008 | Dillon et al. |
| 2009/0004715 A1 | 1/2009 | Trimbur et al. |
| 2009/0017058 A1 | 1/2009 | Arad et al. |
| 2009/0069213 A1 | 3/2009 | Avila et al. |
| 2009/0274736 A1 | 11/2009 | Dillon et al. |
| 2009/0285850 A1 | 11/2009 | Dillon et al. |
| 2009/0305942 A1 | 12/2009 | Day et al. |
| 2010/0170144 A1 | 7/2010 | Day et al. |
| 2010/0186117 A1 | 7/2010 | Fabijanski et al. |
| 2011/0124544 A1 | 5/2011 | He et al. |
| 2011/0250178 A1 | 10/2011 | Brooks et al. |
| 2012/0149075 A1 | 6/2012 | Day et al. |
| 2012/0202768 A1 | 8/2012 | Coragliotti et al. |
| 2012/0264177 A1 | 10/2012 | Avila et al. |
| 2013/0004554 A1 | 1/2013 | Dillon et al. |
| 2014/0170184 A1 | 6/2014 | Brooks et al. |
| 2015/0140051 A1 | 5/2015 | Dillon et al. |
| 2015/0150776 A1 | 6/2015 | Coragliotti et al. |
| 2015/0352034 A1 | 12/2015 | Schiff-Deb et al. |
| 2015/0366791 A1 | 12/2015 | Avila et al. |
| 2016/0058694 A1 | 3/2016 | Yaiser |

FOREIGN PATENT DOCUMENTS

| | | |
|---|---|---|
| FR | 2948877 | 2/2011 |
| IN | IT2007MI2063 | 2/2008 |
| IT | 2007MI2063 | 3/2017 |
| JP | 63096107 A | 4/1988 |
| JP | H04108374 | 4/1992 |
| JP | 04-222593 A | 8/1992 |
| JP | 2002069443 A | 3/2002 |
| WO | WO 94/10131 A1 | 5/1994 |
| WO | WO 97/00689 A1 | 1/1997 |
| WO | WO 00/75282 A1 | 12/2000 |
| WO | WO 01/81603 A2 | 11/2001 |
| WO | WO 02/11746 A2 | 2/2002 |
| WO | WO 03/041679 A2 | 5/2003 |
| WO | WO 03/072775 A1 | 9/2003 |
| WO | WO 2004/108941 A1 | 12/2004 |
| WO | WO 2007/066340 A1 | 6/2007 |
| WO | WO 2007/084769 A2 | 7/2007 |
| WO | WO 2007/136428 A2 | 11/2007 |
| WO | WO 2009/126843 A2 | 10/2009 |
| WO | WO 2010/054322 A1 | 5/2010 |
| WO | WO 2010/111710 A1 | 9/2010 |
| WO | WO 2013/036726 A1 | 9/2012 |
| WO | WO2013/036726 | 3/2013 |
| WO | WO 2013/158938 A1 | 10/2013 |
| WO | WO 2014/186395 A1 | 11/2014 |
| WO | WO 2015/191449 A2 | 12/2015 |

OTHER PUBLICATIONS

U.S. Appl. No. 60/832,091, filed Jul. 20, 2006, Expired.
U.S. Appl. No. 60/838,452, filed Aug. 17, 2006, Expired.
U.S. Appl. No. 60/872,072, filed Nov. 30, 2006, Expired.
U.S. Appl. No. 60/961,173, filed Jul. 18, 2007, Expired.
U.S. Appl. No. 61/112,464, filed Nov. 7, 2008, Expired.
U.S. Appl. No. 61/164,312, filed Mar. 27, 2009, Expired.
U.S. Appl. No. 61/823,771, filed May 15, 2013, Expired.
U.S. Appl. No. 62/009,296, filed Jun. 8, 2014, Expired.
U.S. Appl. No. 62/082,026, filed Nov. 19, 2014, Expired.
U.S. Appl. No. 14/888,695, filed Nov. 2, 2015, Pending.
"Buffer solution," *Wikipedia, the free encyclopedia*, 1-6, (2011). [Retrieved from the Internet May 11, 2011: <http://en.wikipedia.org/wiki/Buffer_solution>].
"Guidance for Industry: Container Closure Systems for Packaging Human Drugs and Biologics", U.S. Department of Health and Human Services, Food and Drug Administration, 1-35, (1999).
"All Natural Food Mask," The Raw Food Institute, 2 pages, (2013). [Retrieved from the Internet May 20, 2013: <URL: http://therawfoodinistitute.com/raw-food-articles/all-natural-food-mask/>].
Alignments, Sequence Search report, GenBank ACQ5U8S3_9RHOD Dec. 7, 2004.
Allen et al., "Carotenoid Distribution in Certain Naturally Occurring Algae and in some Artificially Induced Mutants of Chlorella pyrenoidosa," *J. gen. Microbial.*, (23)98-108, (1960).
Ansel et al., *Pharmaceutical Dosage Forms and Drug Delivery Systems*, published by Lippincott Williams & Wilkins, p. 55-56 (1999).
Arad et al., "Effects of Nitrogen on Polysaccharide Production in a Porphyridium," *Applied and Environmental Microbiology*, 54(10):2411-2414 (1988).
Baumann, "How to Prevent Photoaging?," *Journal of Investigative Dermatology*, 125:xii-xiii, (2005).
Becker, "Microalgae in Human and Animal Nutrition," *Handbook of Microalgal Culture*, Blackwell, P312-351, (2004).
Césarini et al., "Immediate Effects of UV Radiation on the Skin: Modification by an Antioxidant Complex Containing Carotenoids", *Photoderm., Photoimmun. & Photomed*. 19:182-189 (2003).
Conti et al., "Seasonal influences on stratum corneum ceramide 1 fatty acids and the influence of topical essential fatty acids," *International Journal of Cosmetics Science*, 18:1-12, (1996).
Dallimore, "Perfumery," *Chemistry and Technology of the Cosmetics and Toiletries Industry*, edited by D.F. Williams and W.H. Schmitt, published by Chapman & Hall, 258-259, (1992).
Database GNPD [Online] Mintel: Accession No. 2134486, "Facialist AC4 Serum," C'bon Cosmetics, Aug. 1, 2013.

(56) References Cited

OTHER PUBLICATIONS

EPO Application No. EP 10756997.2, Supplementary European Search Report and European Search Opinion, mailed Jul. 23, 2014.
EPO Supplementary European Search Report and European Search Opinion for application EP07718342 mailed Nov. 7, 2012.
Eteshola et al., "Red microalga exopolysaccharides: 2. Study of rheology, morphology and thermal gelation of aqueous preparations," *Acta Polym.*, 49:549-556, (1998).
Evans et al., "A statistical analysis of hair breakage. II. Repeated grooming experiments," J. Cosmet. Sci., 61:439-455, (2010).
Fabregas et al., "In vitro inhibition of the replication of haemorrhagic septicaemia virus (VHSV) and African swine fever virus (ASFV) by extracts from marine microalgae," Antiviral Research, 44:67-73, (1999).
Ficner et al, "Isolation, Crystallization, Crystal Structure Analysis and refinement of B-Phycoerythin from the Red Alga Pophyridium sordidum at 2.2 A Resolution", *J. Mol. Biol.* 228(3):935-950, (1992).
Gennaro, *Remington: The Science and Practice of Pharmacy* Lippincott Williams & Wilkins, 20th edition, p. 1017-1020 and 1694-1699. (2000).
Geresh, et al., "Characterization of the extracellular polysaccharide of *Porphyridium* sp. molecular weight determination and rheological properties", *Carbohydrate Polymers* 50:183-189, (2002).
Geresh, et al., "The extracellular polysaccharide of the Red Microalgae: Chemistry and Rheology", *Bioresource Technology* 38(2-3):195-201, (1991).
Gloaguen et al., "The extracellular polysaccharide of *Porphyridium* sp.: an NMR study of lithium-resistant oligosaccharidic fragments," *Carbohydrate Research*, 339:97-103, (2004).
Gourdon, D. et al. Lubrication by the red microalgae *Porphyridium* sp. polysaccharide: American Physical Society, March Meeting, Mar. 22-26, 2004, Palais des Congres de Montreal, Montreal, Quebec, Canada, Meeting ID: Mar. 4, abstract #H8.009—English Abs.
Gourdon, D. et al. "Superlubricity of a natural polysaccharide from the alga *Porphyridium* sp.," *American Physical Society, APS March Meeting*, Mar. 21-25, 2005 abstract #V31.010—English Abstract only.
Greul et al., "Photoprotection of UV-Irradiated Human Skin: An Antioxidative Combination of Vitamins E and C, Carotenoids, Selenium and Proanthocyanidins," *Skin Pharmacology and Applied Skin Physiology*, 15:307-315, (2002).
Guerin et al., "Haematococcus astaxanthin: applications for human health and nutrition," *TRENDS in Biotechnology*, 21(5):210-216, (2003).
Guil-Guerrero et al., "Functional properties of the biomass of three microalgal species", *J. Food Engin.* 65:511-517, (2004).
Guzman et al., "Anti-inflammatory and Immunomodulatory Activities of Polysaccharide from Chlorella stigmatophora and Phaeodactylum tricornutum", *Phytother. Res.* 17:665-670, (2003).
Holzer, "Water, pH and buffers," *Georgia Tech Prism Web Pages*, 1-6, (2002). [Retrieved from the Internet Jan. 2011: <http ://www.prism.gatech.edu/-gh19/b1510/water.htm>].
Huheihel, M. et al. "Activity of *Porphyridium* sp. polysaccharide against herpes simplex viruses in vitro and in vivo" *J. Biochem. Biophys. Methods* Jan. 4, 2002;50(2-3):189-200.
International Preliminary Report on Patentability for PCT/US2007/001653 mailed Sep. 9, 2008.
International Preliminary Report on Patentability for PCT/US2007/001319 mailed Oct. 21, 2008.
International Preliminary Report on Patentability for PCT/US2010/029081 mailed Sep. 27, 2011.
International Search Report and Written Opinion for PCT/US2007/001319 mailed Sep. 19, 2008.
International Search Report and Written Opinion for PCT/US2007/001653 mailed Jul. 28, 2008.
International Search Report or PCT/US2010/029081 mailed May 27, 2010.
Kamiya, "Effects of Blue Light and Ammonia on Nitrogen Metabolism in a Colorless Mutant of Chlorella," Plant Celll Physiol., 30(4):513-521, (1989).
Kruckeberg et al., "The HXT2 gene of Saccharomyces cerevisiae is required for high-affinity glucose transport", *Mol. Cell. Biol.* 10(11):5903-5913, (1990).
Lapidot, M. et al. "Stable Chloroplast Transformation of the Unicellular Red Alga Porphyridium Species", *Plant Physiol.* May 2002;129(1):7-12.
Lee et al., "Dietary Lutein Reduces Ultraviolet Radiation-Induced Inflammation and Immunosuppression", *J. Invest. Dermatol.* 122:510-517, (2004).
Leffingwell et al., "Cooling Ingredients and Their Mechanism of Action," *Handbook of Cosmetic Science and Technology*, 3rd ed., Informa Healthcare, pp. 661-675, (2009).
Liang et al., "Current microalgal health food R&D activities in China", *Hydrobiologia* 512:45-48, (2004).
Matsui et al., "Sulfated polysaccharides from Red Microalgae Have Antiinflammatory Properties In Vitro and In Vivo," *Applied Biochemistry and Biotechnology*, 104:13-22, (2003).
Merchuk et al. "Light/Dark Cycles in the Growth of the Red Microalga *Porphyridium* Sp.". *Biotechnol Bioeng.* Sep. 20, 1998;59(6):705-13.
Mitsuhashi et al., "X-Ray Structure of Beta-Carbonic Anhydrase from the Red Alga, Porphyridium purpureum, Reveals a Novel Catalytic Site for CO2 Hydration", *J. Biol. Chem.* 275(8):5521-5526, (2000).
Miyachi, *World Catalogue of Algae*, 2nd Edition. Edited by Shigetoh, Miyachi, published by the Japan Scientific Societies Press, p. 58-74 (1989).
Muggli, "Systemic evening primrose oil improves the biophysical skin parameters of healthy adults", *Intl. J. Cosmetic Sci.* 27:243-249, (2005).
NCB' submission L43357, "Chlorella vulgaris chloroplast large subunit ribosomal RNA (rrnL) gene," [online], (2005). [Retrieved from the internet May 14, 2010: <URL: http://www.ncbi.nlm.nih.gov/nuccore/17028301>].
Nghiem, et al., "Ultraviolet A Radiation Suppresses an Established Immune Response: Implications for Sunscreen Design", *J. Invest. Derm.* 117(5):1193-1198 (2001).
Olaitan et al., "Polysaccharides of Chlorella pyrenoidosa," *Biochem. J.*, 82:509-519, (1962).
PCT International Preliminary Report on Patentability (Chapter I) of May 10, 2011 for application PCT/US09/63740.
PCT International Search Report and Written Opinion of the International Searching Authority for application PCT/US2014/037898 mailed Oct. 23, 2014.
PCT International Search Report and Written Opinion of the International Searching Authority for application PCT/US2015/034671 mailed Dec. 16, 2015.
PCT Invitation to Pay Additional Fees for Application No. PCT/US2015/034671 mailed Sep. 7, 2015.
PCT Search Report of Mar. 2, 2010 for application PCT/US09/63740.
Petit et al., "Ultrasonic depolymerization of an exopolysaccharide produced by a bacterium isolated from a deep-sea hydrothermal vent polychaete annelid," Ultrasonics Sonochemistry, 14(2):107-112, (2007).
Primavera et al., "Clinical and instrumental evaluation of a food supplement in improving skin hydration", *Intl. J. Cosmetic Science* 27:199-204, (2005).
Pulz et al., "Valuable products from biotechnology of microalgae," *Appl Microbiol Biotechnol*, 65:635-648, (2004).
Rudnic et al., "Oral Solid Dosage Forms" in *Remington's Pharmaceutical Sciences*, 18th Edition, editor Alfonso R. Gennaro, published by Mack Publishing Company, p. 1633-1638 (1990).
Sansawa et al., "Production of Intracellular Phytochemicals in Chlorella under Heterotrophic Conditions," *J Biosci. Bioeng.*, 98(6):437-444, (2004).
Scipio, "A Red Marine Algae Sex Gel" website: http://www.antiviralgel.com/, download date Aug. 8, 2008.

(56) References Cited

OTHER PUBLICATIONS

Seffernick et al., "Melamine deaminase and atrazine chlorohydrolase: 98 percent identical but functionally different", *J. Bacteriology* 183(8):2405-2410, (2001).
Shrestha et al., "A glycoprotein noncovalently associated with cell-wall polysaccharide of the red microalga *Porphyridium* sp.(Rhodophyta)", *J. Phycol.* 40:568-580, (2004).
Sibbald et al., "Preparing the Wound Bed 2003: Focus on Infectin and Inflammation," *Ostomy/Wound Management.*, 49(11):24-51, (2003).
Simon-Bercovitch, et al., "Cell wall formation during the cell cycle of *Porphyridium* sp. (Phodophyta)", *J. Phycol.* 35:78-83, (1999).
Storey et al., "Eicosapentaenoic Acid and Docosahexaenoic Acid Reduce UVB- and TNF-α-induced IL-8 Secretion in Keratinocytes and UVB-induced IL-8 in Fibroblasts", *J. Invest. Dermatol.* 124:248-255, (2005).
Talyshinsky et al., "Anti-viral activity of red microalgal polysaccharides against retroviruses", *Cancer Cell Int'l.* 2(8):1-7 (2002).
Tannin-Spitz et al, "Antioxidant activity of the polysaccharide of the red microalga *Porphyridium* sp," *Journal of Applied Mycology*, 17(3):215-22, (2005).
U.S. Appl No. 11/336,426, Examiner Interview Summary Record and Restriction Requirement mailed Nov. 3, 2008.
U.S. Appl. No. 11/336,426, Examiner Interview Summary Record and Advisory Action mailed Sep. 9, 2009.
U.S. Appl. No. 11/336,426, Examiner Interview Summary Record and Advisory Action mailed Oct. 14, 2009.
U.S. Appl. No. 11/336,426, Examiner Interview Summary Record mailed Jun. 29, 2010.
U.S. Appl. No. 11/336,426, Examiner Interview Summary Record and Abandonment Notice mailed Apr. 12, 2011.
U.S. Appl. No. 11/336,426, Final Office Action mailed Jun. 22, 2009.
U.S. Appl. No. 11/336,426, Non-Final Office Action mailed Feb. 26, 2010.
U.S. Appl. No. 11/336,426, Non-Final Office Action mailed Aug. 3, 2010.
U.S. Appl. No. 11/336,426, Restriction Requirement mailed Apr. 4, 2008.
U.S. Appl. No. 11/336,428, Examiner Interview Summary Record and Abandonment Notice mailed Mar. 23, 2009.
U.S. Appl. No. 11/336,428, Non-Final Office Action mailed Jul. 9, 2008.
U.S. Appl. No. 11/336,428, Restriction Requirement mailed Apr. 14, 2008.
U.S. Appl. No. 11/336,430, Examiner Interview Summary Record and Abandonment Notice mailed Aug. 4, 2009.
U.S. Appl. No. 11/336,430, Restriction Requirement mailed Apr. 25, 2008.
U.S. Appl. No. 11/336,430, Restriction Requirement mailed Sep. 26, 2008.
U.S. Appl. No. 11/336,431, Non-Final Office Action mailed Nov. 2, 2007.
U.S. Appl. No. 11/336,431, Restriction Requirement mailed Mar. 30, 2007.
U.S. Appl. No. 11/336,431, Restriction Requirement mailed Dec. 18, 2006.
U.S. Appl. No. 11/336,656, Non-Final Office Action mailed Aug. 26, 2008.
U.S. Appl. No. 11/336,656, Restriction Requirement mailed Mar. 4, 2008.
U.S. Appl. No. 11/337,103, Advisory Action mailed Feb. 18, 2010.
U.S. Appl. No. 11/337,103, Advisory Action mailed Apr. 6, 2010.
U.S. Appl. No. 11/337,103, Advisory Action mailed Dec. 18, 2009.
U.S. Appl. No. 11/337,103, Examiner Interview Summary Record and Abandonment Notice mailed Apr. 26, 2011.
U.S. Appl. No. 11/337,103, Final Office Action mailed Aug. 4, 2009.
U.S. Appl. No. 11/337,103, Non-Final Office Action mailed Aug. 13, 2010.
U.S. Appl. No. 11/337,103, Non-Final Office Action mailed Nov. 7, 2008.
U.S. Appl. No. 11/337,103, Restriction Requirement mailed Mar. 18, 2008.
U.S. Appl. No. 11/337,171, Examiner Interview Summary Record and Abandonment Notice mailed Apr. 29, 2009.
U.S. Appl. No. 11/337,171, Non-Final Office Action mailed Aug. 13, 2008.
U.S. Appl. No. 11/337,171, Restriction Requirement mailed Mar. 5, 2008.
U.S. Appl. No. 11/932,754, Examiner Interview Summary Record mailed Oct. 5, 2010.
U.S. Appl. No. 11/932,754, Final Office Action mailed Aug. 9, 2011.
U.S. Appl. No. 11/932,754, Non-Final Office Action mailed Dec. 23, 2010.
U.S. Appl. No. 11/932,754, Restriction Requirement mailed Aug. 3, 2010.
U.S. Appl. No. 11/932,782, Advisory Action mailed Sep. 16, 2010.
U.S. Appl. No. 11/932,782, Election of Species Requirement mailed Aug. 16, 2011.
U.S. Appl. No. 11/932,782, Final Office Action mailed May 20, 2010.
U.S. Appl. No. 11/932,782, Non-Final Office Action mailed Jan. 12, 2011.
U.S. Appl. No. 11/932,782, Non-Final Office Action mailed Jan. 24, 2011.
U.S. Appl. No. 11/932,782, Non-Final Office Action mailed Mar. 20, 2012.
U.S. Appl. No. 11/932,782, Non-Final Office Action mailed Nov. 19, 2009.
U.S. Appl. No. 11/932,782, Notice of Allowance mailed Jul. 18, 2012.
U.S. Appl. No. 11/932,782, Restriction Requirement mailed Jun. 26, 2009.
U.S. Appl. No. 12/176,320, Final Office Action mailed Sep. 22, 2011.
U.S. Appl. No. 12/176,320, Non-Final Office Action mailed Mar. 15, 2011.
U.S. Appl. No. 12/176,320, Non-Final Office Action mailed Dec. 14, 2011.
U.S. Appl. No. 12/176,320, Notice of Allowance mailed Sep. 4, 2012.
U.S. Appl. No. 12/176,320, Restriction Requirement mailed Nov. 29, 2010.
U.S. Appl. No. 12/430,036, Final Office Action mailed Aug. 2, 2011.
U.S. Appl. No. 12/430,036, Non-Final Office Action mailed Dec. 14, 2010.
U.S. Appl. No. 13/128,217, Non-Final Office Action mailed Mar. 29, 2013.
U.S. Appl. No. 13/128,217, Notice of Allowance mailed Aug. 7, 2013.
U.S. Appl. No. 13/260,546, Final Office Action mailed Jan. 30, 2014.
U.S. Appl. No. 13/260,546, Non-Final Office Action mailed Jul. 1, 2013.
U.S. Appl. No. 13/260,546, Notice of Allowance mailed Aug. 29, 2014.
U.S. Appl. No. 13/260,546, Requirement for Restriction/Election mailed Feb. 19, 2013.
U.S. Appl. No. 13/531,419, Final Office Action mailed Jan. 23, 2013.
U.S. Appl. No. 13/531,419, Non-Final Office Action mailed Jun. 22, 2012.
U.S. Appl. No. 13/531,419, Non-Final Office Action mailed Sep. 9, 2014.
U.S. Appl. No. 13/531,419, Notice of Allowance mailed Mar. 26, 2015.
U.S. Appl. No. 13/600,102, Non-Final Office Action mailed May 13, 2014.
U.S. Appl. No. 13/600,102, Non-Final Office Action mailed Dec. 10, 2013.
U.S. Appl. No. 13/600,102, Notice of Allowance mailed Oct. 22, 2014.

(56) References Cited

OTHER PUBLICATIONS

U.S. Appl. No. 13/600,102, Restriction Requirement mailed Sep. 26, 2013.
U.S. Appl. No. 14/015,921, Final Office Action mailed May 11, 2015.
U.S. Appl. No. 14/015,921, Non-Final Office Action mailed Dec. 10, 2014.
U.S. Appl. No. 14/015,921, Notice of Allowance mailed Aug. 31, 2015.
U.S. Appl. No. 14/015,921, Restriction Requirement mailed May 15, 2014.
Ucko et al., "Relationship between the Unicellular Red Alga *Porphyridium* sp. and Its Predator, the Dinoflagellate *Gymnodinium* sp.," *Applied and Environmental Microbiology*, Nov. 1989, 55(11):2990-2994.
Urano, et al., "Effect of Osmotic Stabilizers on Protoplast Generation of Chlorella ellipsoidea Yellow/White Color Mutants," Journal of Bioscience and Bioengineering, 90(5):567-569, (2000).
Van Der Meeren et al., "Abdominal Radiation Exposure Elicits Inflammatory Responses and Abscopal Effects in the Lungs of Mice", *Radiation Res.* 163:144-152, (2005).
Vinson et al., "Comparative topical absorption and antioxidant effectiveness of two forms of coenzyme Q10 after a single dose and after long-term supplementation in the skin of young and middle-aged subjects", *IFSCC Magazine* 8(4):1-6, (2005).
Wells, "Additivity of mutational effects in proteins", *Biochem.* 29(37):8509-8517, (1990).
Xu et al., "High quality biodiesel production from a microalga *Chlorella protothecoides* by heterotrophic growth in fennenters,"*Journal of Biotechnology*, 126:499-507. (2006).
Yamamoto et al., "Late type of daughter cell wall synthesis in one of the Chlorellaceae, *Parachlorella kessleri* (Chlorophyta, Trebouxiophyceae)," *Planta*, 221:766-775, (2005).
U.S. Appl. No. 60/816,967, filed Jun. 28, 2006, Dillon et al.
U.S. Appl. No. 60/832,091, filed Jul. 20, 2006, Dillon et al.
U.S. Appl. No. 60/838,452, filed Aug. 17, 2006, Dillon et al.
U.S. Appl. No. 60/872,072, filed Nov. 30, 2006, Dillon et al.
U.S. Appl. No. 11/932,754, filed Oct. 31, 2007, Dillon et al.
U.S. Appl. No. 12/430,036, filed Apr. 24, 2009, Dillon et al.
Andersen, "Biology and Systematics of Heterokont and Haptophyte Algae," American Journal of Botany, 91(10):1508-1522, (2004).
Deng et al., "Culture observation and molecular phylogenetic analysis on the blooming green alga *Chaetomorpha valida* (Cladophorales, Chlorophyta) from China," *Chinese Journal of Oceanology and Limnology*, 31(3)552-559, (2013). Abstract only. [Retrieved from the Internet Jul. 10, 2013: <URL: http://link.springer.com/article/10.1007/s00343-013-2216-x>].
PCT International Preliminary Report on Patentability for the International Searching Authority for application PCT/US2015/034671 mailed Dec. 16, 2015.
U.S. Appl. No. 14/553,138, Restriction Requirement mailed Apr. 26, 2016.
U.S. Appl. No. 14/553,138, Non-Final Office Action mailed Sep. 30, 2016.
U.S. Appl. No. 14/563,486, Restriction Requirement mailed Sep. 15, 2016.
U.S. Appl. No. 14/751,527, Non-Final Office Action mailed Jul. 25, 2016.
U.S. Appl. No. 14/888,695, Restriction Requirement mailed Mar. 29, 2016.
U.S. Appl. No. 14/888,695, Non-Final Office Action mailed Jun. 23, 2016.
Barton et al., "Chapter 27: Pylogenetic Reconstruction," Evolution, Online Chapter, Cold Spring Harbor Laboratory Press, pp. 1-55, (2007). [Retrieved from the Internet Jul. 10, 2013: <URL: http://evolution-textbook.org/content/free/contents/Chapter_27_Web.pdf>].
Cognato, "Standard Percent DNA Sequence Difference for Insects Does Not Predict Species Boundaries," Journal of Economic Entomology, 99(4):1037-1045, (2006). Abstract only. [Retrieved from the Internet Jul. 10, 2013: <URL: http://www.bioone.org/doi/abs/10.1603/0022-0493-99.4.1037?journalCode=ecen>].
Database GNPD [Online] Mintel: Accession No. 843414, "Wrinkle quencher", Aroma Crystal Therapy, Jan. 31, 2008.
Decatur et al., "rRNA modifications and ribosome function," TRENDS in Biochemical Sciences, 27(7):344-351, (2002).
Deng et al., "Culture observation and molecular phylogenetic analysis on the blooming green alga *Chaetomorpha valida* (Cladophorales, Chlorophyta) from China," *Chinese Journal of Oceanology and Limnology*, 31(3)552-559, (2013). Abstract only. [Retrieved from the Internet Jul. 10, 2013: <URL: http://link.springer.com/article/10.1007/s00343-013-2216-x>].
Dewhirst et al., "Discordant 165 and 235 rRNA Gene Phylogenies for the Genus Helicobacter: Implications for Phylogenetic Inference and Systematics," *Journal of Bacteriology*, American Society of Microbiology, 187(17):6106-6118, (2005).
Frazer et al., "Cross-Species Sequence Comparisons: A Review of Methods and Available Resources," *Genome Res.*, 13:1-12, (2003).
GenBank: Accession No. AJ245645, "Prototheca wickerhamii chloroplast partial genome," Aug. 17, 1999.
Harper, J. W. et al., "The DNA damage response: ten years after", Mol Cell. Dec. 14, 2007;28(5):739-45.
Kawachi et al., "Relationship between hydrocarbons and molecular phylogeny of Botryococcus braunii," Algal Research, 1:114-119, (2012).
Olive, P.L. et al., "The comet assay: a method to measure DNA damage in individual cells", Nat Protoc., 2006;1(1):23-9.
Stackebrandt et al., "Taxonomic Note: A Place for DNA-DNA Reassociation and 16S rRNA Sequence Analysis in the Present Species Definition in Bacteriology," International Journal Of Systematic Bacteriology, 44(4):846-849, (1994).
Ueno et al., "Optimization of heterotrophic culture conditions for n-alkane utilization and phylogenetic position based on the 18S rDNA sequence of a thermotolerant Prototheca zopfii strain," J Biosci Bioeng, 94(2):160-165, (2002). Abstract. [Retrieved from the Internet Dec. 1, 2014: <URL: http://www.ncbi.nlm.nih.gov/pubmed/16233286>].
EPO Application No. EP 14798050, Supplementary European Search Report and European Search Opinion, mailed Sep. 23, 2016.

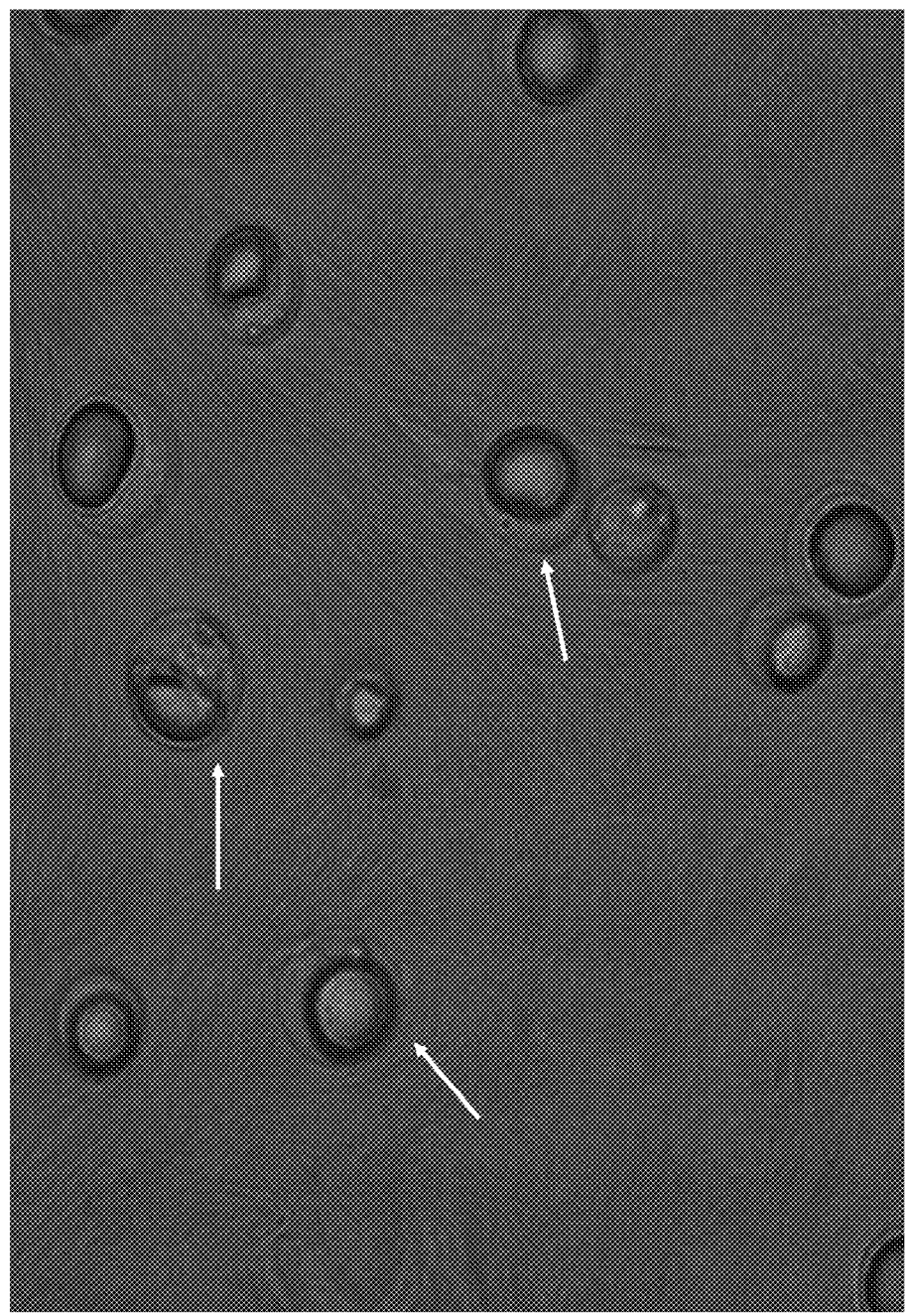

SEQUENCE LISTING

<160> NUMBER OF SEQ ID NOS: 27

<210> SEQ ID NO 1
<211> LENGTH: 565
<212> TYPE: DNA
<213> ORGANISM: Chlorella protothecoides

<400> SEQUENCE: 1

| | | | | | |
|---|---|---|---|---|---|
| tgttgaagaa | tgagccggcg | acttagaaaa | agtggcgtgg | ttaaggaaaa | attccgaagc | 60 |
| cttagcgaaa | gcgagtctga | atagggcgat | caaatatttt | aatatttaca | atttagtcat | 120 |
| tttttctaga | cccgaacccg | ggtgatctaa | ccatgaccag | gatgaaactt | gggtgatacc | 180 |
| aagtgaaggt | ccgaaccgac | cgatgttgaa | aaatcggcgg | atgagttgtg | gttagcggtg | 240 |
| aaataccagt | cgaacccgga | gctagctggt | tctccccgaa | atgcgttgag | gcgcagcagt | 300 |
| acatctagtc | tatctagggg | taaagcactg | tttcggtgcg | ggctgtgaaa | acggtaccaa | 360 |
| atcgtggcaa | actctgaata | ctagaaatga | cggtgtagta | gtgagactgt | gggggataag | 420 |
| ctccattgtc | aagagggaaa | cagcccagac | caccagctaa | ggccccaaaa | tggtaatgta | 480 |
| gtgacaaagg | aggtgaaaat | gcaaacacaa | ccaggaggtt | ggcttagaag | cagccatcct | 540 |
| ttaaagagtg | cgtaatagct | cactg | | | | 565 |

<210> SEQ ID NO 2
<211> LENGTH: 546
<212> TYPE: DNA
<213> ORGANISM: Chlorella protothecoides

<400> SEQUENCE: 2

| | | | | | |
|---|---|---|---|---|---|
| tgttgaagaa | tgagccggcg | acttagaaaa | cgtggcaagg | ttaaggaaac | gtatccggag | 60 |
| ccgaagcgaa | agcaagtctg | aacagggcga | ttaagtcatt | ttttctagac | ccgaacccgg | 120 |
| gtgatctaac | catgaccagg | atgaagcttg | ggtgacacca | agtgaaggtc | cgaaccgacc | 180 |
| gatgttgaaa | atcggcgga | tgagttgtgg | ttagcggtga | ataccagtc | gaactcggag | 240 |
| ctagctggtt | ctccccgaaa | tgcgttgagg | cgcagcggtt | cataaggctg | tctagggta | 300 |
| aagcactgtt | tcggtgcggg | ctgcgaaagc | ggtaccaaat | cgtggcaaac | tctgaatact | 360 |
| agatatgcta | tttatgggcc | agtgagacgg | tgggggataa | gcttcatcgt | cgagagggaa | 420 |
| acagcccaga | tcactagcta | aggccccaaa | atgatcgtta | agtgacaaag | gaggtgagaa | 480 |
| tgcagaaaca | accaggaggt | ttgcttagaa | gcagccaccc | tttaaagagt | gcgtaatagc | 540 |
| tcactg | | | | | | 546 |

<210> SEQ ID NO 3
<211> LENGTH: 565
<212> TYPE: DNA
<213> ORGANISM: Chlorella protothecoides

<400> SEQUENCE: 3

| | | | | | |
|---|---|---|---|---|---|
| tgttgaagaa | tgagccggcg | acttagaaaa | agtggcgtgg | ttaaggaaaa | attccgaagc | 60 |
| cttagcgaaa | gcgagtctga | atagggcgat | caaatatttt | aatatttaca | atttagtcat | 120 |
| tttttctaga | cccgaacccg | ggtgatctaa | ccatgaccag | gatgaaactt | gggtgatacc | 180 |
| aagtgaaggt | ccgaaccgac | cgatgttgaa | aaatcggcgg | atgagttgtg | gttagcggtg | 240 |
| aaataccagt | cgaacccgga | gctagctggt | tctccccgaa | atgcgttgag | gcgcagcagt | 300 |
| acatctagtc | tatctagggg | taaagcactg | tttcggtgcg | ggctgtgaaa | acggtaccaa | 360 |
| atcgtggcaa | actctgaata | ctagaaatga | cggtgtagta | gtgagactgt | gggggataag | 420 |

```
ctccattgtc aagagggaaa cagcccagac caccagctaa ggccccaaaa tggtaatgta      480
gtgacaaagg aggtgaaaat gcaaacacaa ccaggaggtt ggcttagaag cagccatcct      540
ttaaagagtg cgtaatagct cactg                                            565

<210> SEQ ID NO 4
<211> LENGTH: 565
<212> TYPE: DNA
<213> ORGANISM: Chlorella kessleri

<400> SEQUENCE: 4
tgttgaagaa tgagccggcg acttagaaaa agtggcgtgg ttaaggaaaa attccgaagc       60
cttagcgaaa gcgagtctga atagggcgat caaatatttt aatatttaca atttagtcat      120
tttttctaga cccgaacccg ggtgatctaa ccatgaccag gatgaaactt gggtgatacc      180
aagtgaaggt ccgaaccgac cgatgttgaa aaatcggcgg atgagttgtg gttagcggtg      240
aaataccagt cgaacccgga gctagctggt tctccccgaa atgcgttgag gcgcagcagt      300
acatctagtc tatctagggg taaagcactg tttcggtgcg ggctgtgaaa acggtaccaa      360
atcgtggcaa actctgaata ctagaaatga cggtgtagta gtgagactgt gggggataag      420
ctccattgtc aagagggaaa cagcccagac caccagctaa ggccccaaaa tggtaatgta      480
gtgacaaagg aggtgaaaat gcaaacacaa ccaggaggtt ggcttagaag cagccatcct      540
ttaaagagtg cgtaatagct cactg                                            565

<210> SEQ ID NO 5
<211> LENGTH: 548
<212> TYPE: DNA
<213> ORGANISM: Chlorella kessleri

<400> SEQUENCE: 5
tgttgaagaa tgagccggcg acttagaaga agtggcttgg ttaaggataa ctatccggag       60
ccagagcgaa agcaagtctg aatagggcgc ttaaaggtca cttttttctag acccgaaccc      120 gggtgatcta accatgacca ggatgaagct tgggtaacac cacgtgaagg tccgaaccga      180
ccgatgttga aaaatcggcg gatgagttgt ggttagcggt gaaataccaa tcgaactcgg      240
agctagctgg ttctccccga atgcgttga ggcgcagcgg tttatgaggc tgtctagggg      300
taaagcactg tttcggtgcg ggctgcgaaa gcggtaccaa atcgtggcaa actctgaata      360
ctagatatgc tattcatgag ccagtgagac ggtgggggat aagcttcatc gtcaagaggg      420
aaacagccca gatcaccagc taaggcccca aaatggtcgt taagtggcaa aggaggtgag      480
aatgctgaaa caaccaggag gtttgcttag aagcagccac cctttaaaga gtgcgtaata      540
gctcactg                                                               548

<210> SEQ ID NO 6
<211> LENGTH: 548
<212> TYPE: DNA
<213> ORGANISM: Chlorella kessleri

<400> SEQUENCE: 6
tgttgaagaa tgagccggcg acttagaaga agtggcttgg ttaaggataa ctatccggag       60
ccagagcgaa agcaagtctg aatagggcgc ttaaaggtca cttttttctag acccgaaccc      120 gggtgatcta accatgacca ggatgaagct tgggtaacac cacgtgaagg tccgaaccga      180
ccgatgttga aaaatcggcg gatgagttgt ggttagcggt gaaataccaa tcgaactcgg      240
```

```
agctagctgg ttctccccga aatgcgttga ggcgcagcgg tttatgaggc tgtctagggg      300
taaagcactg tttcggtgcg ggctgcgaaa gcggtaccaa atcgtggcaa actctgaata      360
ctagatatgc tattcatgag ccagtgagac ggtgggggat aagcttcatc gtcaagaggg      420
aaacagccca gatcaccagc taaggcccca aaatggtcgt taagtggcaa aggaggtgag      480
aatgctgaaa caaccaggag gtttgcttag aagcagccac cctttaaaga gtgcgtaata      540
gctcactg                                                               548
```

<210> SEQ ID NO 7
<211> LENGTH: 548
<212> TYPE: DNA
<213> ORGANISM: Parachlorella kessleri

<400> SEQUENCE: 7

```
tgttgaagaa tgagccggcg acttagaaga agtggcttgg ttaaggataa ctatccggag       60
ccagagcgaa agcaagtctg aatagggcgc ttaaaggtca cttttctag acccgaaccc      120 gggtgatcta accatgacca ggatgaagct tgggtaacac cacgtgaagg tccgaaccga      180
ccgatgttga aaaatcggcg gatgagttgt ggttagcggt gaaataccaa tcgaactcgg      240
agctagctgg ttctccccga aatgcgttga ggcgcagcgg tttatgaggc tgtctagggg      300
taaagcactg tttcggtgcg ggctgcgaaa gcggtaccaa atcgtggcaa actctgaata      360
ctagatatgc tattcatgag ccagtgagac ggtgggggat aagcttcatc gtcaagaggg      420
aaacagccca gatcaccagc taaggcccca aaatggtcgt taagtggcaa aggaggtgag      480
aatgctgaaa caaccaggag gtttgcttag aagcagccac cctttaaaga gtgcgtaata      540
gctcactg                                                               548
```

<210> SEQ ID NO 8
<211> LENGTH: 548
<212> TYPE: DNA
<213> ORGANISM: Parachlorella kessleri

<400> SEQUENCE: 8

```
tgttgaagaa tgagccggcg acttagaaga agtggcttgg ttaaggataa ctatccggag       60
ccagagcgaa agcaagtctg aatagggcgc ttaaaggtca cttttctag acccgaaccc      120 gggtgatcta accatgacca ggatgaagct tgggtaacac cacgtgaagg tccgaaccga      180
ccgatgttga aaaatcggcg gatgagttgt ggttagcggt gaaataccaa tcgaactcgg      240
agctagctgg ttctccccga aatgcgttga ggcgcagcgg tttatgaggc tgtctagggg      300
taaagcactg tttcggtgcg ggctgcgaaa gcggtaccaa atcgtggcaa actctgaata      360
ctagatatgc tattcatgag ccagtgagac ggtgggggat aagcttcatc gtcaagaggg      420
aaacagccca gatcaccagc taaggcccca aaatggtcgt taagtggcaa aggaggtgag      480
aatgctgaaa caaccaggag gtttgcttag aagcagccac cctttaaaga gtgcgtaata      540
gctcactg                                                               548
```

<210> SEQ ID NO 9
<211> LENGTH: 565
<212> TYPE: DNA
<213> ORGANISM: Parachlorella kessleri

<400> SEQUENCE: 9

```
tgttgaagaa tgagccggcg acttagaaaa agtggcgtgg ttaaggaaaa attccgaagc       60
cttagcgaaa gcgagtctga ataggggcgat caaatatttt aatatttaca atttagtcat      120
```

```
tttttctaga cccgaacccg ggtgatctaa ccatgaccag gatgaaactt gggtgatacc    180
aagtgaaggt ccgaaccgac cgatgttgaa aaatcggcgg atgagttgtg gttagcggtg    240
aaataccagt cgaacccgga gctagctggt tctccccgaa atgcgttgag gcgcagcagt    300
acatctagtc tatctagggg taaagcactg tttcggtgcg ggctgtgaaa acggtaccaa    360
atcgtggcaa actctgaata ctagaaatga cggtgtagta gtgagactgt ggggataag    420 ctccattgtc aagagggaaa cagcccagac caccagctaa ggcccaaaa tggtaatgta    480 gtgacaaagg aggtgaaaat gcaaacacaa ccaggaggtt ggcttagaag cagccatcct    540
ttaaagagtg cgtaatagct cactg                                          565

<210> SEQ ID NO 10
<211> LENGTH: 541
<212> TYPE: DNA
<213> ORGANISM: Prototheca stagnora

<400> SEQUENCE: 10
tgttgaagaa tgagccggcg agttaaaaaa aatggcatgg ttaaagatat ttctctgaag     60
ccatagcgaa agcaagtttt acaagctata gtcattttt ttagacccga aaccgagtga    120
tctacccatg atcagggtga agtgttggtc aaataacatg gaggcccgaa ccgactaatg    180
gtgaaaaatt agcggatgaa ttgtgggtag ggcgaaaaa ccaatcgaac tcggagttag    240
ctggttctcc ccgaaatgcg tttaggcgca gcagtagcaa cacaaataga ggggtaaagc    300
actgtttctt ttgtgggctt cgaaagttgt acctcaaagt ggcaaactct gaatactcta    360
tttagatatc tactagtgag accttggggg ataagctcct tggtcaaaag ggaaacagcc    420
cagatcacca gttaaggccc caaaatgaaa atgatagtga ctaaggacgt gagtatgtca    480
aaacctccag caggttagct tagaagcagc aatccttca agagtgcgta atagctcact    540
g                                                                   541

<210> SEQ ID NO 11
<211> LENGTH: 573
<212> TYPE: DNA
<213> ORGANISM: Prototheca moriformis

<400> SEQUENCE: 11
tgttgaagaa tgagccggcg acttaaaata aatggcaggc taagagaatt aataactcga     60
aacctaagcg aaagcaagtc ttaatagggc gctaatttaa caaaacatta ataaaaatct    120
aaagtcattt attttagacc cgaacctgag tgatctaacc atggtcagga tgaaacttgg    180
gtgacaccaa gtggaagtcc gaaccgaccg atgttgaaaa atcggcggat gaactgtggt    240
tagtggtgaa ataccagtcg aactcagagc tagctggttc tccccgaaat gcgttgaggc    300
gcagcaatat atctcgtcta tctagggta aagcactgtt tcggtgcggg ctatgaaaat    360
ggtaccaaat cgtggcaaac tctgaatact agaaatgacg atatattagt gagactatgg    420
gggataagct ccatagtcga gagggaaaca gcccagacca ccagttaagg ccccaaaatg    480
ataatgaagt ggtaaaggag gtgaaaatgc aaatacaacc aggaggttgg cttagaagca    540
gccatccttt aaagagtgcg taatagctca ctg                                 573

<210> SEQ ID NO 12
<211> LENGTH: 573
<212> TYPE: DNA
<213> ORGANISM: Prototheca moriformis
```

<400> SEQUENCE: 12

```
tgttgaagaa tgagccggcg acttaaaata aatggcaggc taagagaatt aataactcga    60
aacctaagcg aaagcaagtc ttaatagggc gctaatttaa caaaacatta aataaaatct   120
aaagtcattt attttagacc cgaacctgag tgatctaacc atggtcagga tgaaacttgg   180
gtgacaccaa gtggaagtcc gaaccgaccg atgttgaaaa atcggcggat gaactgtggt   240
tagtggtgaa ataccagtcg aactcagagc tagctggttc tccccgaaat gcgttgaggc   300
gcagcaatat atctcgtcta tctaggggta aagcactgtt tcggtgcggg ctatgaaaat   360
ggtaccaaat cgtggcaaac tctgaatact agaaatgacg atatattagt gagactatgg   420
gggataagct ccatagtcga gagggaaaca gcccagacca ccagttaagg ccccaaaatg   480
ataatgaagt ggtaaaggag gtgaaaatgc aaatacaacc aggaggttgg cttagaagca   540
gccatccttt aaagagtgcg taatagctca ctg                                573
```

<210> SEQ ID NO 13
<211> LENGTH: 565
<212> TYPE: DNA
<213> ORGANISM: Chlorella minutissima

<400> SEQUENCE: 13

```
tgttgaagaa tgagccggcg acttagaaaa agtggcgtgg ttaaggaaaa attccgaagc    60
cttagcgaaa gcgagtctga atagggcgat caaatatttt aatatttaca atttagtcat   120
tttttctaga cccgaacccg ggtgatctaa ccatgaccag gatgaaactt gggtgatacc   180
aagtgaaggt ccgaaccgac cgatgttgaa aaatcggcgg atgagttgtg gttagcggtg   240
aaataccagt cgaacccgga gctagctggt ctccccgaa atgcgttgag gcgcagcagt   300
acatctagtc tatctagggg taaagcactg tttcggtgcg ggctgtgaaa acggtaccaa   360
atcgtggcaa actctgaata ctagaaatga cggtgtagta gtgagactgt gggggataag   420
ctccattgtc aagagggaaa cagcccagac caccagctaa ggccccaaaa tggtaatgta   480
gtgacaaagg aggtgaaaat gcaaacacaa ccaggaggtt ggcttagaag cagccatcct   540
ttaaagagtg cgtaatagct cactg                                         565
```

<210> SEQ ID NO 14
<211> LENGTH: 565
<212> TYPE: DNA
<213> ORGANISM: Chlorella sp.

<400> SEQUENCE: 14

```
tgttgaagaa tgagccggcg acttagaaaa agtggcgtgg ttaaggaaaa attccgaagc    60
cttagcgaaa gcgagtctga atagggcgat caaatatttt aatatttaca atttagtcat   120
tttttctaga cccgaacccg ggtgatctaa ccatgaccag gatgaaactt gggtgatacc   180
aagtgaaggt ccgaaccgac cgatgttgaa aaatcggcgg atgagttgtg gttagcggtg   240
aaataccagt cgaacccgga gctagctggt tctccccgaa atgcgttgag gcgcagcagt   300
acatctagtc tatctagggg taaagcactg tttcggtgcg ggctgtgaaa acggtaccaa   360
atcgtggcaa actctgaata ctagaaatga cggtgtagta gtgagactgt gggggataag   420
ctccattgtc aagagggaaa cagcccagac caccagctaa ggccccaaaa tggtaatgta   480
gtgacaaagg aggtgaaaat gcaaacacaa ccaggaggtt ggcttagaag cagccatcct   540
ttaaagagtg cgtaatagct cactg                                         565
```

<210> SEQ ID NO 15
<211> LENGTH: 546
<212> TYPE: DNA
<213> ORGANISM: Chlorella sp.

<400> SEQUENCE: 15

```
tgttgaagaa tgagccggcg acttagaaaa cgtggcaagg ttaaggacat gtatccggag      60
ccgaagcgaa agcaagtctg aatagggcgc ctaagtcatt ttttctagac ccgaacccgg     120
gtgatctaac catgaccagg atgaagcttg ggtgacacca agtgaaggtc cgaaccgacc     180
gatgttgaaa atcggcgga tgagttgtgg ttagcggtga ataccagtc gaactcggag      240 ctagctggtt ctccccgaaa tgcgttgagg cgcagcggtt cataaggctg tctaggggta     300
aagcactgtt tcggtgcggg ctgcgaaagc ggtaccaaat cgtggcaaac tctgaatact     360
agatatgcta tttatgagcc agtgagacgg tgggggataa gcttcatcgt cgagagggaa     420
acagcccaga tcactagcta aggcccctaa atgatcgtta agtgacaaag gaggtgagaa     480
tgcagaaaca accaggaggt ttgcttagaa gcagccaccc tttaaagagt gcgtaatagc     540
tcactg                                                               546
```

<210> SEQ ID NO 16
<211> LENGTH: 550
<212> TYPE: DNA
<213> ORGANISM: Chlorella sorokiniana

<400> SEQUENCE: 16

```
tgttgaagaa tgagccggcg acttatagga agtggcaggg ttaaggaaga atctccggag      60
cccaagcgaa agcgagtctg aaaagggcga tttggtcact tcttatggac ccgaacctgg     120
atgatctaat catggccaag ttgaagcatg ggtaacacta tgtcgaggac tgaacccacc     180
gatgttgaaa atcggggga tgagctgtga ttagcggtga aattccaatc gaattcagag      240
ctagctggat ctccccgaaa tgcgttgagg cgcagcggcg acgatgtcct gtctaagggt     300
agagcgactg tttcggtgcg ggctgcgaaa gcggtaccaa gtcgtggcaa actccgaata     360
ttaggcaaag gattccgtga gccagtgaga ctgtggggga taagcttcat agtcaagagg     420
gaaacagccc agaccatcag ctaaggcccc taaatggctg ctaagtggaa aaggatgtga     480
gaatgctgaa acaaccagga ggttcgctta gaagcagcta ttccttgaaa gagtgcgtaa     540
tagctcactg                                                           550
```

<210> SEQ ID NO 17
<211> LENGTH: 548
<212> TYPE: DNA
<213> ORGANISM: Parachlorella beijerinkii

<400> SEQUENCE: 17

```
tgttgaagaa tgagccggcg acttagaaga agtggcttgg ttaaggataa ctatccggag      60
ccagagcgaa agcaagtctg aatagggcgc ttaaaggtca cttttttctag acccgaaccc     120 gggtgatcta accatgacca ggatgaagct tgggtaacac cacgtgaagg tccgaaccga     180
ccgatgttga aaatcggcg gatgagttgt ggttagcggt gaaataccaa tcgaactcgg      240
agctagctgg ttctccccga aatgcgttga ggcgcagcgg tttatgaggc tgtctagggg     300
taaagcactg tttcggtgcg ggctgcgaaa gcggtaccaa atcgtggcaa actctgaata     360
ctagatatgc tattcatgag ccagtgagac ggtgggggat aagcttcatc gtcaagaggg     420
aaacagccca gatcaccagc taaggcccca aaatggtcgt taagtggcaa aggaggtgag     480
```

-continued

```
aatgctgaaa caaccaggag gtttgcttag aagcagccac cctttaaaga gtgcgtaata    540
gctcactg                                                             548

<210> SEQ ID NO 18
<211> LENGTH: 556
<212> TYPE: DNA
<213> ORGANISM: Chlorella luteoviridis

<400> SEQUENCE: 18
tgttgaagaa tgagccggcg acttataggg ggtggcgtgg ttaaggaagt aatccgaagc     60
caaagcgaaa gcaagttttc aatagagcga ttttgtcacc ccttatggac ccgaacccgg    120
gtgatctaac cttgaccagg atgaagcttg gtaacacca agtgaaggtc cgaactcatc    180
gatcttgaaa atcgtggga tgagttgggg ttagttggtt aaatgctaat cgaactcgga    240
gctagctggt tctccccgaa atgtgttgag gcgcagcgat taacgaaata ttttgtacgg    300
tttaggggta aagcactgtt tcggtgcggg ctgcgaaagc ggtaccaaat cgtggcaaac    360
tctgaatact aagcctgtat accgttagtc agtgagagta tagggataa gctctatact    420
caagagggaa acagcccaga tcaccagcta aggccccaaa atgacagcta agtggcaaag    480
gaggtgaaag tgcagaaaca accaggaggt tcgcttagaa gcagcaaccc tttaaagagt    540
gcgtaatagc tcactg                                                    556

<210> SEQ ID NO 19
<211> LENGTH: 548
<212> TYPE: DNA
<213> ORGANISM: Chlorella vulgaris

<400> SEQUENCE: 19
tgttgaagaa tgagccggcg acttagaaga agtggcttgg ttaaggataa ctatccggag     60
ccagagcgaa agcaagtctg aatagggcgc ttaaggtca cttttctag acccgaaccc    120
gggtgatcta accatgacca ggatgaagct tgggtaacac cacgtgaagg tccgaaccga    180
ccgatgttga aaaatcggcg gatgagttgt ggttagcggt gaaataccaa tcgaactcgg    240
agctagctgg ttctccccga aatgcgttga ggcgcagcgg tttatgaggc tgtctagggg    300
taaagcactg tttcggtgcg ggctgcgaaa gcggtaccaa atcgtggcaa actctgaata    360
ctagatatgc tattcatgag ccagtgagac ggtgggggat aagcttcatc gtcaagaggg    420
aaacagccca gatcaccagc taaggcccca aaatggtcgt taagtggcaa aggaggtgag    480
aatgctgaaa caaccaggag gtttgcttag aagcagccac cctttaaaga gtgcgtaata    540
gctcactg                                                             548

<210> SEQ ID NO 20
<211> LENGTH: 565
<212> TYPE: DNA
<213> ORGANISM: Chlorella reisiglii

<400> SEQUENCE: 20
tgttgaagaa tgagccggcg acttagaaaa agtggcgtgg ttaaggaaaa attccgaagc     60
cttagcgaaa gcgagtctga atagggcgat caaatatttt aatatttaca atttagtcat    120
tttttctaga cccgaacccg ggtgatctaa ccatgaccag gatgaaactt gggtgatacc    180
aagtgaaggt ccgaaccgac cgatgttgaa aaatcggcgg atgagttgtg gttagcggtg    240
aaataccagt cgaacccgga gctagctggt tctccccgaa atgcgttgag gcgcagcagt    300
acatctagtc tatctagggg taaagcactg tttcggtgcg ggctgtgaaa acggtaccaa    360
```

```
atcgtggcaa actctgaata ctagaaatga cggtgtagta gtgagactgt gggggataag        420
ctccattgtc aagagggaaa cagcccagac caccagctaa ggccccaaaa tggtaatgta        480
gtgacaaagg aggtgaaaat gcaaacacaa ccaggaggtt ggcttagaag cagccatcct        540
ttaaagagtg cgtaatagct cactg                                              565

<210> SEQ ID NO 21
<211> LENGTH: 573
<212> TYPE: DNA
<213> ORGANISM: Chlorella ellipsoidea

<400> SEQUENCE: 21
tgttgaagaa tgagccggcg acttataggg ggtggcttgg ttaaggacta caatccgaag         60
cccaagcgaa agcaagtttg aagtgtacac acattgtgtg tctagagcga ttttgtcact        120
ccttatggac ccgaacccgg gtgatctatt catggccagg atgaagcttg ggtaacacca        180
agtgaaggtc cgaactcatc gatgttgaaa atcgtggga tgagttgtga atagggggtga        240 aatgccaatc gaactcggag ctagctggtt ctccccgaaa tgtgttgagg cgcagcgatt        300
cacgatctaa agtacggttt aggggtaaag cactgtttcg gtgcgggctg ttaacgcggt        360
accaaatcgt ggcaaactaa gaatactaaa cttgtatgcc gtgaatcagt gagactaaga        420
gggataagct tcttagtcaa gagggaaaca gcccagatca ccagctaagg ccccaaaatg        480
acagctaagt ggcaaaggag gtgagagtgc agaaacaacc aggaggtttg cttagaagca        540
gccatccttt aaagagtgcg taatagctca ctg                                     573

<210> SEQ ID NO 22
<211> LENGTH: 573
<212> TYPE: DNA
<213> ORGANISM: Chlorella saccharophila

<400> SEQUENCE: 22
tgttgaagaa tgagccggcg acttataggg ggtggcttgg ttaaggacta caatccgaag         60
cccaagcgaa agcaagtttg aagtgtacac acgttgtgtg tctagagcga ttttgtcact        120
ccttatggac ccgaacccgg gtgatctatt catggccagg atgaagcttg ggtaacacca        180
agtgaaggtc cgaactcatc gatgttgaaa atcgtggga tgagttgtga atagggggtga        240 aatgccaatc gaactcggag ctagctggtt ctccccgaaa tgtgttgagg cgcagcgatt        300
cacgatctaa agtacggttt aggggtaaag cactgtttcg gtgcgggctg ttaacgcggt        360
accaaatcgt ggcaaactaa gaatactaaa cttgtatgcc gtgaatcagt gagactaaga        420
gggataagct tcttagtcaa gagggaaaca gcccagatca ccagctaagg ccccaaaatg        480
acagctaagt ggcaaaggag gtgagagtgc agaaacaacc aggaggtttg cttagaagca        540
gccatccttt aaagagtgcg taatagctca ctg                                     573

<210> SEQ ID NO 23
<211> LENGTH: 573
<212> TYPE: DNA
<213> ORGANISM: Chlorella saccharophila

<400> SEQUENCE: 23
tgttgaagaa tgagccggcg acttataggg ggtggcttgg ttaaggacta caatccgaag         60
cccaagcgaa agcaagtttg aagtgtacac acattgtgtg tctagagcga ttttgtcact        120
ccttatggac ccgaacccgg gtgatctatt catggccagg atgaagcttg ggtaacacca        180
```

```
agtgaaggtc cgaactcatc gatgttgaaa aatcgtggga tgagttgtga atagggg tga    240 aatgccaatc gaactcggag ctagctggtt ctccccgaaa tgtgttgagg cgcagcgatt    300
cacgatctaa agtacggttt aggggtaaag cactgtttcg gtgcgggctg ttaacgcggt    360
accaaatcgt ggcaaactaa gaatactaaa cttgtatgcc gtgaatcagt gagactaaga    420
gggataagct tcttagtcaa gagggaaaca gcccagatca ccagctaagg ccccaaaatg    480
acagctaagt ggcaaaggag gtgagagtgc agaaacaacc aggaggtttg cttagaagca    540
gccatccttt aaagagtgcg taatagctca ctg                                  573

<210> SEQ ID NO 24
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
tgttgaagaa tgagccggcg ac                                              22

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
cagtgagcta ttacgcactc                                                 20

<210> SEQ ID NO 26
<211> LENGTH: 546
<212> TYPE: DNA
<213> ORGANISM: Chlorella protothecoides

<400> SEQUENCE: 26
tgttgaagaa tgagccggcg acttagaaaa cgtggcaagg ttaaggaaac gtatccggag    60
ccgaagcgaa agcaagtctg aacagggcga ttaagtcatt ttttctagac ccgaacccgg    120
gtgatctaac catgaccagg atgaagcttg ggtgacacca agtgaaggtc cgaaccgacc    180
gatgttgaaa aatcggcgga tgagttgtgg ttagcggtga ataccagtc gaactcggag    240 ctagctggtt ctccccgaaa tgcgttgagg cgcagcggtt cataaggctg tctagggta    300 aagcactgtt tcggtgcggg ctgcgaaagc ggtaccaaat cgtggcaaac tctgaatact    360
agatatgcta tttatgggcc agtgagacgg tgggggataa gcttcatcgt cgagagggaa    420
acagcccaga tcactagcta aggccccaaa atgatcgtta agtgacaaag gaggtgagaa    480
tgcagaaaca accaggaggt ttgcttagaa gcagccaccc tttaaagagt gcgtaatagc    540
tcactg                                                               546

<210> SEQ ID NO 27
<211> LENGTH: 565
<212> TYPE: DNA
<213> ORGANISM: Chlorella protothecoides

<400> SEQUENCE: 27
tgttgaagaa tgagccggcg acttagaaaa agtggcgtgg ttaaggaaaa attccgaagc    60
cttagcgaaa gcgagtctga ataggg cgat caaatatttt aatatttaca atttagtcat    120
```

```
tttttctaga cccgaacccg ggtgatctaa ccatgaccag gatgaaactt gggtgatacc     180
aagtgaaggt ccgaaccgac cgatgttgaa aaatcggcgg atgagttgtg gttagcggtg     240
aaataccagt cgaacccgga gctagctggt tctccccgaa atgcgttgag gcgcagcagt     300
acatctagtc tatctagggg taaagcactg tttcggtgcg ggctgtgaaa acggtaccaa     360
atcgtggcaa actctgaata ctagaaatga cggtgtagta gtgagactgt gggggataag     420
ctccattgtc aagagggaaa cagcccagac caccagctaa ggcccaaaa tggtaatgta      480 gtgacaaagg aggtgaaaat gcaaacacaa ccaggaggtt ggcttagaag cagccatcct     540
ttaaagagtg cgtaatagct cactg                                           565
```

COSMETIC COMPOSITIONS COMPRISING MICROALGAL COMPONENTS

CROSS REFERENCE TO RELATED APPLICATIONS

This application is a continuation of U.S. application Ser. No. 14/015,921, filed Aug. 30, 2013, which is a continuation of U.S. application Ser. No. 13/128,217, filed Jun. 27, 2011, now U.S. Pat. No. 8,557,249, which is a US national stage application under 35 USC 371 of International Application No. PCT/US2009/063740, filed Nov. 9, 2009, which claims the benefit under 35 USC 119(e) of U.S. Provisional Patent Application No. 61/112,464, filed Nov. 7, 2008, each of which is incorporated by reference herein.

REFERENCE TO A SEQUENCE LISTING

This application includes an electronic sequence listing in a file named "471302-Sequence.txt", created on Nov. 3, 2015 and containing 22,173 bytes, which is hereby incorporated by reference in its entirety for all purposes.

FIELD OF THE INVENTION

The invention resides in the fields of cosmetics, cosmetics ingredients, and aquaculture.

BACKGROUND OF THE INVENTION

Seed oils or animal fats have been used in conventional cosmetic products for years. Oils from plants are typically obtained from cultivation or harvesting wild biomass. The composition of plant oils changes in response to weather, seasonal influences such as photoperiod, temperature, soil acidity, soil salinity, and pests.

SUMMARY OF THE INVENTION

In one aspect, the present invention is directed to a cosmetic composition comprising at least 1% w/w microalgal biomass and at least one other cosmetic ingredient, in which the microalgal biomass comprises at least 10% microalgal oil by dry weight. In some cases, the biomass contains at least 25% microalgal oil by dry weight. In other cases, the biomass contains at least 35% microalgal oil by dry weight. In yet other cases, the biomass contains at least 45% microalgal oil by dry weight. In still other cases, the biomass contains at least 55% microalgal oil by dry weight. In at least one embodiment, the biomass comprises predominantly intact algal cells.

In some embodiments of the cosmetic composition described above, the biomass contains 10-90% microalgal oil by dry weight. In some cases, the biomass contains from 25-80% microalgal oil by dry weight. In other cases, the biomass contains from 35-70% microalgal oil by dry weight. In still other cases, the biomass contains from 45-60% microalgal oil by dry weight.

In various embodiments of the cosmetic compositions in accordance with the present invention, the composition comprises at least 1% w/w microalgal biomass. In other cases, the composition comprises at least 10% w/w microalgal biomass. In yet other cases, the composition comprises at least 25% w/w microalgal biomass. In still other cases, the composition comprises at least 50% w/w microalgal biomass. In at least one embodiment, a cosmetic composition of the present invention is free of oil other than microalgal oil entrapped inside the biomass.

In some cases, microalgal cosmetic compositions comprise biomass which includes other constituents in addition to microalgal oil, such as carotenoids. In one embodiment, the biomass comprises at least 10 µg of carotenoids per gram of biomass. In other embodiments, the biomass comprises at least 25 µg or at least 50 µg of carotenoids per gram of biomass. In still other embodiments, the biomass comprises 10-100 µg of carotenoids per gram of biomass.

In at least one embodiment, the cosmetic composition described above comprises biomass derived from microalgae cultured heterotrophically.

In another aspect, the present invention is directed to a cosmetic composition comprising at least 1% w/w or v/v microalgal oil and at least one other cosmetic ingredient, in which the microalgal oil is derived from microalgae cultured heterotrophically. In some cases, the microalgae comprise 10-90% microalgal oil by dry weight. In other cases, the microalgae comprise 25-80% microalgal oil by dry weight. In yet other cases, the microalgae comprise 35-70% microalgal oil by dry weight. In still other cases, the microalgae comprise 45-60% microalgal oil by dry weight.

In various embodiments of the cosmetic compositions comprising microalgal oil, the composition comprises at least 1% w/w or v/v microalgal oil. In other cases, the composition comprises at least 10% w/w or v/v microalgal oil. In yet other cases, the composition comprises at least 25% w/w or v/v microalgal oil. In still other cases, the composition comprises at least 50% w/w or v/v microalgal oil. In at least one embodiment, the cosmetic composition of the present invention is free of oil other than microalgal oil.

In some embodiments, the cosmetic composition comprises microalgal oil composed of a mixture of oil from at least two distinct species of microalgae. In other embodiments, the cosmetic composition comprises biomass composed of a mixture of at least two distinct species of microalgae. In some cases, at least two of the distinct species of microalgae have been separately cultured. In some cases, at least two of the distinct species have different glycerolipid profiles. In still other embodiments, the cosmetic composition comprises microalgal biomass composed of a mixture of at least two different microalgae population with different glycerolipid profiles.

In another aspect, the present invention is directed to a method of making a cosmetic composition comprising combining microalgal biomass with at least one other cosmetic ingredient to form a cosmetic composition, in which the microalgal biomass comprises at least 15% microalgal oil by dry weight. In some cases, the method further comprises culturing a population of microalgae to generate the biomass. In some cases, the method further comprises drying the biomass prior to combining the biomass with the at least one other cosmetic ingredient.

In some embodiments, the cosmetic composition formed by the methods of the invention comprises biomass containing 10-75% oil by dry weight. In at least one embodiment, the biomass comprises predominantly intact microalgal cells. In other embodiments, the cosmetic composition comprises intact microalgal cells that have been homogenized to form a whole cell dispersion.

In some cases, the microalgal biomass comprises at least 1% of the cosmetic composition. In other cases, the microalgal biomass comprises at least 5% of the cosmetic composition. In yet other cases, the microalgal biomass comprises at least 25% of the cosmetic composition. In still other cases, the microalgal biomass comprises at least 50% of the cosmetic composition.

In another aspect, the present invention is directed to a method of making a cosmetic composition comprising combining algal oil obtained from microalgal biomass containing at least 10% microalgal oil by dry weight with one or more other cosmetic ingredients to form a cosmetic composition. In some cases, the biomass comprises 10-75% microalgal oil by dry weight. In some embodiments, the method further comprises culturing a population of microalgae to generate the biomass, and extracting the algal oil from the biomass. In some cases, the microalgae are cultured under heterotrophic conditions.

In various embodiments, the microalgal oil comprises at least 1% by weight or by volume of the cosmetic composition formed by the method described above. In some cases, the algal oil comprises at least 5% by weight or volume of the cosmetic composition. In yet other cases, the algal oil comprises at least 25% by weight or volume of the cosmetic composition. In still other cases, the algal oil comprises at least 50% by weight or by volume of the cosmetic composition.

In another aspect, the present invention is directed to a method of using a microalgal biomass composition to soften and impart pliability to skin. In one embodiment, the method comprises applying to human skin a composition comprising predominantly intact microalgal cells containing at least 10% microalgal oil by dry weight. In some cases, the method further comprises retaining the composition in contact with the skin for at least 1 hour. In at least one embodiment, the composition is retained in contact with the skin for at least 3 hours. In some cases, the method of using a microalgal biomass composition further comprises retaining the composition in contact with the skin for a period of time sufficient to release at least 50% of the oil from the intact microalgal cells by enzymatic degradation of the cells.

In various embodiments of the method of using a microalgal biomass composition to soften and impart pliability to skin and hair, the composition comprises cells containing at least 15% oil by dry weight. In some cases, the composition comprises cells containing at least 35% oil by dry weight. In other cases, the composition comprises cells containing at least 45% oil by dry weight. In one embodiment, the composition comprises cells containing 15-90% oil by dry weight. In another embodiment, the composition comprises cells containing 25-80% oil by dry weight. In still another embodiment, the composition comprises cells containing 35-70% oil by dry weight. In a preferred embodiment, the composition comprises cells containing 45-60% oil by dry weight.

In any one of the cosmetic compositions and/or methods described above, the biomass can be derived from a culture of microalgae selected from those recited herein. In some cases, the microalgae is a species of the genus *Chlorella*. In various embodiments, the microalgae is selected from the group consisting of *Chlorella anitrata, Chlorella antarctica, Chlorella aureoviridis, Chlorella candida, Chlorella capsulata, Chlorella desiccata, Chlorella ellipsoidea, Chlorella emersonii, Chlorella fusca, Chlorella fusca* var. *vacuolata, Chlorella glucotropha, Chlorella infusionum, Chlorella infusionum* var. *Actophila, Chlorella infusionum* var. *Auxenophila, Chlorella kessleri, Chlorella luteoviridis, Chlorella luteoviridis* var. *aureoviridis, Chlorella luteoviridis* var. *Lutescens, Chlorella miniata, Chlorella minutissima, Chlorella mutabilis, Chlorella nocturna, Chlorella parva, Chlorella photophila, Chlorella pringsheimii, Chlorella protothecoides, Chlorella pyrenoidosa, Chlorella regularis, Chlorella regularis* var. *minima, Chlorella regularis* var. *umbricata, Chlorella reisiglii, Chlorella saccharophila, Chlorella saccharophila* var. *ellipsoidea, Chlorella salina, Chlorella simplex, Chlorella sorokiniana, Chlorella* sp., *Chlorella sphaerica, Chlorella stigmatophora, Chlorella vanniellii, Chlorella vulgaris, Chlorella vulgaris, Chlorella vulgaris f. tertia, Chlorella vulgaris* var. *airidis, Chlorella vulgaris* var. *vulgaris, Chlorella vulgaris* var. *vulgaris f. tertia, Chlorella vulgaris* var. *vulgaris f. viridis, Chlorella xanthella*, and *Chlorella zofingiensis*.

In any one of the cosmetic compositions and/or methods described above, the at least one other cosmetic ingredient comprises an ingredient selected from the group consisting of absorbents, abrasives, anticaking agents, antifoaming agents, antimicrobial agents, binders, biological additives, buffering agents, bulking agents, chemical additives, cosmetic biocides, denaturants, cosmetic astringents, drug astringents, external analgesics, film formers, humectants, opacifying agents, fragrances, flavor oils, pigments, colorings, essential oils, skin sensates, emollients, skin soothing agents, skin healing agents, pH adjusters, plasticizers, preservatives, preservative enhancers, propellants, reducing agents, skin-conditioning agents, skin penetration enhancing agents, skin protectants, solvents, suspending agents, emulsifiers, thickening agents, solubilizing agents, soaps, sunscreens, sunblocks, ultraviolet light absorbers or scattering agents, sunless tanning agents, antioxidants and/or radical scavengers, chelating agents, sequestrants, anti-acne agents, anti-inflammatory agents, anti-androgens, depilation agents, desquamation agents/exfoliants, organic hydroxy acids, vitamins, vitamin derivatives, and natural extracts. In at least one embodiment, the other cosmetic ingredient comprises a soap. In some cases, the soap comprises a saponified oil derived from microalgae.

Any two or more of the various embodiments described above or herein can be combined together to produce additional embodiments encompassed within the scope of the present invention.

BRIEF DESCRIPTION OF THE FIGURE

The FIGURE shows a cross-section slice of whole microalgal soap containing high oil microalgal biomass under light microscopy at 1000× magnification. The arrows point to whole microalgae in the soap composition. The whole microalgae is approximately 8 microns in diameter.

DETAILED DESCRIPTION OF THE INVENTION

This detailed description of the invention is divided into sections and subsections for the convenience of the reader. Section I provides definitions for various terms used herein. Section II, in parts A-E, describes methods for preparing microalgal biomass, including suitable organisms (A), methods of generating a microalgae strain lacking in or having significantly reduced pigmentation (B), culture conditions (C), concentration conditions (D), and chemical composition of the biomass produced in accordance with the invention (E). Section III, in parts A-D, describes methods for processing the microalgal biomass into algal flake (A), algal powder (B), algal flour (C), and algal oil (D) of the invention. Section IV describes cosmetic compositions of the invention and methods of combining microalgal biomass with other cosmetic ingredients.

I. Definitions

Unless defined otherwise, all technical and scientific terms used herein have the meaning commonly understood by a person skilled in the art to which this invention belongs. The following references provide one of skill with a general definition of many of the terms used in this invention: Singleton et al., *Dictionary of Microbiology and Molecular Biology* (2nd ed. 1994); *The Cambridge Dictionary of Science and Technology* (Walker ed., 1988); *The Glossary of Genetics*, 5th Ed., R. Rieger et al. (eds.), Springer Verlag (1991); and Hale & Marham, *The Harper Collins Dictionary of Biology* (1991). As used herein, the following terms have the meanings ascribed to them unless specified otherwise.

As used with reference to a nucleic acid, "active in microalgae" refers to a nucleic acid that is functional in microalgae. For example, a promoter that has been used to drive an antibiotic resistance gene to impart antibiotic resistance to a transgenic microalgae is active in microalgae. Examples of promoters active in microalgae are promoters endogenous to certain algae species and promoters found in plant viruses.

"Axenic" means a culture of an organism that is free from contamination by other living organisms.

"Bioreactor" means an enclosure or partial enclosure in which cells are cultured, optionally in suspension.

The term "co-culture", and variants thereof such as "co-cultivate", refer to the presence of two or more types of cells in the same bioreactor. The two or more types of cells may both be microorganisms, such as microalgae, or may be a microalgal cell cultured with a different cell type. The culture conditions may be those that foster growth and/or propagation of the two or more cell types or those that facilitate growth and/or proliferation of one, or a subset, of the two or more cells while maintaining cellular growth for the remainder.

The term "cofactor" is used herein to refer to any molecule, other than the substrate, that is required for an enzyme to carry out its enzymatic activity.

As used herein, "cosmetic ingredient" means an ingredient conventionally used in cosmetic products that is not physically or chemically incompatible with the microalgal components described herein. "Cosmetic ingredients" include, without limitation, absorbents, abrasives, anticaking agents, antifoaming agents, antimicrobial agents, binders, biological additives, buffering agents, bulking agents, chemical additives, cosmetic biocides, denaturants, cosmetic astringents, drug astringents, external analgesics, film formers, humectants, opacifying agents, fragrances, pigments, colorings, essential oils, skin sensates, emollients, skin soothing agents, skin healing agents, pH adjusters, plasticizers, preservatives, preservative enhancers, propellants, reducing agents, skin-conditioning agents, skin penetration enhancing agents, skin protectants, solvents, suspending agents, emulsifiers, thickening agents, solubilizing agents, sunscreens, sunblocks, ultraviolet light absorbers or scattering agents, sunless tanning agents, antioxidants and/or radical scavengers, chelating agents, sequestrants, anti-acne agents, anti-inflammatory agents, anti-androgens, depilation agents, desquamation agents/exfoliants, organic hydroxy acids, vitamins and derivatives thereof, and natural extracts. Such "cosmetic ingredients" are known in the art. Nonexclusive examples of such materials are described in Harry's Cosmeticology, 7th Ed., Harry & Wilkinson (Hill Publishers, London 1982); in Pharmaceutical Dosage Forms—Disperse Systems; Lieberman, Rieger & Banker, Vols. 1 (1988) & 2 (1989); Marcel Decker, Inc.; in The Chemistry and Manufacture of Cosmetics, 2nd. Ed., deNavarre (Van Nostrand 1962-1965); and in The Handbook of Cosmetic Science and Technology, 1st Ed. Knowlton & Pearce (Elsevier 1993).

The term "cultivated", and variants thereof, refer to the intentional fostering of growth (increases in cell size, cellular contents, and/or cellular activity) and/or propagation (increases in cell numbers via mitosis) of one or more cells by use of intended culture conditions. The combination of both growth and propagation may be termed proliferation. The one or more cells may be those of a microorganism, such as microalgae. Examples of intended conditions include the use of a defined medium (with known characteristics such as pH, ionic strength, and carbon source), specified temperature, oxygen tension, carbon dioxide levels, and growth in a bioreactor.

As used herein, the term "cytolysis" refers to the lysis of cells in a hypotonic environment. Cytolysis is caused by excessive osmosis, or movement of water, towards the inside of a cell (hyperhydration). The cell cannot withstand the osmotic pressure of the water inside, and so it explodes.

"Dispersion" refers to a distribution of particles more or less evenly throughout a medium, including a liquid or gas. One common form of dispersion is an emulsion made up of a mixture of two or more immiscible liquids such as oil and water.

As used herein, the terms "dry weight" or "dry cell weight" refer to weight as determined in the relative absence of water. For example, reference to a component of microalgal biomass as comprising a specified percentage by dry weight means that the percentage is calculated based on the weight of the biomass after all or substantially all water has been removed.

"Exogenous gene" refers to a nucleic acid transformed into a cell. A transformed cell may be referred to as a recombinant cell, into which additional exogenous gene(s) may be introduced. The exogenous gene may be from a different species (and so heterologous), or from the same species (and so homologous) relative to the cell being transformed. In the case of a homologous gene, it occupies a different location in the genome of the cell relative to the endogenous copy of the gene. The exogenous gene may be present in more than one copy in the cell. The exogenous gene may be maintained in a cell as an insertion into the genome or as an episomal molecule.

"Exogenously provided" describes a molecule provided to the culture media of a cell culture.

"Fixed carbon source" means molecule(s) containing carbon, preferably organic, that are present at ambient temperature and pressure in solid or liquid form.

"Good Manufacturing Practices" (GMP) refers to the regulations promulgated by the US Food and Drug Association under the authority of Food, Drug and Cosmetics Act that require manufacturers to take precautions to insure that their products are safe, pure and effective. Chapter VI of the FD&C (21 U.S.C. 361) covers regulations related to cosmetics.

"Glycerolipid profile" refers to the distribution of different carbon chain lengths and saturation levels of glycerolipids in a particular sample of biomass or oil. For example, a sample could contain glycerolipids in which approximately 60% of the glycerolipid is C18:1, 20% is C18:0, 15% is C16:0, and 5% is C14:0. In cases in which a carbon length is referenced generically, such as "C:18", such reference can include any amount of saturation; for example, microalgal biomass that contains 20% lipid as C:18 can include C18:0, C18:1, C18:2, and the like, in equal or varying amounts, the sum of which constitute 20% of the biomass.

"Homogenate" means biomass that has been physically disrupted.

"Homogenize" means to blend two or more substances into a homogenous or uniform mixture. In some embodiments, a homogenate is created. In other embodiments, the biomass is predominantly intact, but homogeneously distributed throughout the mixture.

As used herein, the phrase "increase lipid yield" refers to an increase in the productivity of a microbial culture by, for example, increasing dry weight of cells per liter of culture, increasing the percentage of cells that constitute lipid, or increasing the overall amount of lipid per liter of culture volume per unit time.

The term "in situ" means "in place" or "in its original position". For example, a culture may contain a first microalgae secreting a catalyst and a second microorganism secreting a substrate, wherein the first and second cell types produce the components necessary for a particular chemical reaction to occur in situ in the co-culture without requiring further separation or processing of the materials.

"Lipids" are a class of molecules that are soluble in nonpolar solvents (such as ether and hexane) and are relatively or completely insoluble in water. Lipid molecules have these properties because they consist largely of long hydrocarbon tails which are hydrophobic in nature. Examples of lipids include fatty acids (saturated and unsaturated); glycerides or glycerolipids (such as monoglycerides, diglycerides, triglycerides or neutral fats, and phosphoglycerides or glycerophospholipids); nonglycerides (sphingolipids, tocopherols, tocotrienols, sterol lipids including cholesterol and steroid hormones, prenol lipids including terpenoids, fatty alcohols, waxes, and polyketides); and complex lipid derivatives (sugar-linked lipids, or glycolipids, and protein-linked lipids).

As used herein, the term "lysate" refers to a solution containing the contents of lysed cells.

As used herein, the term "lysis" refers to the breakage of the plasma membrane and optionally the cell wall of a biological organism sufficient to release at least some intracellular content, often by mechanical, viral or osmotic mechanisms that compromise its integrity.

As used herein, the term "lysing" refers to disrupting the cellular membrane and optionally the cell wall of a biological organism or cell sufficient to release at least some intracellular content.

"Microalgae" means a eukaryotic microbial organism that contains a chloroplast, and optionally that is capable of performing photosynthesis, or a prokaryotic microbial organism capable of performing photosynthesis. Microalgae include obligate photoautotrophs, which cannot metabolize a fixed carbon source as energy, as well as heterotrophs, which can metabolize a fixed carbon source. Microalgae can refer to unicellular organisms that separate from sister cells shortly after cell division, such as *Chlamydomonas*, and can also refer to microbes such as, for example, *Volvox*, which is a simple multicellular photosynthetic microbe of two distinct cell types. "Microalgae" can also refer to cells such as *Chlorella*, *Dunaliella*, and the like. "Microalgae" also includes other microbial photosynthetic organisms that exhibit cell-cell adhesion, such as *Agmenellum*, *Anabaena*, and *Pyrobotrys*. "Microalgae" also includes obligate heterotrophic microorganisms that have lost the ability to perform photosynthesis and may or may not possess a chloroplast or chloroplast remnant, such as certain dinoflagellate algae species and species of the genus *Prototheca*.

As used herein, "microalgal biomass," "algal biomass" or "biomass" refers to material produced by growth and/or propagation of microalgal cells. Biomass may contain cells and/or intracellular contents as well as extracellular material. Extracellular material includes, but is not limited to, compounds secreted by a cell.

As used herein, "microalgal oil" or "algal oil" refers to lipid components produced by microalgal cells, including triacylglycerols.

The terms "microorganism" and "microbe" are used interchangeably herein to refer to microscopic unicellular organisms.

Unless otherwise indicated by the context in which it is used herein, "oil" means lipid compounds, primarily triacylglycerides, including plants and/or animals. For example, "oil" refers to vegetable or other seed oils derived from plants, including without limitation, an oil derived from soy, rapeseed, canola, palm, palm kernel, coconut, corn, olive, sunflower, cotton seed, cuphea, peanut, camelina sativa, mustard seed, cashew nut, oats, lupine, kenaf, calendula, hemp, coffee, linseed, hazelnut, euphorbia, pumpkin seed, coriander, camellia, sesame, safflower, rice, tung oil tree, cocoa, copra, pium poppy, castor beans, pecan, jojoba, jatropha, macadamia, Brazil nuts, avocado, or combinations thereof.

As used herein, the term "osmotic shock" refers to the rupture of cells in a solution following a sudden reduction in osmotic pressure. Osmotic shock is sometimes induced to release cellular components of such cells into a solution.

"Photobioreactor" refers to a container, at least part of which is at least partially transparent or partially open, thereby allowing light to pass through, in which one or more microalgae cells are cultured. Photobioreactors may be closed, as in the instance of a polyethylene bag or Erlenmeyer flask, or may be open to the environment, as in the instance of an outdoor pond.

As used herein, a "polysaccharide-degrading enzyme" refers to any enzyme capable of catalyzing the hydrolysis, or depolymerization, of any polysaccharide. For example, cellulases catalyze the hydrolysis of cellulose.

"Polysaccharides" (also called "glycans") are carbohydrates made up of monosaccharides joined together by glycosidic linkages. Cellulose is an example of a polysaccharide that makes up certain plant cell walls. Cellulose can be depolymerized by enzymes to yield monosaccharides such as xylose and glucose, as well as larger disaccharides and oligosaccharides.

As used herein, "predominantly intact cells" refers to a population of cells which comprise more than 50%, 75%, or 90% intact cells. "Intact" refers to the physical continuity of the cellular membrane enclosing the intracellular components of the cell and means that the cellular membrane has not been disrupted in any manner that would release the intracellular components of the cell to an extent that exceeds the permeability of the cellular membrane under conventional culture conditions or those culture conditions described herein.

As used herein, the term "sonication" refers to a process of disrupting biological materials, such as a cell, by use of sound wave energy.

Reference to proportions by volume, i.e., "v/v," means the ratio of the volume of one substance or composition to the volume of a second substance or composition. For example, reference to a composition that comprises 5% v/v microalgal oil and at least one other cosmetic ingredient means that 5% of the composition's volume is composed of microalgal oil; e.g., a composition having a volume of 100 $mm^3$ would contain 5 $mm^3$ of microalgal oil and 95 $mm^3$ of other constituents.

Reference to proportions by weight, i.e., "w/w," means the ratio of the weight of one substance or composition to the weight of a second substance or composition. For example, reference to a cosmetic composition that comprises 5% w/w microalgal biomass and at least one other cosmetic ingredient means that 5% of the cosmetic composition is composed of microalgal biomass; e.g., a 100 mg cosmetic composition would contain 5 mg of microalgal biomass and 95 mg of other constituents.

II. Methods for Preparing Microalgal Biomass

Some aspects of the invention are premised in part on the insight that certain microorganisms, and in particular, microalgae, can be used to produce oils and biomass economically for use in the cosmetic industry. Preferred genus of microalgae for use in the invention is the lipid-producing microalgae *Chlorella*. The present application describes methods of culturing *Chlorella* as well as multiple other species of microalgae to generate biomass, particularly high oil content biomass, and algal oils for use in cosmetic products.

A. Microalgae for Use in the Methods of the Invention

Any species of microalgae that produces suitable oils and/or lipids can be used in accordance with the present invention, although microalgae that naturally produce high levels of suitable oils and/or lipids are preferred.

Considerations affecting the selection of microalgae for use in the invention include, in addition to production of suitable oils or lipids for production of cosmetics products: (1) high lipid content as a percentage of cell weight; (2) ease of growth; (3) ease of propagation; (4) ease of biomass processing; (5) glycerolipid profile and (6) lack of algal toxins. Example 22 below illustrates an embodiment of dried microalgae biomass (and oils or lipids extracted from the biomass) that is suitable to be included in cosmetic products because of the lack of algal toxins. In some embodiments, the cell wall of the microalgae must be disrupted during the use of the cosmetic product (e.g., soaps containing whole microalgal cells) in order to release the active components. Hence, in some embodiments having strains of microalgae with cell walls susceptible to disruption are preferred. This criterion is particularly preferred when the algal biomass is to be used as whole algal cells as an ingredient in the final cosmetic production accordance with the present invention. Susceptibility to disruption of the cell wall is generally decreased for microalgal strains which have a high content of cellulose/hemicellulose in the cell walls.

In particular embodiments, the wild-type or genetically engineered microalgae comprise cells that are at least 10%, at least 15%, at least 20%, at least 25%, at least 30%, at least 35%, at least 40%, at least 45%, at least 50%, at least 55%, at least 60%, at least 65%, at least 70%, at least 75%, or at least 80% or more oil by dry weight. Preferred organisms grow heterotrophically (on sugars in the absence of light). Processing considerations can include, for example, the availability of effective means for lysing the cells. It should be noted that not all types of lipids are desirable for use in cosmetics or as cosmetic ingredients, as they may have aesthetic issues, such as smelling bad, having poor stability or providing a poor tactile sensation.

Microalgae from the genus *Chlorella* are generally useful in the methods of the invention. *Chlorella* is a genus of single-celled green algae, belonging to the phylum Chlorophyta. *Chlorella* cells are generally spherical in shape, about 2 to 10 μm in diameter, and lack flagella. Some species of *Chlorella* are naturally heterotrophic. In preferred embodiments, the microalgae used in the methods of the invention is *Chlorella protothecoides, Chlorella ellipsoidea, Chlorella minutissima, Chlorella zofinienesi, Chlorella luteoviridis, Chlorella kessleri, Chlorella sorokiniana, Chlorella fusca* var. *vacuolata Chlorella* sp., *Chlorella cf. minutissima* or *Chlorella emersonii. Chlorella*, particularly *Chlorella protothecoides*, is a preferred microorganism for use in the methods of the invention because of its high composition of lipid. Particularly preferred species of *Chlorella protothecoides* for use in the methods of the invention include those exemplified in the examples below.

Other species of *Chlorella* suitable for use in the methods of the invention include the species selected from the group consisting of *anitrata, Antarctica, aureoviridis, candida, capsulate, desiccate, ellipsoidea* (including strain CCAP 211/42), *emersonii, fusca* (including var. *vacuolata*), *glucotropha, infusionum* (including var. *actophila* and var. *auxenophila*), *kessleri* (including any of UTEX strains 397, 2229,398), *lobophora* (including strain SAG 37.88), *luteoviridis* (including strain SAG 2203 and var. *aureoviridis* and *lutescens*), *miniata, cf. minutissima, minutissima* (including UTEX strain 2341), *mutabilis, nocturna, ovalis, parva, photophila, pringsheimii, protothecoides* (including any of UTEX strains 1806, 411, 264, 256, 255, 250, 249, 31, 29, 25 or CCAP 211/8D, or CCAP 211/17 and var. *acidicola*), *regularis* (including var. *minima*, and *umbricata*), *reisiglii* (including strain CCP 11/8), *saccharophila* (including strain CCAP 211/31, CCAP 211/32 and var. *ellipsoidea*), *salina, simplex, sorokiniana* (including strain SAG 211.40B), sp. (including UTEX strain 2068 and CCAP 211/92), *sphaerica, stigmatophora, trebouxioides, vanniellii, vulgaris* (including strains CCAP 211/11K, CCAP 211/80 and *f. tertia* and var. *autotrophica, viridis, vulgaris, vulgaris f. tertia, vulgaris f. viridis*), *xanthella*, and *zofingiensis*.

Species of *Chlorella* (and species from other microalgae genera) for use in the invention can be identified by comparison of certain target regions of their genome with those same regions of species identified herein; preferred species are those that exhibit identity or at least a very high level of homology with the species identified herein. For example, identification of a specific *Chlorella* species or strain can be achieved through amplification and sequencing of nuclear and/or chloroplast DNA using primers and methodology using appropriate regions of the genome, for example using the methods described in Wu et al., *Bot. Bull. Acad. Sin.* 42:115-121 (2001), Identification of *Chlorella* spp. isolates using ribosomal DNA sequences. Well established methods of phylogenetic analysis, such as amplification and sequencing of ribosomal internal transcribed spacer (ITS1 and ITS2 rDNA), 23S RNA, 18S rRNA, and other conserved genomic regions can be used by those skilled in the art to identify species of not only *Chlorella*, but other oil and lipid producing microalgae suitable for use in the methods disclosed herein. For examples of methods of identification and classification of algae see *Genetics,* 170(4):1601-10 (2005) and *RNA,* 11(4):361-4 (2005).

Thus, genomic DNA comparison can be used to identify suitable species of microalgae to be used in the present invention. Regions of conserved genomic DNA, such as and not limited to DNA encoding for 23S rRNA, can be applied from microalgal species that may be, for example, taxonomically related to the preferred microalgae used in the present invention and compared to the corresponding regions of those preferred species. Species that exhibit a high level of similarity are then selected for use in the methods of the invention. Illustrative examples of such DNA sequence comparison among species within the *Chlo-* rella genus are presented below. In some cases, the microalgae that are preferred for use in the present invention have genomic DNA sequences encoding for 23S rRNA that have at least 65% nucleotide identity to at least one of the sequences listed in SEQ ID NOs:1-23 and 26-27. In other cases, microalgae that are preferred for use in the present invention have genomic DNA sequences encoding for 23S rRNA that have at least 75%, 85%, 90%, 95%, 96%, 97%, 98%, 99% or greater nucleotide identity to at least one or more of the sequences listed in SEQ ID NOs:1-23 and 26-27. Genotyping of a cosmetic composition and/or of algal biomass before it is combined with other ingredients to formulate a cosmetic composition is also a reliable method for determining if algal biomass is from more than a single strain of microalgae.

For sequence comparison to determine percent nucleotide or amino acid identity, typically one sequence acts as a reference sequence, to which test sequences are compared. In applying a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., supra). Another example algorithm that is suitable for determining percent sequence identity and sequence similarity is the BLAST algorithm, which is described in Altschul et al., *J. Mol. Biol.* 215:403-410 (1990). Software for performing BLAST analyses is publicly available through the National Center for Biotechnology Information (at the web address www.ncbi.nlm nih gov).

In addition to *Chlorella*, other genera of microalgae can also be used in the methods of the present invention. In preferred embodiments, the microalgae is a species selected from the group consisting *Parachlorella kessleri, Parachlorella beijerinckii, Neochloris oleabundans, Bracteacoccus*, including *B. grandis, B. cinnabarinas*, and *B. aerius, Bracteococcus* sp. or *Scenedesmus rebescens*. Other nonlimiting examples of microalgae species include those species from the group of species and genera consisting of *Achnanthes orientalis; Agmenellum; Amphiprora hyaline; Amphora*, including *A. coffeiformis* including *A.c. linea, A.c. punctata, A.c. taylori, A.c. tenuis, A.c. delicatissima, A.c. delicatissima capitata; Anabaena; Ankistrodesmus*, including *A. falcatus; Boekelovia hooglandii; Borodinella; Botryococcus braunii*, including *B. sudeticus; Bracteoccocus*, including *B. aerius, B.grandis, B.cinnabarinas, B.minor*, and *B.medionucleatus; Carteria; Chaetoceros*, including *C. gracilis, C. muelleri*, and *C. muelleri subsalsum; Chlorococcum*, including *C. infusionum; Chlorogonium; Chroomonas; Chrysosphaera; Cricosphaera; Cryptheccodinium cohnii; Cryptomonas; Cyclotella*, including *C. cryptica* and *C. meneghiniana; Dunaliella*, including *D. bardawil, D. bioculata, D. granulate, D. maritime, D. minuta, D. parva, D. peircei, D. primolecta, D. salina, D. terricola, D. tertiolecta*, and *D. viridis; Eremosphaera*, including *E. viridis; Ellipsoidon; Euglena; Franceia; Fragilaria*, including *F. crotonensis; Gleocapsa; Gloeothamnion; Hymenomonas; Isochrysis*, including *I. aff. galbana* and *I. galbana; Lepocinclis; Micractinium* (including UTEX LB 2614); *Monoraphidium*, including *M. minutum; Monoraphidium; Nannochloris; Nannochloropsis*, including *N. salina; Navicula*, including *N. acceptata, N. biskanterae, N. pseudotenelloides, N. pelliculosa*, and *N. saprophila; Neochloris oleabundans; Nephrochloris; Nephroselmis; Nitschia communis; Nitzschia*, including *N. alexandrina, N. communis, N. dissipata, N. frustulum, N. hantzschiana, N. inconspicua, N. intermedia, N. microcephala, N. pusilla, N. pusilla elliptica, N. pusilla monoensis*, and *N. quadrangular; Ochromonas; Oocystis*, including *O. parva* and *O. pusilla; Oscillatoria*, including *O. limnetica* and *O. subbrevis; Parachlorella*, including *P. beijerinckii* (including strain SAG 2046) and *P. kessleri* (including any of SAG strains 11.80, 14.82, 21.11H9); *Pascheria*, including *P. acidophila; Pavlova; Phagus; Phormidium; Platymonas; Pleurochrysis*, including *P. carterae* and *P. dentate; Prototheca*, including *P. stagnora* (including UTEX 327), *P. portoricensis*, and *P. moriformis* (including UTEX strains 1441,1435, 1436, 1437, 1439); *Pseudochlorella aquatica; Pyramimonas; Pyrobotrys; Rhodococcus opacus; Sarcinoid chrysophyte; Scenedesmus*, including *S. armatus* and *S. rubescens; Schizochytrium; Spirogyra; Spirulina platensis; Stichococcus; Synechococcus; Tetraedron; Tetraselmis*, including *T. suecica; Thalassiosira weissflogii*; and *Viridiella fridericiana*.

B. Methods of Generating a Microalgae Strain Lacking or that has Significantly Reduced Pigmentation Microalgae, such as *Chlorella*, can be capable of either photosynthetic or heterotrophic growth. When grown in heterotrophic conditions where the carbon source is a fixed carbon source and in the absence of light, the normally green colored microalgae has a yellow color, lacking or is significantly reduced in green pigmentation. Microalgae of reduced (or lacking in) green pigmentation can be advantageous as a cosmetic ingredient. One advantage of microalgae of reduced (or is lacking in) green pigmentation is that as a cosmetic ingredient, the addition of the microalgae to cosmetics will not impart a green color that can be unappealing to the consumer. The reduced green pigmentation of microalgae grown under heterotrophic conditions is transient. When switched back to phototrophic growth, microalgae capable of both phototrophic and heterotrophic growth will regain the green pigmentation. Thus, it is advantageous to generate a microalgae strain that is capable of heterotrophic growth, so it is reduced or lacking in green pigmentation.

In some embodiments, it may be advantageous to reduce the amount of general pigmentation (whether yellow or green). One method for generating such microalgae strain lacking in or has significantly reduced pigmentation is through mutagenesis and then screening for the desired phenotype. Several methods of mutagenesis are known and practiced in the art. For example, Urano et al., (Urano et al., *J Bioscience Bioengineering* (2000) v. 90(5): pp. 567-569) describes yellow and white color mutants of *Chlorella ellipsoidea* generated using UV irradiation. Kamiya (Kamiya, *Plant Cell Physiol.* (1989) v. 30(4): 513-521) describes a colorless strain of *Chlorella vulgaris*, 11h (M125).

In addition to mutagenesis by UV irradiation, chemical mutagenesis can also be employed in order to generate microalgae with reduced (or lacking in) pigmentation.

Chemical mutagens such as ethyl methanesulfonate (EMS) or N-methyl-N'nitro-N-nitroguanidine (NTG) have been shown to be effective chemical mutagens on a variety of microbes including yeast, fungi, mycobacterium and microalgae. Mutagenesis can also be carried out in several rounds, where the microalgae is exposed to the mutagen (either UV or chemical or both) and then screened for the desired reduced pigmentation phenotype. Colonies with the desired phenotype are then streaked out on plates and reisolated to ensure that the mutation is stable from one generation to the next and that the colony is pure and not of a mixed population.

In a particular example, *Chlorella protothecoides* was used to generate strains lacking in or with reduced pigmentation using a combination of UV and chemical mutagenesis. *Chlorella protothecoides* was exposed to a round of chemical mutagenesis with NTG and colonies were screened for color mutants. Colonies not exhibiting color mutations were then subjected to a round of UV irradiation and were again screened for color mutants. In one embodiment, a *Chlorella protothecoides* strain lacking in pigmentation was isolated and is *Chlorella protothecoides* 33-55, deposited on Oct. 13, 2009 at the American Type Culture Collection at 10801 University Boulevard, Manassas, Va. 20110-2209, in accordance with the Budapest Treaty, with a Patent Deposit Designation of PTA-XXXX. In another embodiment, a *Chlorella protothecoides* strain with reduced pigmentation was isolated and is *Chlorella protothecoides* 25-32, deposited on Oct. 13, 2009 at the American Type Culture Collection at 10801 University Boulevard, Manassas, Va. 20110-2209, in accordance with the Budapest Treaty, with a Patent Deposit Designation of PTA-XXXX.

C. Media and Culture Conditions for Microalgae

Microalgae are cultured in liquid media to propagate biomass in accordance with the methods of the invention. In the methods of the invention, microalgal species are grown in a medium containing a fixed carbon and/or fixed nitrogen source in the absence of light. Such growth is known as heterotrophic growth. For some species of microalgae, for example, heterotrophic growth for extended periods of time such as 10 to 15 or more days under limited nitrogen conditions results accumulation of high lipid content in cells.

Microalgal culture media typically contains components such as a fixed carbon source (discussed below), a fixed nitrogen source (such as protein, soybean meal, yeast extract, cornsteep liquor, ammonia (pure or in salt form), nitrate, or nitrate salt), trace elements (for example, zinc, boron, cobalt, copper, manganese, and molybdenum in, e.g., the respective forms of $ZnCl_2$, $H_3BO_3$, $CoCl_2.6H_2O$, $CuCl_2.2H_2O$, $MnCl_2.4H_2O$ and $(NH_4)_6Mo_7O_{24}.4H_2O$), optionally a buffer for pH maintenance, and phosphate (a source of phosphorous; other phosphate salts can be used). Other components include salts such as sodium chloride, particularly for seawater microalgae.

In a particular example, a medium suitable for culturing *Chlorella protothecoides* comprises Proteose Medium. This medium is suitable for axenic cultures, and a 1 L volume of the medium (pH ~6.8) can be prepared by addition of 1 g of proteose peptone to 1 liter of Bristol Medium. Bristol medium comprises 2.94 mM $NaNO_3$, 0.17 mM $CaCl_2.2H_2O$, 0.3 mM $MgSO_4.7H_2O$, 0.43 mM, 1.29 mM $KH_2PO_4$, and 1.43 mM NaCl in an aqueous solution. For 1.5% agar medium, 15 g of agar can be added to 1 L of the solution. The solution is covered and autoclaved, and then stored at a refrigerated temperature prior to use. Other methods for the growth and propagation of *Chlorella protothecoides* to high oil levels as a percentage of dry weight have been described (see for example Miao and Wu, *J. Biotechnology*, 2004, 11:85-93 and Miao and Wu, *Biosource Technology* (2006) 97:841-846 (demonstrating fermentation methods for obtaining 55% oil dry cell weight)). High oil algae can typically be generated by increasing the length of a fermentation while providing an excess of carbon source under nitrogen limitation.

Solid and liquid growth media are generally available from a wide variety of sources, and instructions for the preparation of particular media that is suitable for a wide variety of strains of microorganisms can be found, for example, online at http://www.utex.org/, a site maintained by the University of Texas at Austin for its culture collection of algae (UTEX). For example, various fresh water media include 1/2, 1/3, 1/5, 1×, 2/3, 2×CHEV Diatom Medium; 1:1 DYIII/PEA+Gr+; Ag Diatom Medium; Allen Medium; BG11-1 Medium; Bold 1NV and 3N Medium; *Botryococcus* Medium; Bristol Medium; Chu's Medium; CR1, CR1-S, and CR1+Diatom Medium; Cyanidium Medium; Cyanophycean Medium; Desmid Medium; DYIII Medium; Euglena Medium; HEPES Medium; J Medium; Malt Medium; MES Medium; Modified Bold 3N Medium; Modified COMBO Medium; N/20 Medium; Ochromonas Medium; P49 Medium; Polytomella Medium; Proteose Medium; Snow Algae Media; Soil Extract Medium; Soilwater: BAR, GR–, GR–/NH4, GR+, GR+/NH4, PEA, Peat, and VT Medium; *Spirulina* Medium; Tap Medium; Trebouxia Medium; Volvocacean Medium; Volvocacean-3N Medium; Volvox Medium; Volvox-Dextrose Medium; Waris Medium; and Waris+Soil Extract Medium. Various Salt Water Media include: 1%, 5%, and 1× F/2 Medium; 1/2, 1×, and 2× Erdschreiber's Medium; 1/2, 1/3, 1/4, 1/5, 1×, 5/3, and 2× Soil+Seawater Medium; 1/4 ERD; 2/3 Enriched Seawater Medium; 20% Allen+80% ERD; Artificial Seawater Medium; BG11-1+0.36% NaCl Medium; BG11-1+1% NaCl Medium; Bold 1NV:Erdshreiber (1:1) and (4:1); Bristol-NaCl Medium; Dasycladales Seawater Medium; 1/2 and 1× Enriched Seawater Medium, including ES/10, ES/2, and ES/4; F/2+NH4; LDM Medium; Modified 1× and 2×CHEV; Modified 2×CHEV+Soil; Modified Artificial Seawater Medium; Porphridium Medium; and SS Diatom Medium.

Other suitable media for use with the methods of the invention can be readily identified by consulting the URL identified above, or by consulting other organizations that maintain cultures of microorganisms, such as SAG, CCAP, or CCALA. SAG refers to the Culture Collection of Algae at the University of Göttingen (Göttingen, Germany), CCAP refers to the culture collection of algae and protozoa managed by the Scottish Association for Marine Science (Scotland, United Kingdom), and CCALA refers to the culture collection of algal laboratory at the Institute of Botany (Třeboň, Czech Republic).

Microorganisms useful in accordance with the methods of the present invention are found in various locations and environments throughout the world. As a consequence of their isolation from other species and their resulting evolutionary divergence, the particular growth medium for optimal growth and generation of oil and/or lipid and/or protein from any particular species of microbe can be difficult or impossible to predict, but those of skill in the art can readily find appropriate media by routine testing in view of the disclosure herein. In some cases, certain strains of microorganisms may be unable to grow on a particular growth medium because of the presence of some inhibitory component or the absence of some essential nutritional requirement required by the particular strain of microorganism. The examples below provide exemplary methods of culturing various species of microalgae to accumulate high levels of lipid as a percentage of dry cell weight.

The fixed carbon source is a key component of the medium. Suitable fixed carbon sources for purposes of the present invention, include, for example, glucose, fructose, sucrose, galactose, xylose, mannose, rhamnose, arabinose, N-acetylglucosamine, glycerol, floridoside, glucuronic acid, and/or acetate.

High lipid biomass from microalgae is an advantageous material for inclusion in cosmetic products compared to low lipid biomass, because it allows for the addition of less microalgal biomass to incorporate the same amount of lipid into a cosmetic composition. Process conditions can be adjusted to increase the percentage weight of cells that is lipid. For example, in certain embodiments, a microalgae is cultured in the presence of a limiting concentration of one or more nutrients, such as, for example, nitrogen, phosphorous, or sulfur, while providing an excess of a fixed carbon source, such as glucose. Nitrogen limitation tends to increase microbial lipid yield over microbial lipid yield in a culture in which nitrogen is provided in excess. In particular embodiments, the increase in lipid yield is at least about 10%, 50%, 100%, 200%, or 500%. The microbe can be cultured in the presence of a limiting amount of a nutrient for a portion of the total culture period or for the entire period. In some embodiments, the nutrient concentration is cycled between a limiting concentration and a non-limiting concentration at least twice during the total culture period.

In a steady growth state, the cells accumulate oil but do not undergo cell division. In one embodiment of the invention, the growth state is maintained by continuing to provide all components of the original growth media to the cells with the exception of a fixed nitrogen source. Cultivating microalgal cells by feeding all nutrients originally provided to the cells except a fixed nitrogen source, such as through feeding the cells for an extended period of time, results in a higher percentage of lipid by dry cell weight.

In other embodiments, high lipid biomass is generated by feeding a fixed carbon source to the cells after all fixed nitrogen has been consumed for extended periods of time, such as at least one or two weeks. In some embodiments, cells are allowed to accumulate oil in the presence of a fixed carbon source and in the absence of a fixed nitrogen source for over 20 days. Microalgae grown using conditions described herein or otherwise known in the art can comprise at least about 20% lipid by dry weight, and often comprise 35%, 45%, 55%, 65%, and even 75% or more lipid by dry weight. Percentage of dry cell weight as lipid in microbial lipid production can therefore be improved by holding cells in a heterotrophic growth state in which they consume carbon and accumulate oil but do not undergo cell division.

High protein biomass from algae is another advantageous material for inclusion in cosmetic products. The methods of the invention can also provide biomass that has at least 30% of its dry cell weight as protein. Growth conditions can be adjusted to increase the percentage weight of cells that is protein. In a preferred embodiment, a microalgae is cultured in a nitrogen rich environment and an excess of fixed carbon energy such as glucose or any of the other carbon sources discussed above. Conditions in which nitrogen is in excess tends to increase microbial protein yield over microbial protein yield in a culture in which nitrogen is not provided in excess. For maximal protein production, the microbe is preferably cultured in the presence of excess nitrogen for the total culture period. Suitable nitrogen sources for microalgae may come from organic nitrogen sources and/or inorganic nitrogen sources.

Organic nitrogen sources have been used in microbial cultures since the early 1900s. The use of organic nitrogen sources, such as corn steep liquor was popularized with the production of penicillin from mold. Researchers found that the inclusion of corn steep liquor in the culture medium increased the growth of the microoranism and resulted in an increased yield in products (such as penicillin). An analysis of corn steep liquor determined that it was a rich source of nitrogen and also vitamins such as B-complex vitamins, riboflavin panthothenic acid, niacin, inositol and nutrient minerals such as calcium, iron, magnesium, phosphorus and potassium (Ligget and Koffler, *Bacteriological Reviews* (1948); 12(4): 297-311). Organic nitrogen sources, such as corn steep liquor, have been used in fermentation media for yeasts, bacteria, fungi and other microorganisms. Non-limiting examples of organic nitrogen sources are yeast extract, peptone, corn steep liquor and corn steep powder. Non-limiting examples of preferred inorganic nitrogen sources include, for example, and without limitation, $(NH_4)_2SO_4$ and $NH_4OH$. In one embodiment, the culture media for carrying out the invention contains only inorganic nitrogen sources. In another embodiment, the culture media for carrying out the invention contains only organic nitrogen sources. In yet another embodiment, the culture media for carrying out the invention contains a mixture of organic and inorganic nitrogen sources.

In the methods of the invention, a bioreactor or fermentor is used to culture microalgal cells through the various phases of their physiological cycle. As an example, an inoculum of lipid-producing microalgal cells is introduced into the medium; there is a lag period (lag phase) before the cells begin to propagate. Following the lag period, the propagation rate increases steadily and enters the log, or exponential, phase. The exponential phase is in turn followed by a slowing of propagation due to decreases in nutrients such as nitrogen, increases in toxic substances, and quorum sensing mechanisms. After this slowing, propagation stops, and the cells enter a stationary phase or steady growth state, depending on the particular environment provided to the cells. For obtaining protein rich biomass, the culture is typically harvested during or shortly after then end of the exponential phase. For obtaining lipid rich biomass, the culture is typically harvested well after then end of the exponential phase, which may be terminated early by allowing nitrogen or another key nutrient (other than carbon) to become depleted, forcing the cells to convert the carbon sources, present in excess, to lipid. Culture condition parameters can be manipulated to optimize total oil production, the combination of lipid species produced, and/or production of a specific oil.

Bioreactors offer many advantages for use in heterotrophic growth and propagation methods. As will be appreciated, provisions made to make light available to the cells in photosynthetic growth methods are unnecessary when using a fixed-carbon source in the heterotrophic growth and propagation methods described herein. To produce biomass for use in cosmetics, microalgae are preferably fermented in large quantities in liquid, such as in suspension cultures as an example. Bioreactors such as steel fermentors (5000 liter, 10,000 liter, 40,000 liter, and higher are used in various embodiments of the invention) can accommodate very large culture volumes. Bioreactors also typically allow for the control of culture conditions such as temperature, pH, oxygen tension, and carbon dioxide levels. For example, bioreactors are typically configurable, for example, using ports attached to tubing, to allow gaseous components, like oxygen or nitrogen, to be bubbled through a liquid culture.

Bioreactors can be configured to flow culture media though the bioreactor throughout the time period during which the microalgae reproduce and increase in number. In some embodiments, for example, media can be infused into the bioreactor after inoculation but before the cells reach a desired density. In other instances, a bioreactor is filled with culture media at the beginning of a culture, and no more culture media is infused after the culture is inoculated. In other words, the microalgal biomass is cultured in an aqueous medium for a period of time during which the microalgae reproduce and increase in number; however, quantities of aqueous culture medium are not flowed through the bioreactor throughout the time period. Thus in some embodiments, aqueous culture medium is not flowed through the bioreactor after inoculation.

Bioreactors equipped with devices such as spinning blades and impellers, rocking mechanisms, stir bars, means for pressurized gas infusion can be used to subject microalgal cultures to mixing. Mixing may be continuous or intermittent. For example, in some embodiments, a turbulent flow regime of gas entry and media entry is not maintained for reproduction of microalgae until a desired increase in number of said microalgae has been achieved.

As briefly mentioned above, bioreactors are often equipped with various ports that, for example, allow the gas content of the culture of microalgae to be manipulated. To illustrate, part of the volume of a bioreactor can be gas rather than liquid, and the gas inlets of the bioreactor to allow pumping of gases into the bioreactor. Gases that can be beneficially pumped into a bioreactor include air, air/$CO_2$ mixtures, noble gases, such as argon, and other gases. Bioreactors are typically equipped to enable the user to control the rate of entry of a gas into the bioreactor. As noted above, increasing gas flow into a bioreactor can be used to increase mixing of the culture.

Increased gas flow affects the turbidity of the culture as well. Turbulence can be achieved by placing a gas entry port below the level of the aqueous culture media so that gas entering the bioreactor bubbles to the surface of the culture. One or more gas exit ports allow gas to escape, thereby preventing pressure buildup in the bioreactor. Preferably a gas exit port leads to a "one-way" valve that prevents contaminating microorganisms from entering the bioreactor.

The specific examples of bioreactors, culture conditions, and heterotrophic growth and propagation methods described herein can be combined in any suitable manner to improve efficiencies of microbial growth and lipid and/or protein production.

D. Concentration of Microalgae After Fermentation

Microalgal cultures generated according to the methods described above yield microalgal biomass in fermentation media. To prepare the biomass for use as a cosmetic composition, the biomass is concentrated, or harvested, from the fermentation medium. At the point of harvesting the microalgal biomass from the fermentation medium, the biomass comprises predominantly intact cells suspended in an aqueous culture medium. To concentrate the biomass, a dewatering step is performed. Dewatering or concentrating refers to the separation of the biomass from fermentation broth or other liquid medium and so is solid-liquid separation. Thus, during dewatering, the culture medium is removed from the biomass (for example, by draining the fermentation broth through a filter that retains the biomass), or the biomass is otherwise removed from the culture medium. Common processes for dewatering include centrifugation, filtration, and the use of mechanical pressure. These processes can be used individually or in any combination.

Centrifugation involves the use of centrifugal force to separate mixtures. During centrifugation, the more dense components of the mixture migrate away from the axis of the centrifuge, while the less dense components of the mixture migrate towards the axis. By increasing the effective gravitational force (i.e., by increasing the centrifugation speed), more dense material, such as solids, separate from the less dense material, such as liquids, and so separate out according to density. Centrifugation of biomass and broth or other aqueous solution forms a concentrated paste comprising the microalgal cells. Centrifugation does not remove significant amounts of intracellular water. In fact, after centrifugation, there may still be a substantial amount of surface or free moisture in the biomass (e.g., upwards of 70%), so centrifugation is not considered to be a drying step.

Filtration can also be used for dewatering. One example of filtration that is suitable for the present invention is tangential flow filtration (TFF), also known as cross-flow filtration. Tangential flow filtration is a separation technique that uses membrane systems and flow force to separate solids from liquids. For an illustrative suitable filtration method, see Geresh, Carb. Polym. 50; 183-189 (2002), which describes the use of a MaxCell A/G Technologies 0.45 uM hollow fiber filter. Also see, for example, Millipore Pellicon® devices, used with 100 kD, 300 kD, 1000 kD (catalog number P2C01MC01), 0.1 uM (catalog number P2VVPPV01), 0.22 uM (catalog number P2GVPPV01), and 0.45 uM membranes (catalog number P2HVMPV01). The retentate preferably does not pass through the filter at a significant level, and the product in the retentate preferably does not adhere to the filter material. TFF can also be performed using hollow fiber filtration systems. Filters with a pore size of at least about 0.1 micrometer, for example about 0.12, 0.14, 0.16, 0.18, 0.2, 0.22, 0.45, or at least about 0.65 micrometers, are suitable. Preferred pore sizes of TFF allow solutes and debris in the fermentation broth to flow through, but not microbial cells.

Dewatering can also be affected with mechanical pressure directly applied to the biomass to separate the liquid fermentation broth from the microbial biomass sufficient to dewater the biomass but not to cause predominant lysis of cells. Mechanical pressure to dewater microbial biomass can be applied using, for example, a belt filter press. A belt filter press is a dewatering device that applies mechanical pressure to a slurry (e.g., microbial biomass taken directly from the fermentor or bioreactor) that is passed between the two tensioned belts through a serpentine of decreasing diameter rolls. The belt filter press can actually be divided into three zones: the gravity zone, where free draining water/liquid is drained by gravity through a porous belt; a wedge zone, where the solids are prepared for pressure application; and a pressure zone, where adjustable pressure is applied to the gravity drained solids.

After concentration, microalgal biomass can be processed, as described hereinbelow, to produce vacuum-packed cake, algal flakes, algal homogenate, algal powder, algal flour, or algal oil.

E. Chemical Composition of Microalgal Biomass

The microalgal biomass generated by the culture methods described herein comprises microalgal oil and/or protein as well as other constituents generated by the microorganisms or incorporated by the microorganisms from the culture medium during fermentation.

Microalgal biomass with a high percentage of oil/lipid accumulation by dry weight has been generated using different methods of culture, including methods known in the art. Microalgal biomass with a higher percentage of accumulated oil/lipid is useful in accordance with the present invention. *Chlorella vulgaris* cultures with up to 56.6% lipid by dry cell weight (DCW) in stationary cultures grown under autotrophic conditions using high iron (Fe) concentrations have been described (Li et al., *Bioresource Technology* 99(11):4717-22 (2008). *Nanochloropsis* sp. and *Chaetoceros calcitrans* cultures with 60% lipid by DCW and 39.8% lipid by DCW, respectively, grown in a photobioreactor under nitrogen starvation conditions have also been described (Rodolfi et al., *Biotechnology & Bioengineering* (2008)). *Parietochloris incise* cultures with approximately 30% lipid by DCW when grown phototropically and under low nitrogen condtions have been described (Solovchenko et al., *Journal of Applied Phycology* 20:245-251 (2008). *Chlorella protothecoides* can produce up to 55% lipid by DCW when grown under certain heterotrophic conditions with nitrogen starvation (Miao and Wu, *Bioresource Technology* 97:841-846 (2006)). Other *Chlorella* species, including *Chlorella emersonii, Chlorella sorokiniana* and *Chlorella minutissima* have been described to have accumulated up to 63% oil by DCW when grown in stirred tank bioreactors under low-nitrogen media conditions (Illman et al., *Enzyme and Microbial Technology* 27:631-635 (2000). Still higher percent lipid by DCW has been reported, including 70% lipid in *Dumaliella tertiolecta* cultures grown in increased NaCl conditions (Takagi et al., *Journal of Bioscience and Bioengineering* 101(3): 223-226 (2006)) and 75% lipid in *Botryococcus braunii* cultures (Banerjee et al., *Critical Reviews in Biotechnology* 22(3): 245-279 (2002)).

Heterotrophic growth results in relatively low chlorophyll content (as compared to phototrophic systems such as open ponds or closed photobioreactor systems). The reduced chlorophyll content found in heterotrophically grown microalgae (e.g., *Chlorella*) also reduces the green color in the biomass as compared to phototrophically grown microalgae. Thus, the reduced chlorophyll content avoids an often undesired green coloring associated with cosmetic products containing phototrophically grown microalgae and allows for the incorporation or an increased incorporation of algal biomass into a cosmetic product. In at least one embodiment, the cosmetic product contains heterotrophically grown microalgae of reduced chlorophyll content compared to phototrophically grown microalgae.

Oil rich microalgal biomass generated by the culture methods described herein and useful in accordance with the present invention comprises at least 10% microalgal oil by DCW. In some embodiments, the microalgal biomass comprises at least 15%, 25%, 50%, 75% or at least 90% microalgal oil by DCW.

The microalgal oil of the biomass described herein (or extracted from the biomass) can comprise glycerolipids with one or more distinct fatty acid ester side chains Glycerolipids are comprised of a glycerol molecule esterified to one, two, or three fatty acid molecules, which can be of varying lengths and have varying degrees of saturation. Specific blends of algal oil can be prepared either within a single species of algae, or by mixing together the biomass (or algal oil) from two or more species of microalgae.

Thus, the oil composition, i.e., the properties and proportions of the fatty acid constituents of the glycerolipids, can also be manipulated by combining biomass (or oil) from at least two distinct species of microalgae. In some embodiments, at least two of the distinct species of microalgae have different glycerolipid profiles. The distinct species of microalgae can be cultured together or separately as described herein, preferably under heterotrophic conditions, to generate the respective oils. Different species of microalgae can contain different percentages of distinct fatty acid constituents in the cell's glycerolipids.

In some embodiments, the microalgal oil is primarily comprised of monounsaturated oil. In some cases, the algal oil is at least 20% monounsaturated oil by weight. In various embodiments, the algal oil is at least 25%, 50%, 75% or more monounsaturated oil by weight or by volume. In some embodiments, the monounsaturated oil is 18:1, 16:1, 14:1 or 12:1. In some embodiments, the microalgal oil comprises at least 10%, 20%, 25%, or 50% or more esterified oleic acid or esterified alpha-linolenic acid by weight of by volume. In at least one embodiment, the algal oil comprises less than 10%, less than 5%, less than 3%, less than 2%, or less than 1% by weight or by volume, or is substantially free of, esterified docosahexanoic acid (DHA (22:6)). For examples of production of high DHA-containing microalgae, such as in *Crypthecodinium cohnii*, see U.S. Pat. Nos. 7,252,979, 6,812,009 and 6,372,460.

High protein microalgal biomass has been generated using different methods of culture. Microalgal biomass with a higher percentage of protein content is useful in accordance with the present invention. For example, the protein content of various species of microalgae has been reported (see Table 1 of Becker, *Biotechnology Advances* (2007) 25:207-210). Controlling the renewal rate in a semi-continous photoautotrophic culture of *Tetraselmis suecica* has been reported to affect the protein content per cell, the highest being approximately 22.8% protein (Fabregas, et al., *Marine Biotechnology* (2001) 3:256-263).

Microalgal biomass generated by culture methods described herein and useful in accordance to those embodiments of the present invention relating to high protein typically comprises at least 30% protein by dry cell weight. In some embodiments, the microalgal biomass comprises at least 40%, 50%, 75% or more protein by dry cell weight. In some embodiments, the microalgal biomass comprises from 30-75% protein by dry cell weight or from 40-60% protein by dry cell weight. In some embodiments, the protein in the microalgal biomass comprises at least 40% digestible crude protein. In other embodiments, the protein in the microalgal biomass comprises at least 50%, 60%, 70%, 80%, or at least 90% digestible crude protein. In some embodiments, the protein in the microalgal biomass comprises from 40-90% digestible crude protein, from 50-80% digestible crude protein, or from 60-75% digestible crude protein.

Microalgal biomass (and oil extracted therefrom), can also include other constituents produced by the microalgae, or incorporated into the biomass from the culture medium. These other constituents can be present in varying amounts depending on the culture conditions used and the species of microalgae (and, if applicable, the extraction method used to recover microalgal oil from the biomass). The other constituents can include, without limitation, phospholipids (e.g., algal lecithin), carbohydrates, soluble and insoluble fiber, glycoproteins, phytosterols (e.g., β-sitosterol, campesterol, stigmasterol, ergosterol, and brassicasterol), tocopherols, tocotrienols, carotenoids (e.g., α-carotene, β-carotene, and lycopene), xanthophylls (e.g., lutein, zeaxanthin, α-cryptoxanthin, and β-cryptoxanthin), proteins, polysaccharides (e.g., arabinose, mannose, galactose, 6-methyl galactose and glucose) and various organic or inorganic compounds (e.g., selenium).

In some cases, the biomass comprises at least 10 ppm selenium. In some cases, the biomass comprises at least 25% w/w algal polysaccharide. In some cases, the biomass comprises at least 15% w/w algal glycoprotein. In some cases, the biomass comprises between 0-115 mcg/g total carotenoids. In some cases, the biomass comprises at least 0.5% algal phospholipids. In some cases, the oil derived from the algal biomass contains at least 0.10 mg/g total tocotrienols. In some cases, the oil derived from the algal biomass contains between 0.125 mg/g to 0.35 mg/g total tocotrienols. In some cases, the oil derived from the algal biomass contains at least 5.0 mg/100 g total tocopherols. In some cases, the oil derived from the algal biomass contains between 5.0 mg/100 g to 10 mg/100 g tocopherols. A detailed description of tocotrienols and tocopherols composition in *Chlorella protothecoides* is included in the Examples below.

III. Processing Microalgal Biomass into Finished Cosmetic Ingredients

The concentrated microalgal biomass produced in accordance with the methods of the invention is itself a finished cosmetic ingredient and may be used in cosmetics without further, or with only minimal, modification. For example, the cake can be vacuum-packed or frozen. Alternatively, the biomass may be dried via lyophilization, a "freeze-drying" process, in which the biomass is frozen in a freeze-drying chamber to which a vacuum is applied. The application of a vacuum to the freeze-drying chamber results in sublimation (primary drying) and desorption (secondary drying) of the water from the biomass. However, the present invention provides a variety of microalgal derived finished cosmetic ingredients with enhanced properties resulting from processing methods of the invention that can be applied to the concentrated microalgal biomass.

Drying the microalgal biomass, either predominantly intact or in homogenate form, is advantageous to facilitate further processing or for use of the biomass in the methods and compositions described herein. Drying refers to the removal of free or surface moisture/water from predominantly intact biomass or the removal of surface water from a slurry of homogenized (e.g., by micronization) biomass. Different textures and dispersion properties can be conferred on cosmetic products depending on whether the algal biomass is dried, and if so, the drying method. Drying the biomass generated from the cultured microalgae described herein removes water that may be an undesirable component of finished cosmetic products or cosmetic ingredients. In some cases, drying the biomass may facilitate a more efficient microalgal oil extraction process.

In one embodiment, the concentrated microalgal biomass is drum dried to a flake form to produce algal flake, as described in part A of this section. In another embodiment, the concentrated micralgal biomass is spray or flash dried (i.e., subjected to a pneumatic drying process) to form a powder containing predominantly intact cells to produce algal powder, as described in part B of this section. In another embodiment, oil is extracted from the concentrated microalgal biomass to form algal oil, as described in part C of this section.

A. Algal Flake

Algal flake of the invention is prepared from concentrated microalgal biomass that is applied as a film to the surface of a rolling, heated drum. The dried solids are then scraped off with a knife or blade, resulting in a small flakes. U.S. Pat. No. 6,607,900 describes drying microalgal biomass using a drum dryer without a prior centrifugation (concentration) step, and such a process may be used in accordance with the methods of the invention.

Because the biomass may be exposed to high heat during the drying process, it may be advantageous to add an antioxidant to the biomass prior to drying. The addition of an antioxidant will not only protect the biomass during drying, but also extend the shelf-life of the dried microalgal biomass when stored. In a preferred embodiment, an antioxidant is added to the microalgal biomass prior to subsequent processing such as drying or homogenization. Antioxidants that are suitable for use are discussed in detail below.

Additionally, if there is significant time between the production of the dewatered microalgal biomass and subsequent processing steps, it may be advantageous to pasteurize the biomass prior to drying. Free fatty acids from lipases may form if there is significant time between producing and drying the biomass. In one embodiment, the pasteurized microalgal biomass is an algal flake.

B. Algal Powder

Algal powder of the invention is prepared from concentrated microalgal biomass using a pneumatic or spray dryer (see for example U.S. Pat. No. 6,372,460). In a spray dryer, material in a liquid suspension is sprayed in a fine droplet dispersion into a current of heated air. The entrained material is rapidly dried and forms a dry powder. In some cases, a pulse combustion dryer can also be used to achieve a powdery texture in the final dried material. In other cases, a combination of spray drying followed by the use of a fluid bed dryer is used to achieve the optimal conditions for dried microbial biomass (see, for example, U.S. Pat. No. 6,255,505). As an alternative, pneumatic dryers can also be used in the production of algal powder. Pneumatic dryers draw or entrain the material that is to be dried in a stream of hot air. While the material is entrained in the hot air, the moisture is rapidly removed. The dried material is then separated from the moist air and the moist air is then recirculated for further drying.

C. Algal Flour

Algal flour of the invention is prepared from concentrated microalgal biomass that has been mechanically lysed and homogenized and the homogenate spray or flash dried (or dried using another pneumatic drying system). The production of algal flour requires that cells be lysed to release their oil and that cell wall and intracellular components be micronized or reduced in particle size to an average size of no more than 10 μm. The resulting oil, water, and micronized particles are emulsified such that the oil does not separate from the dispersion prior to drying. For example, a pressure disrupter can be used to pump a cell containing slurry through a restricted orifice valve to lyse the cells. High pressure (up to 1500 bar) is applied, followed by an instant expansion through an exiting nozzle. Cell disruption is accomplished by three different mechanisms: impingement on the valve, high liquid shear in the orifice, and sudden pressure drop upon discharge, causing an explosion of the cell. The method releases intracellular molecules. A Niro (Niro Soavi GEA) homogenizer (or any other high pressure homogenizer) can be used to process cells to particles predominantly 0.2 to 5 microns in length. Processing of algal biomass under high pressure (approximately 1000 bar) typically lyses over 90% of the cells and reduces particle size to less than 5 microns.

Alternatively, a ball mill can be used. In a ball mill, cells are agitated in suspension with small abrasive particles, such as beads. Cells break because of shear forces, grinding between beads, and collisions with beads. The beads disrupt the cells to release cellular contents. In one embodiment, algal biomass is disrupted and formed into a stable emulsion using a Dyno-mill ECM Ultra (CB Mills) ball mill Cells can also be disrupted by shear forces, such as with the use of blending (such as with a high speed or Waring blender as examples), the french press, or even centrifugation in case of weak cell walls, to disrupt cells. A suitable ball mill including specifics of ball size and blade is described in U.S. Pat. No. 5,330,913.

The immediate product of homogenization is a slurry of particles smaller in size than the original cells that is suspended in in oil and water. The particles represent cellular debris. The oil and water are released by the cells. Additional water may be contributed by aqueous media containing the cells before homogenization. The particles are preferably in the form of a micronized homogenate. If left to stand, some of the smaller particles may coalesce. However, an even dispersion of small particles can be preserved by seeding with a microcrystalline stabilizer, such as microcrystalline cellulose.

To form the algal flour, the slurry is spray or flash dried, removing water and leaving a dry power containing cellular debris and oil. Although the oil content of the powder can be at least 10, 25 or 50% by weight of the dry powder, the powder can have a dry rather than greasy feel and appearance (e.g., lacking visible oil) and can also flow freely when shaken. Various flow agents (including silica-derived products) can also be added. After drying, the water or moisture content of the powder is typically less than 10%, 5%, 3% or 1% by weight. Other dryers such as pneumatic dryers or pulse combustion dryers can also be used to produce algal flour.

The oil content of algal flour can vary depending on the percent oil of the algal biomass. Algal flour can be produced from algal biomass of varying oil content. In certain embodiments, the algal flour is produced from algal biomass of the same oil content. In other embodiments, the algal flour is produced from alglal biomass of different oil content. In the latter case, algal biomass of varying oil content can be combined and then the homogenization step performed. In other embodiments, algal flour of varying oil content is produced first and then blended together in various proportions in order to achieve an algal flour product that contains the final desired oil content. In a further embodiment, algal biomass of different lipid profiles can be combined together and then homogenized to produce algal flour. In another embodiment, algal flour of different lipid profiles is produced first and then blended together in various proportions in order to achieve an algal flour product that contains the final desired lipid profile.

D. Algal Oil

In one aspect, the present invention is directed to a method of preparing algal oil by harvesting algal oil from an algal biomass comprising at least 15% oil by dry weight under GMP conditions, in which the algal oil is greater than 50% 18:1 lipid. In some cases, the algal biomass comprises a mixture of at least two distinct species of microalgae. In some cases, at least two of the distinct species of microalgae have been separately cultured. In at least one embodiment, at least two of the distinct species of microalgae have different glycerolipid profiles. In some cases, the algal biomass is derived from algae grown heterotrophically. In some cases, all of the at least two distinct species of microalgae contain at least 15% oil by dry weight.

In one aspect, the present invention is directed to a method of making a cosmetic composition comprising combining algal oil obtained from algal cells containing at least 10%, or at least 15% oil by dry weight with one or more other ingredients to form the cosmetic composition. In some cases, the method further comprises preparing the algal oil under GMP conditions.

Algal oil can be separated from lysed biomass for use in cosmetic products (among other applications). The algal biomass remaining after oil extraction is referred to as delipidated meal. Delipidated meal contains less oil by dry weight or volume than the microalgae contained before extraction. Typically 50-90% of oil is extracted so that delipidated meal contains, for example, 10-50% of the oil content of biomass before extraction. However, the biomass still has a high nutrient value in content of protein and other constituents discussed above. Thus, the delipidated meal can be used in animal feed or in human food applications.

In some embodiments of the method, the algal oil is at least 50% w/w oleic acid and contains less than 5% DHA. In some embodiments of the method, the algal oil is at least 50% w/w oleic acid and contains less than 0.5% DHA. In some embodiments of the method, the algal oil is at least 50% w/w oleic acid and contains less than 5% glycerolipid containing carbon chain length greater than 18. In some cases, the algal cells from which the algal oil is obtained comprise a mixture of cells from at least two distinct species of microalgae. In some cases, at least two of the distinct species of microalgae have been separately cultured. In at least one embodiment, at least two of the distinct species of microalgae have different glycerolipid profiles. In some cases, the algal cells are cultured under heterotrophic conditions. In some cases, all of the at least two distinct species of microalgae contain at least 10%, or at least 15% oil by dry weight.

In one aspect, the present invention is directed to algal oil containing at least 50% monounsaturated oil and containing less than 1% DHA prepared under GMP conditions. In some cases, the monounsaturated oil is 18:1 lipid. In some cases, the algal oil is packaged in a capsule for delivery of a unit dose of oil. In some cases, the algal oil is derived from a mixture of at least two distinct species of microalgae. In some cases, at least two of the distinct species of microalgae have been separately cultured. In at least one embodiment, at least two of the distinct species of microalgae have different glycerolipid profiles. In some cases, the algal oil is derived from algal cells cultured under heterotrophic conditions.

In one aspect, the present invention is directed to oil comprising greater than 60% 18:1, and at least 0.20 mg/g tocotrienol.

In one aspect, the present invention is directed to a fatty acid alkyl ester composition comprising greater than 60% 18:1 ester, and at least 0.20 mg/g tocotrienol.

Algal oil of the invention is prepared from concentrated, washed microalgal biomass by extraction. The cells in the biomass are lysed prior to extraction. Optionally, the microbial biomass may also be dried (oven dried, lyophilized, etc.) prior to lysis (cell disruption). Alternatively, cells can be lysed without separation from some or all of the fermentation broth when the fermentation is complete. For example, the cells can be at a ratio of less than 1:1 v:v cells to extracellular liquid when the cells are lysed.

Microalgae containing lipids can be lysed to produce a lysate. As detailed herein, the step of lysing a microorganism (also referred to as cell lysis) can be achieved by any convenient means, including heat-induced lysis, adding a base, adding an acid, using enzymes such as proteases and polysaccharide degradation enzymes such as amylases, using ultrasound, mechanical pressure-based lysis, and lysis using osmotic shock. Each of these methods for lysing a microorganism can be used as a single method or in combination simultaneously or sequentially. The extent of cell disruption can be observed by microscopic analysis. Using one or more of the methods above, typically more than 70% cell breakage is observed. Preferably, cell breakage is more than 80%, more preferably more than 90% and most preferred about 100%.

Lipids and oils generated by the microalgae in accordance with the present invention can be recovered by extraction. In some cases, extraction can be performed using an organic solvent or an oil, or can be performed using a solventless-extraction procedure.

For organic solvent extraction of the microalgal oil, the preferred organic solvent is hexane. Typically, the organic solvent is added directly to the lysate without prior separation of the lysate components. In one embodiment, the lysate generated by one or more of the methods described above is contacted with an organic solvent for a period of time sufficient to allow the lipid components to form a solution with the organic solvent. In some cases, the solution can then be further refined to recover specific desired lipid components. The mixture can then be filtered and the hexane removed by, for example, rotoevaporation. Hexane extraction methods are well known in the art. See, e.g., Frenz et al., *Enzyme Microb. Technol.*, 11:717 (1989).

Miao and Wu describe a protocol of the recovery of microalgal lipid from a culture of *Chlorella protothecoides* in which the cells were harvested by centrifugation, washed with distilled water and dried by freeze drying. The resulting cell powder was pulverized in a mortar and then extracted with n-hexane. Miao and Wu, *Biosource Technology* 97:841-846 (2006).

In some cases, microalgal oils can be extracted using liquefaction (see for example Sawayama et al., *Biomass and Bioenergy* 17:33-39 (1999) and Inoue et al., *Biomass Bioenergy* 6(4):269-274 (1993)); oil liquefaction (see for example Minowa et al., *Fuel* 74(12):1735-1738 (1995)); or supercritical $CO_2$ extraction (see for example Mendes et al., *Inorganica Chimica Acta* 356:328-334 (2003)).

Oil extraction includes the addition of an oil directly to a lysate without prior separation of the lysate components. After addition of the oil, the lysate separates either of its own accord or as a result of centrifugation or the like into different layers. The layers can include in order of decreasing density: a pellet of heavy solids, an aqueous phase, an emulsion phase, and an oil phase. The emulsion phase is an emulsion of lipids and aqueous phase. Depending on the percentage of oil added with respect to the lysate (w/w or v/v), the force of centrifugation if any, volume of aqueous media and other factors, either or both of the emulsion and oil phases can be present. Incubation or treatment of the cell lysate or the emulsion phase with the oil is performed for a time sufficient to allow the lipid produced by the microorganism to become solubilized in the oil to form a heterogeneous mixture.

In various embodiments, the oil used in the extraction process is selected from the group consisting of oil from soy, rapeseed, canola, palm, palm kernel, coconut, corn, waste vegetable oil, Chinese tallow, olive, sunflower, cotton seed, chicken fat, beef tallow, porcine tallow, microalgae, macroalgae, *Cuphea*, flax, peanut, choice white grease (lard), *Camelina sativa* mustard seedcashew nut, oats, lupine, kenaf, calendula, hemp, coffee, linseed, hazelnut, euphorbia, pumpkin seed, coriander, camellia, sesame, safflower, rice, tung oil tree, cocoa, copra, pium poppy, castor beans, pecan, jojoba, jatropha, macadamia, Brazil nuts, and avocado. The amount of oil added to the lysate is typically greater than 5% (measured by v/v and/or w/w) of the lysate with which the oil is being combined. Thus, a preferred v/v or w/w of the oil is greater than 5%, 10%, 20%, 25%, 50%, 70%, 90%, or at least 95% of the cell lysate.

Lipids can also be extracted from a lysate via a solventless extraction procedure without substantial or any use of organic solvents or oils by cooling the lysate. Sonication can also be used, particularly if the temperature is between room temperature and 65° C. Such a lysate on centrifugation or settling can be separated into layers, one of which is an aqueous:lipid layer. Other layers can include a solid pellet, an aqueous layer, and a lipid layer. Lipid can be extracted from the emulsion layer by freeze thawing or otherwise cooling the emulsion. In such methods, it is not necessary to add any organic solvent or oil. If any solvent or oil is added, it can be below 5% v/v or w/w of the lysate.

IV. Combining Microalgal Biomass or Materials Derived Therefrom with other Cosmetic Ingredients In one aspect, the present invention is directed to methods of combining microalgal biomass and/or microalgal oil, as described above, with at least one other cosmetic ingredient, as described below, to form a cosmetic composition.

In some cases, the cosmetic composition formed by the combination of microalgal biomass and/or microalgal oil comprises at least 1%, at least 5%, at least 10%, at least 25%, or at least 50% w/w microalgal biomass or microalgal oil, respectively. In some embodiments, cosmetic compositions formed as described herein comprise at least 2%, at least 3%, at least 4%, at least 15%, at least 20%, at least 30%, at least 35%, at least 40%, at least 45%, at least 55%, at least 60%, at least 65%, at least 70%, at least 75%, at least 80%, at least 85%, at least 90%, or at least 95% w/w microalgal biomass or microalgal oil.

In some cases, the cosmetic composition comprises predominantly intact microalgal cells. In some cases, the cosmetic composition comprises at least 50% intact cells, or at least 60%, at least 70%, or at least 80% intact cells. In other embodiments, the cosmetic composition comprises microalgal biomass that has been homogenized to form a whole cell dispersion.

A. Substitution of Algal Biomass and Algal Oil in Cosmetic Products

In some cases, microalgal biomass can be substituted for other components that would otherwise be conventionally included in a cosmetic product. In at least one embodiment, the cosmetic composition formed by the methods of the invention is free of oil other than microalgal oil contributed by the microalgal biomass and entrapped therein.

In various embodiments, microalgal biomass can be substituted for all or a portion of conventional cosmetic ingredients such as exfoliants, antioxidants, colorants, and the like, to the extent that the components of the microalgal biomass replace the corresponding conventional components in like kind, or adequately substitute for the conventional components to impart the desired characteristics to the cosmetic composition.

In some cases, microalgal oil can be substituted for oils conventionally used in cosmetic compositions. As described herein, oils produced by microalgae can be tailored by culture conditions or lipid pathway engineering to comprise particular fatty acid components. Thus, the oils generated by the microalgae of the present invention can be used to replace conventional cosmetic ingredients such as essential oils, fragrance oils, and the like. In at least one embodiment, the cosmetic composition formed by the methods of the present invention is free of oil other than microalgal oil.

B. Other Cosmetic Ingredients

Microalgal biomass and microalgal oil are combined with at least one other cosmetic ingredients in methods of the present invention to form cosmetic compositions. The at least one other cosmetic ingredient can be selected from conventional cosmetic ingredients suitable for use with the microalgal biomass or microalgal oil with regard to the intended use of the composition. Such other cosmetic ingredients include, without limitation, absorbents, abrasives, anticaking agents, antifoaming agents, antibacterial agents, binders, biological additives, buffering agents, bulking agents, chemical additives, cosmetic biocides, denaturants, cosmetic astringents, drug astringents, external analgesics, film formers, humectants, opacifying agents, fragrances and flavor oils, pigments, colorings, essential oils, skin sensates, emollients, skin soothing agents, skin healing agents, pH adjusters, plasticizers, preservatives, preservative enhancers, propellants, reducing agents, skin-conditioning agents, skin penetration enhancing agents, skin protectants, solvents, suspending agents, emulsifiers, thickening agents, solubilizing agents, soaps, sunscreens, sunblocks, ultraviolet light absorbers or scattering agents, sunless tanning agents, antioxidants and/or radical scavengers, chelating agents, sequestrants, anti-acne agents, anti-inflammatory agents, anti-androgens, depilation agents, desquamation agents/exfoliants, organic hydroxy acids, vitamins, vitamin derivatives, and natural extracts.

Microalgal biomass and microalgal oil can also be combined with polysaccharides, including polysaccharides from microalgae. Examples of such polysaccharides can be found, for example, in PCT/US2007/001653 "Microalgae-derived Compositions for Improving the Health and Appearance of Skin", including beads of partially soluble polysaccharides.

Essential oils include allspice, amyris, angelica root, anise seed, basil, bay, bergamot, black pepper, cajeput, camphor, cananga, cardamom, carrot seed, cassia, catnip, cedarwood, chamomile, cinnamon bark, cinnamon leaf, citronella java, clary sage, clovebud, coriander, cornmint, cypress, davana, dill seed, elemi, eucalyptus, fennel, fir, frankincense, geranium bourbon, geranium roast, geranium, ginger, grapefruit pink, grapefruit, gurjum balsam, hyssop, juniper berry, lavandin, lavandula, lavender, lemon myrtle, lemon tea tree, lemon, lemongrass, lime, litsea cubeba, mandarin, marjoram, mullein, myrrh, neroli, nerolina, niaouli, nutmeg, orange, palmarosa, patchouli, peppermint, petitgrain, pine needle, ravensara, ravintsara, rosalina, rose, rosemary, rosewood, sage, sandalwood, spearmint, spikenard, star anise, tangerine, tea tree, thyme, tulsi, verbena, vetiver, ylang ylang, and zdravetz, or combinations thereof.

Fragrances and flavor oils include absolute tulip, almond, amaretto, amber, anais, apple, apple cinnamon, apple spice, apricot, apricot crème, arabian musk, asian pear, asian plum blossom, autumn woods, banana, basil, basil nectarine, bay rum, bayberry, bergamot, berries and cream, birthday cake, black cherry, black tea, blackberry tea, blackcurrent, blue nile, blueberry delight, brambleberry preserves, brown sugar, bubble gum, buttercream, butterscotch, calla lily, cantaloupe, caramel apple, carnation, carrot cake, chai tea, chamomile, china musk, china rain, chinese peony, chrysanthemum, cinnamon, coconut, coconut cream, cotton candy, cranberry, cucumber, cucumber melon, daffodil, dandelion, delphinium, dewberry, dulce de leche, earl grey tea, easter cookie, egg nog, eqyptian musk, enchanted forest, english lavender, english pear, evergreen, fig, frangipani, frankincense, french vanilla, fresh apple, fresh brewed coffee, fruit punch, gardenia, geranium, ginger lily, gingerbread, grape, grapefruit, green apple, green grass, green tea, guava, guava flower, hawaiian white ginger, heliotrope, hemp, herbaceous, holiday fruitcake, hollyberry, honey ginger, honey, honeysuckle, jasmine, jasmine tea, juniper berries, kiwi, lavender, leather, lemon, lemon parsley, lilac, lime, loganberry, lotus blossom, magnolia, mandarin, mango, mango and kiwi, maple, milk chocolate, mimosa, minty lime, mulberry, myrrh, neroli, oakmoss, oatmeal, ocean rain, orange blossom, orange sherbet, orange vanilla, papaya, passion fruit, patchouli, peach, peaches and cream, pearberry, peppermint, pikaki, pina colada, pineapple, pomegranate, pumpkin pie, raisins and almonds, raspberry, roasted nuts, rosewood, sage, sandalwood, sassafras, sea moss, sesame, siberian pine, snowberry, spanish moss, spice, strawberry, sugar plum, suntan lotion, sweet clove, sweet grass, sweet pea, tangerine, thai coconut, timber, tomato leaf, vanilla, watermelon, white chocolate, wild cherry, wisteria, witches brew, and ylang ylang, or combinations thereof.

Exfoliants include particles that can be used to dislodge dead skin cells, dirt, or other materials from the surface of the skin, and include without limitation, fruit seeds and fibers, grain powders, nut and seed meals, and oil or wax beads. Fruit fibers include blueberry, cranberry, grape, kiwi, raspberry, blackberry, strawberry, and the like. Grain powders include oat powder, and almond powder, or the like, milled to varying degrees of coarseness. Polymer beads, such as those made from polyethylene, or the like, can also be used. The removal of dead skin cells and/or the outer most layer of skin can provide an opportunity for bioactive agents, such as carotenoids, which can also be present in the compositions of the invention, to have greater access to deeper layers of the skin.

Extracts, including $CO_2$ extracts, include herbal extracts derived from conventional extraction procedure, or via the use of liquefied carbon dioxide. Herbs include aloe vera leaf, alfalfa leaf, alkanet root, annatto seed, arrowroot, burdock root, calendula petals, carrot root, chamomile flower, comfrey leaf, cornsilk, dutch blue poppies, fennel seed, ginger root, ginseng, green tea leaf, jasmine flower, juniper berries, lavender buds, lemon peel, lemongrass, marshmallow root, nettles, oat straw, orange peel, paprika, parsley, peppermint leaf, rose buds, rose petals, rosehip, rosemary leaf, shavegrass, spearmint leaf, and st. john's wort, or combinations thereof.

Colorings, including glitters, include green #5, green #8, orange #4, red #22, red #33, violet #2, blue #1, green #3, red #40, yellow #5, yellow #6, green #6, red #17, as well as pearlescent micas and tinting herbs such as henna leaf, sandalwood, turmeric, cranberry, kiwi, raspberry, alkanet, annatto, carrot root, nettles, paprika, and parsley.

Specific examples of other cosmetic ingredients are described below. Any one or more of these can be optionally combined with microalgal biomass or microalgal oil in accordance with the present invention to form a cosmetic composition. The active ingredients described below are categorized by their cosmetic and/or therapeutic benefit or their postulated mode of action. However, it is to be understood that these ingredients can in some instances provide more than one cosmetic and/or therapeutic benefit or operate via more than one mode of action. Therefore, classifications herein are made for the sake of convenience and are not intended to limit the ingredient to that particular application or applications listed.

A safe and effective amount of an anti-inflammatory agent can optionally be added to the compositions of the present invention, preferably from about 0.1% to about 10%, more preferably from about 0.5% to about 5%, of the composition.

The anti-inflammatory agent enhances the skin appearance benefits of the present invention, e.g., such agents contribute to a more uniform and acceptable skin tone or color. The exact amount of anti-inflammatory agent to be used in the compositions will depend on the particular anti-inflammatory agent utilized since such agents vary widely in potency.

Steroidal anti-inflammatory agents, including but not limited to, corticosteroids such as hydrocortisone, hydroxyltriamcinolone, alpha-methyl dexamethasone, dexamethasone-phosphate, beclomethasone dipropionates, clobetasol valerate, desonide, desoxymethasone, desoxycorticosterone acetate, dexamethasone, dichlorisone, diflorasone diacetate, diflucortolone valerate, fluadrenolone, fluclorolone acetonide, fludrocortisone, flumethasone pivalate, fluosinolone acetonide, fluocinonide, flucortine butylesters, fluocortolone, fluprednidene (fluprednylidene) acetate, flurandrenolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenolone, fludrocortisone, diflurosone diacetate, fluradrenolone acetonide, medrysone, amcinafel, amcinafide, betamethasone and the balance of its esters, chloroprednisone, chlorprednisone acetate, clocortelone, clescinolone, dichlorisone, diflurprednate, flucloronide, flunisolide, fluoromethalone, fluperolone, fluprednisolone, hydrocortisone valerate, hydrocortisone cyclopentylpropionate, hydrocortamate, meprednisone, paramethasone, prednisolone, prednisone, beclomethasone dipropionate, triamcinolone, and mixtures thereof may be used. The preferred steroidal anti-inflammatory for use is hydrocortisone.

A second class of anti-inflammatory agents which is useful in the compositions includes the nonsteroidal anti-inflammatory agents. The variety of compounds encompassed by this group are well-known to those skilled in the art. For detailed disclosure of the chemical structure, synthesis, side effects, etc. of nonsteroidal anti-inflammatory agents, reference may be had to standard texts, including Anti-inflammatory and Anti-Rheumatic Drugs, K. D. Rainsford, Vol. I-III, CRC Press, Boca Raton, (1985), and Anti-inflammatory Agents, Chemistry and Pharmacology, 1, R. A. Scherrer, et al., Academic Press, New York (1974), each incorporated herein by reference.

Specific non-steroidal anti-inflammatory agents useful in accordance with the present invention include, but are not limited to: 1) the oxicams, such as piroxicam, isoxicam, tenoxicam, sudoxicam, and CP-14,304; 2) the salicylates, such as aspirin, disalcid, benorylate, trilisate, safapryn, solprin, diflunisal, and fendosal; 3) the acetic acid derivatives, such as diclofenac, fenclofenac, indomethacin, sulindac, tolmetin, isoxepac, furofenac, tiopinac, zidometacin, acematacin, fentiazac, zomepirac, clindanac, oxepinac, felbinac, and ketorolac; 4) the fenamates, such as mefenamic, meclofenamic, flufenamic, niflumic, and tolfenamic acids; 5) the propionic acid derivatives, such as ibuprofen, naproxen, benoxaprofen, flurbiprofen, ketoprofen, fenoprofen, fenbufen, indopropfen, pirprofen, carprofen, oxaprozin, pranoprofen, miroprofen, tioxaprofen, suprofen, alminoprofen, and tiaprofenic; and 6) the pyrazoles, such as phenylbutazone, oxyphenbutazone, feprazone, azapropazone, and trimethazone.

Mixtures of these non-steroidal anti-inflammatory agents may also be employed, as well as the dermatologically acceptable salts and esters of these agents. For example, etofenamate, a flufenamic acid derivative, is particularly useful for topical application. Of the nonsteroidal anti-inflammatory agents, ibuprofen, naproxen, flufenamic acid, etofenamate, aspirin, mefenamic acid, meclofenamic acid, piroxicam and felbinac are preferred; ibuprofen, naproxen, etofenamate, aspirin and flufenamic acid are most preferred.

Finally, so-called "natural" anti-inflammatory agents are useful in methods of the present invention. Such agents may suitably be obtained as an extract by suitable physical and/or chemical isolation from natural sources (e.g., plants, fungi, or by-products of microorganisms). For example, candelilla wax, alpha bisabolol, aloe vera, Manjistha (extracted from plants in the genus *Rubia*, particularly *Rubia Cordifolia*), and Guggal (extracted from plants in the genus *Commiphora*, particularly *Commiphora Mukul*), kola extract, chamomile, and sea whip extract, may be used.

Additional anti-inflammatory agents useful herein include compounds of the Licorice (the plant genus/species *Glycyrrhiza glabra*) family, including glycyrrhetic acid, glycyrrhizic acid, and derivatives thereof (e.g., salts and esters). Suitable salts of the foregoing compounds include metal and ammonium salts. Suitable esters include $C_2$-$C_{24}$ saturated or unsaturated esters of the acids, preferably $C_{10}$-$C_{24}$, more preferably $C_{16}$-$C_{24}$. Specific examples of the foregoing include oil soluble licorice extract, the glycyrrhizic and glycyrrhetic acids themselves, monoammonium glycyrrhizinate, monopotassium glycyrrhizinate, dipotassium glycyrrhizinate, 1-beta-glycyrrhetic acid, stearyl glycyrrhetinate, and 3-stearyloxy-glycyrrhetinic acid, and disodium 3-succinyloxy-beta-glycyrrhetinate. Stearyl glycyrrhetinate is preferred.

In some embodiments, the compositions of the present invention also optionally contain a retinoid. The vitamin $B_3$ compound and retinoid provide unexpected benefits in regulating skin condition, especially in therapeutically regulating signs of skin aging, more especially wrinkles, lines, and pores. Without intending to be bound or otherwise limited by theory, it is believed that the vitamin $B_3$ compound increases the conversion of certain retinoids to trans-retinoic acid, which is believed to be the biologically active form of the retinoid, to provide synergistic regulation of skin condition (namely, increased conversion for retinol, retinol esters, and retinal). In addition, the vitamin $B_3$ compound unexpectedly mitigates redness, inflammation, dermatitis and the like which may otherwise be associated with topical application of retinoid (often referred to, and hereinafter alternatively referred to as "retinoid dermatitis"). Furthermore, the combined vitamin $B_3$ compound and retinoid tend to increase the amount and activity of thioredoxin, which tends to increase collagen expression levels via the protein AP-1. Therefore, compositions of the present invention enable reduced active levels, and therefore reduced potential for retinoid dermatitis, while retaining significant positive skin conditioning benefits. In addition, higher levels of retinoid may still be used to obtain greater skin conditioning efficacy, without undesirable retinoid dermatitis occurring.

As used herein, "retinoid" includes all natural and/or synthetic analogs of Vitamin A or retinol-like compounds which possess the biological activity of Vitamin A in the skin as well as the geometric isomers and stereoisomers of these compounds. The retinoid is preferably retinol, retinol esters (e.g., $C_2$-$C_{22}$ alkyl esters of retinol, including retinyl palmitate, retinyl acetate, retinyl proprionate), retinal, and/or retinoic acid (including all-trans retinoic acid and/or 13-cis-retinoic acid), more preferably retinoids other than retinoic acid. These compounds are well known in the art and are commercially available from a number of sources, e.g., Sigma Chemical Company (St. Louis, Mo.).

The cosmetic compositions of this invention may contain a safe and effective amount of the retinoid, such that the resultant composition is safe and effective for regulating skin condition, preferably for regulating visible and/or tactile discontinuities in skin, more preferably for regulating signs of skin aging, even more preferably for regulating visible and/or tactile discontinuities in skin texture associated with skin aging. The compositions preferably contain from or about 0.005% to or about 2%, more preferably 0.01% to or about 2%, retinoid. Retinol is most preferably used in an amount of from or about 0.01% to or about 0.15%; retinol esters are most preferably used in an amount of from or about 0.01% to or about 2% (e.g., about 1%); retinoic acids are most preferably used in an amount of from or about 0.01% to or about 0.25%. The retinoid may be included as the substantially pure material, or as an extract obtained by suitable physical and/or chemical isolation from natural (e.g., plant) sources. The retinoid is preferably substantially pure.

In some embodiments, the compositions of the present invention also optionally contain an antibacterial agent. As used herein, "antibacterial agent" means a compound capable of destroying bacteria cells, preventing the development of bacteria or preventing the pathogenic action of bacteria. Antibacterial agents are useful, for example, in controlling acne. A safe and effective amount of an antibacterial agent can optionally be added to cosmetic compositions of the subject invention, preferably from about 0.001% to about 10%, more preferably from about 0.01% to about 5%, also from about 0.05% to about 2% or from about 0.05% to about 1% of the compositions. Preferred antibacterial agents useful in the cosmetic compositions of the invention are benzoyl peroxide, erythromycin, tetracycline, clindamycin, azelaic acid, and sulfur resorcinol.

In some embodiments, the compositions of the present invention also optionally contain an antiandrogen. As used herein, "anti-androgen" means a compound capable of correcting androgen-related disorders by interfering with the action of androgens at their target organs. The target organ for the cosmetic compositions of the present invention is mammalian skin. Exemplary antiandrogens include pregnenalone (and its derivatives), hops extract, oxygenated alkyl substituted bicyclo alkanes (e.g., ethoxyhexyl-bicyclo octanones such as marketed by Chantal Pharmaceutical of Los Angeles, Calif. under the trade names ETHOCYN and CYOCTOL, and 2-(5-ethoxy hept-1-yl)bicylo[3.3.0]octanone), and oleanolic acid. Suitable antiandrogens are disclosed in U.S. Pat. Nos. 4,689,345 and 4,855,322, both issued to Kasha et al. on Aug. 25, 1987 and Aug. 8, 1989, respectively, each incorporated herein by reference. Antiandrogens can optionally be added to cosmetic compositions of the invention.

Exposure to ultraviolet light can result in excessive scaling and texture changes of the stratum corneum. Therefore, the cosmetic compositions of the subject invention optionally contain a sunscreen or sunblock. Suitable sunscreens or sunblocks may be organic or inorganic.

A wide variety of conventional sunscreening agents are suitable for use in the cosmetic compositions described herein. Sagarin, et al., at Chapter VIII, pages 189 et seq., of Cosmetics Science and Technology (1972), discloses numerous suitable agents, and is incorporated herein by reference. Specific suitable sunscreening agents include, for example: p-aminobenzoic acid, its salts and its derivatives (ethyl, isobutyl, glyceryl esters; p-dimethylaminobenzoic acid); anthranilates (i.e., o-amino-benzoates; methyl, menthyl, phenyl, benzyl, phenylethyl, linalyl, terpinyl, and cyclohexenyl esters); salicylates (amyl, phenyl, octyl, benzyl, menthyl, glyceryl, and di-pro-pyleneglycol esters); cinnamic acid derivatives (menthyl and benzyl esters, a-phenyl cinnamonitrile; butyl cinnamoyl pyruvate); dihydroxycinnamic acid derivatives (umbelliferone, methylumbelliferone, methylaceto-umbelliferone); trihydroxy-cinnamic acid derivatives (esculetin, methylesculetin, daphnetin, and the glucosides, esculin and daphnin); hydrocarbons (diphenylbutadiene, stilbene); dibenzalacetone and benzalacetophenone; naphtholsulfonates (sodium salts of 2-naphthol-3,6-disulfonic and of 2-naphthol-6,8-disulfonic acids); di-hydroxynaphthoic acid and its salts; o- and p-hydroxybiphenyldisulfonates; coumarin derivatives (7-hydroxy, 7-methyl, 3-phenyl); diazoles (2-acetyl-3-bromoindazole, phenyl benzoxazole, methyl naphthoxazole, various aryl benzothiazoles); quinine salts (bisulfate, sulfate, chloride, oleate, and tannate); quinoline derivatives (8-hydroxyquinoline salts, 2-phenylquinoline); hydroxy- or methoxy-substituted benzophenones; uric and violuric acids; tannic acid and its derivatives (e.g., hexaethylether); (butyl carbotol) (6-propyl piperonyl) ether; hydroquinone; benzophenones (oxybenzone, sulisobenzone, dioxybenzone, benzoresorcinol, 2,2',4,4'-tetrahydroxybenzophenone, 2,2'-dihydroxy-4, 4'-dimethoxybenzophenone, octabenzone; 4-isopropyldibenzoylmethane; butylmethoxydibenzoylmethane; etocrylene; octocrylene; [3-(4'-methylbenzylidene bornan-2-one) and 4-isopropyl-di-benzoylmethane.

Also optionally useful in the cosmetic compositions are sunscreens such as those disclosed in U.S. Pat. No. 4,937,370 issued to Sabatelli on Jun. 26, 1990, and U.S. Pat. No. 4,999,186 issued to Sabatelli & Spirnak on Mar. 12, 1991, both of which are incorporated herein by reference. The sunscreening agents disclosed therein have, in a single molecule, two distinct chromophore moieties which exhibit different ultra-violet radiation absorption spectra. One of the chromophore moieties absorbs predominantly in the UVB radiation range and the other absorbs strongly in the UVA radiation range. Members of this class of sunscreening agents include 4-N,N-(2-ethylhexyl)methyl-aminobenzoic acid ester of 2,4-dihydroxybenzophenone; N,N-di-(2-ethylhexyl)-4-aminobenzoic acid ester with 4-hydroxydibenzoylmethane; 4-N,N-(2-ethylhexyl)methyl-aminobenzoic acid ester with 4-hydroxydibenzoylmethane; 4-N,N-(2-ethylhexyl)methyl-aminobenzoic acid ester of 2-hydroxy-4-(2-hydroxyethoxy)benzophenone; 4-N,N-(2-ethylhexyl)-methylaminobenzoic acid ester of 4-(2-hydroxyethoxy) dibenzoylmethane; N,N-di-(2-ethylhexyl)-4-aminobenzoic acid ester of 2-hydroxy-4-(2-hydroxyethoxy)benzophenone; and N,N-di-(2-ethylhexyl)-4-aminobenzoic acid ester of 4-(2-hydroxyethoxy)dibenzoylmethane and mixtures thereof.

Suitable inorganic sunscreens or sunblocks include metal oxides, e.g., zinc oxide and titanium dioxide.

A safe and effective amount of the sunscreen or sunblock is used, typically from about 1% to about 20%, more typically from about 2% to about 10%. Exact amounts will vary depending upon the sunscreen chosen and the desired Sun Protection Factor (SPF).

An agent may also be added to any of the compositions useful in the subject invention to improve the skin substantivity of those compositions, particularly to enhance their resistance to being washed off by water, or rubbed off. A preferred agent which will provide this benefit is a copolymer of ethylene and acrylic acid. Compositions comprising this copolymer are disclosed in U.S. Pat. No. 4,663,157, Brock, issued May 5, 1987, which is incorporated herein by reference.

Cosmetic compositions of the present invention can optionally include an anti-oxidant/radical scavenger as an active ingredient. The anti-oxidant/radical scavenger is especially useful for providing protection against UV radiation which can cause increased scaling or texture changes in the stratum corneum and against other environmental agents which can cause skin damage.

A safe and effective amount of an anti-oxidant/radical scavenger may be added to the compositions of the subject invention, preferably from about 0.1% to about 10%, more preferably from about 1% to about 5%, of the composition.

Anti-oxidants/radical scavengers such as ascorbic acid (vitamin C) and its salts, ascorbyl esters of fatty acids, ascorbic acid derivatives (e.g., magnesium ascorbyl phosphate), tocopherol (vitamin E), tocopherol sorbate, other esters of tocopherol, butylated hydroxy benzoic acids and their salts, 6-hydroxy-2,5,7,8-tetramethylchroman-2-carboxylic acid (commercially available under the tradename Trolox.sup.R), gallic acid and its alkyl esters, especially propyl gallate, uric acid and its salts and alkyl esters, sorbic acid and its salts, amines (e.g., N,N-diethylhydroxylamine, amino-guanidine), sulfhydryl compounds (e.g., glutathione), dihydroxy fumaric acid and its salts, lycine pidolate, arginine pilolate, nordihydroguaiaretic acid, bioflavonoids, lysine, methionine, proline, catalase, superoxide dismutase, lactoferrin, silymarin, tea extracts, grape skin/seed extracts, melanin, and rosemary extracts may be used.

As used herein, "chelating agent" refers to an active agent capable of removing a metal ion from a system by forming a complex so that the metal ion cannot readily participate in or catalyze chemical reactions. The inclusion of a chelating agent is especially useful for providing protection against UV radiation which can contribute to excessive scaling or skin texture changes and against other environmental agents which can cause skin damage.

A safe and effective amount of a chelating agent can optionally be added to the cosmetic compositions of the subject invention, preferably from about 0.1% to about 10%, more preferably from about 1% to about 5%, of the composition. Exemplary chelators that are useful herein are disclosed in U.S. Pat. No. 5,487,884, issued Jan. 30, 1996 to Bissett et al.; International Publication No. 91/16035, Bush et al., published Oct. 31, 1995; and International Publication No. 91/16034, Bush et al., published Oct. 31, 1995; all incorporated herein by reference. Preferred chelators useful in compositions of the subject invention are furildioxime and derivatives thereof.

Compositions of the present invention optionally comprise an organic hydroxy acid. Suitable hydroxy acids include $C_1$-$C_{18}$ hydroxy acids, preferably $C_8$ or below. The hydroxy acids can be substituted or unsubstituted, straight chain, branched chain or cyclic (preferably straight chain), and saturated or unsaturated (mono- or poly-unsaturated) (preferably saturated). Non-limiting examples of suitable hydroxy acids include salicylic acid, glycolic acid, lactic acid, 5 octanoyl salicylic acid, hydroxyoctanoic acid, hydroxycaprylic acid, and lanolin fatty acids. Preferred concentrations of the organic hydroxy acid range from about 0.1% to about 10%, more preferably from about 0.2% to about 5%, also preferably from about 0.5% to about 2%. Salicylic acid is preferred. The organic hydroxy acids enhance the skin appearance benefits of the present invention. For example, the organic hydroxy acids tend to improve the texture of the skin.

A safe and effective amount of a desquamation agent can optionally be added to the cosmetic compositions of the subject invention. In some embodiments, desquamation agents/exfoliants can comprise from about 0.1% to about 10%, from about 0.2% to about 5%, or from about 0.5% to about 4% of the composition. Desquamation agents tend to improve the texture of the skin (e.g., smoothness). A variety of desquamation agents are known in the art and are suitable for use herein, including but not limited to the organic hydroxy agents described above.

The compositions of the present invention can also optionally include a safe and effective amount of a depilation agent. When used, the composition preferably contains from about 0.1% to about 10%, more preferably from about 0.2% to about 5%, also preferably from about 0.5% to about 2% of depilation agent. A depilation agent preferred for use herein comprises a sulfhydryl compound, e.g., N-acetyl-L-cysteine.

The compositions of the present invention can also optionally comprise a skin lightening agent. When used, the compositions preferably comprise from about 0.1% to about 10%, more preferably from about 0.2% to about 5%, also preferably from about 0.5% to about 2%, of a skin lightening agent. Suitable skin lightening agents include those known in the art, including kojic acid, arbutin, ascorbic acid and derivatives thereof, e.g., magnesium ascorbyl phosphate.

The cosmetic compositions of the present invention can also optionally comprise a zinc salt. Zinc salts are especially preferred where the composition contains a sulfhydryl compound, e.g., N-acetyl-L-cysteine. Without intending to be limited or bound by theory, it is believed that the zinc salt acts as a chelating agent capable of complexing with the sulfhydryl compound prior to topical application, stabilizes the sulfhydryl compound and/or controls odor associated with the sulfhydryl compound. Concentrations of the zinc salt can range from about 0.001% to about 10%, more preferably from about 0.01% to about 5%, most preferably from about 0.1% to about 0.5% by weight of the composition.

Preferred zinc salts include zinc acetate, zinc acetate hydrates such as zinc acetate-2-water, zinc aluminum oxide complexes such as gahnite, zinc diamine, zinc antimonide, zinc bromate hydrates such as zinc bromate-6water, zinc bromide, zinc carbonates such as zincspar and smithsonite, zinc chlorate hydrates such as zinc chlorate-4-water, zinc chloride, zinc diamine dichloride, zinc citrate, zinc chromate, zinc dichromate, zinc diphosphate, zinc hexacyanofluoride ferrate (II), zinc fluoride, zinc fluoride hydrates such as zinc fluoride-4-water, zinc formate, zinc formate hydrates such as zinc formate-2-water, zinc hydroxide, zinc iodate, zinc iodate hydrates such as zinc iodate-2-water, zinc iodide, zinc iron oxide complexes, zinc nitrate hydrates such as zinc nitrate-6-water, zinc nitride, zinc oxalate hydrates such as zinc oxalate-2-water, zinc oxides such as zincite, zinc perchlorate hydrates such as zinc perchlorate-6-water, zinc permanganate hydrates such as zinc permanganate-6-water, zinc peroxide, zinc p-phenolsulfonate hydrates such as zinc p-phenolsulfonate-8-water, zinc phosphate, zinc phosphate hydrates such as zinc phosphate-4-water, zinc phosphide, zinc-propionate, zinc selenate hydrates such as zinc selenate-5-water, zinc selenide, zinc silicates such as zinc silicate (2) and zinc silicate (4), zinc silicon oxide water complexes such as hemimorphite, zinc hexafluorosilicate hydrates such as zinc hexafluorosilicate-6-water, zinc stearate, zinc sulfate, zinc sulfate hydrates such as zinc sulfate-7-water, zinc sulfide, zinc sulfite hydrates such as zinc sulfite-2-water, zinc telluride, zinc thiocyanate, zinc (II) salts of N-acetyl L-cysteine, and mixtures thereof.

The cosmetic compositions of the present invention can optionally further comprise a humectant, moisturizing agent or other skin conditioning agent. A variety of these materials can be employed and each can be present at a level of from or about 0.1% to or about 20%, more preferably from or about 1% to or about 10%, and most preferably from or about 2% to or about 5%. These materials include guanidine; glycolic acid and glycolate salts (e.g. ammonium and quaternary alkyl ammonium); lactic acid and lactate salts (e.g. ammonium and quaternary alkyl ammonium); aloe vera in any of its variety of forms (e.g., aloe vera gel); polyhydroxy alcohols such as sorbitol, glycerol, hexanetriol, propylene glycol, butylene glycol, hexylene glycol and the like; polyethylene glycols; sugars and starches; sugar and starch derivatives (e.g., alkoxylated glucose); hyaluronic acid; lactamide monoethanolamine; acetamide monoethanolamine; and mixtures thereof. Also useful herein are the propoxylated glycerols described in U.S. Pat. No. 4,976,953, which is description is incorporated herein by reference.

Also optionally useful are various $C_1$-$C_{30}$ monoesters and polyesters of sugars and related materials. These esters are derived from a sugar or polyol moiety and one or more carboxylic acid moieties. Depending on the constituent acid and sugar, these esters can be in either liquid or solid form at room temperature. Examples of liquid esters include: glucose tetraoleate, the glucose tetraesters of soybean oil fatty acids (unsaturated), the mannose tetraesters of mixed soybean oil fatty acids, the galactose tetraesters of oleic acid, the arabinose tetraesters of linoleic acid, xylose tetralinoleate, galactose pentaoleate, sorbitol tetraoleate, the sorbitol hexaesters of unsaturated soybean oil fatty acids, xylitol pentaoleate, sucrose tetraoleate, sucrose pentaoletate, sucrose hexaoleate, sucrose hepatoleate, sucrose octaoleate, and mixtures thereof. Examples of solid esters include: sorbitol hexaester in which the carboxylic acid ester moieties are palmitoleate and arachidate in a 1:2 molar ratio; the octaester of raffinose in which the carboxylic acid ester moieties are linoleate and behenate in a 1:3 molar ratio; the heptaester of maltose wherein the esterifying carboxylic acid moieties are sunflower seed oil fatty acids and lignocerate in a 3:4 molar ratio; the octaester of sucrose wherein the esterifying carboxylic acid moieties are oleate and behenate in a 2:6 molar ratio; and the octaester of sucrose wherein the esterifying carboxylic acid moieties are laurate, linoleate and behenate in a 1:3:4 molar ratio. A preferred solid material is sucrose polyester in which the degree of esterification is 7-8, and in which the fatty acid moieties are C:18 mono- and/or di-unsaturated and behenic, in a molar ratio of unsaturates:behenic of 1:7 to 3:5. A particularly preferred solid sugar polyester is the octaester of sucrose in which there are about 7 behenic fatty acid moieties and about 1 oleic acid moiety in the molecule. The ester materials are further described in, U.S. Pat. Nos. 2,831,854, 4,005,196, to Jandacek, issued Jan. 25, 1977; U.S. Pat. No. 4,005,195, to Jandacek, issued Jan. 25, 1977, U.S. Pat. No. 5,306,516, to Letton et al., issued Apr. 26, 1994; U.S. Pat. No. 5,306,515, to Letton et al., issued Apr. 26, 1994; U.S. Pat. No. 5,305,514, to Letton et al., issued Apr. 26, 1994; U.S. Pat. No. 4,797,300, to Jandacek et al., issued Jan. 10, 1989; U.S. Pat. No. 3,963,699, to Rizzi et al, issued Jun. 15, 1976; U.S. Pat. No. 4,518,772, to Volpenhein, issued May 21, 1985; and U.S. Pat. No. 4,517,360, to Volpenhein, issued May 21, 1985; all of which are incorporated by reference herein in their entirety.

The cosmetic compositions of the present invention can also optionally include an extract obtained by suitable physical and/or chemical isolation from natural sources (e.g., plants), including those known in the topical personal care art. Preferred extracts are those which enhance the skin appearance benefits of the present invention, and which are preferably used in a safe and effective amount, more preferably an amount of from 0.1% to about 20%, even more preferably 0.5% to about 10%, also from 1% to about 5%. Such extracts include plant and fungal extracts such as extracts of yeast, rice bran, and of the plant Centella Asiatica. Natural extracts of Centella Asiatica are preferred and are commercially available from MMP, Inc. of Plainfield, N.J. under the trade name(s) Centella Asiatica E.P.C.A. ("Extract Purified of Centella asiatica") and Genines amel. Genines amel is the purer form of the extract.

Compounds which are known to stimulate the production of collagen can also optionally be used in cosmetic composition of the present invention. Such compounds include Factor X (kinetin), Factor Z (zeatin), n-methyl taurine, dipalmitoyl hydroxyproline, palmitoyl hydroxy wheat protein, biopeptide CL (palmitoyl glycyl-histidyl-lysine), ASC III (Amplifier of Synthesis of Collagen III, E. Merck, Germany), and beta glucan.

The cosmetic compositions hereof can also optionally include natural ceramides or the like, for example, ceramide 1-6.

The cosmetic compositions can also optionally contain an oil absorbent such as are known in the art, e.g. clays (e.g. bentonite) and polymeric absorbents (e.g., Polymeric derivatised starches, (e.g., from National Starch), Derivatised globulin proteins, such as BioPol OE (Arch PC), MICROSPONGES 5647 and POLYTRAP, both commercially available from Advanced Polymer Systems, Inc. of Redwood City, Calif., USA., MICROSPONGES 5647 is a polymer mixture derived from styrene, methyl methacrylate, and hydrogel acrylate/methacrylate.

Other examples of additional components optionally useful herein include the following: water-soluble vitamins and derivatives thereof (e.g., vitamin C); polyethyleneglycols and polypropyleneglycols; polymers for aiding the film-forming properties and substantivity of the composition (such as a copolymer of eicosene and vinyl pyrrolidone, an example of which is available from GAF Chemical Corporation as Ganex® V-220). Also useful are crosslinked and noncrosslinked nonionic and cationic polyacrylamides (e.g., Salcare SC92 which has the CTFA designation polyquaternium 32 (and) mineral oil, and Salcare SC 95 which has the CTFA designation polyquaternium 37 (and) mineral oil (and) PPG-1 trideceth-6, and the nonionic Seppi-Gel polyacrylamides available from Seppic Corp.). Also useful are crosslinked and uncrosslinked carboxylic acid polymers and copolymers such as those containing one or more monomers derived from acrylic acid, substituted acrylic acids, and salts and esters of these acrylic acids and the substituted acrylic acids, wherein the crosslinking agent contains two or more carbon-carbon double bonds and is derived from a polyhydric alcohol (examples useful herein include the carbomers, which are homopolymers of acrylic acid crosslinked with allyl ethers of sucrose or pentaerytritol and which are available as the Carbopol® 900 series from B. F. Goodrich, and copolymers of C.sub.10-30 alkyl acrylates with one or more monomers of acrylic acid, methacrylic acid, or one of their short chain (i.e., $C_{1-4}$ alcohol) esters, wherein the crosslinking agent is an allyl ether of sucrose or pentaerytritol, these copolymers being known as acrylates/C10-30 alkyl acrylate crosspolymers and are commercially available as Carbopol® 1342, Pemulen TR-1, and Pemulen TR-2, from B. F. Goodrich). These carboxylic acid polymers and copolymers are more fully described in U.S. Pat. No. 5,087,445, to Haffey et al., issued Feb. 11, 1992; U.S. Pat. No. 4,509,949, to Huang et al., issued Apr. 5, 1985; U.S. Pat. No. 2,798,053, to Brown, issued Jul. 2, 1957; which are incorporated by reference herein. See also, CTFA Interna- C. Saponification of Oil-Bearing Microbial Biomass and Extracted Oil In some embodiments, microalgal biomass and/or microalgal oil can be combined with saponified oils derived from microalgae or other microorganisms. These saponified oils can optionally be used in place of soap components that may otherwise be combined with the microalgal biomass or microalgal oil to form cosmetic compositions in accordance with the present invention. In some cases, a portion of a the microalgal oil (triacylglycerides) is saponified, and the partially saponified oil is combined with one or more other cosmetic ingredients to form a cosmetic compositions including both saponified microalgal oil and non-saponified microalgal oil. As described below, the ratio of saponified oil to non-saponified oil can be modified by controlling the quantity of base used in the reaction.

Animal and plant oils are typically made of triacylglycerols (TAGs), which are esters of fatty acids with the trihydric alcohol, glycerol. In an alkaline hydrolysis reaction, the glycerol in a TAG is removed, leaving three carboxylic acid anions that can associate with alkali metal cations such as sodium or potassium to produce fatty acid salts. A typical reaction scheme is as follows:

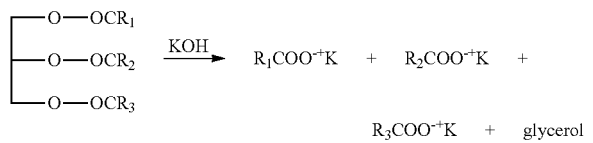

In this scheme, the carboxylic acid constituents are cleaved from the glycerol moiety and replaced with hydroxyl groups. The quantity of base (e.g., KOH) that is used in the reaction is determined by the desired degree of saponification. If the objective is, for example, to produce a soap product that comprises some of the oils originally present in the TAG composition, an amount of base insufficient to convert all of the TAGs to fatty acid salts is introduced into the reaction mixture. Normally, this reaction is performed in an aqueous solution and proceeds slowly, but may be expedited by the addition of heat. Precipitation of the fatty acid salts can be facilitated by addition of salts, such as water-soluble alkali metal halides (e.g., NaCl or KCl), to the reaction mixture. Preferably, the base is an alkali metal hydroxide, such as NaOH or KOH. Alternatively, other bases, such as alkanolamines, including for example triethanolamine and aminomethylpropanol, can be used in the reaction scheme. In some cases, these alternatives may be preferred to produce a clear soap product.

Saponification of oil bearing microbial biomass can be performed on intact biomass or biomass that has been disrupted prior to being subjected to the alkaline hydrolysis reaction. In the former case, intact microbial biomass generated via the culturing of microorganisms as described herein can be directly contacted with a base to convert ester-containing lipid components of the biomass to fatty acid salts. In some cases, all or a portion of the water in which the microbes have been cultured is removed and the biomass is resuspended in an aqueous solution containing an amount of base sufficient to saponify the desired portion of the glycerolipid and fatty acid ester components of the biomass. In some cases, less than 100% of the glycerolipids and fatty acid esters in the biomass are converted to fatty acid salts.

In some methods of the invention, the biomass is disrupted prior to being subjected to the alkaline hydrolysis reaction. Disruption of the biomass can be accomplished via any one or more of the methods described above for lysing cells, including heat-induced lysis, mechanical lysis, or the like, in order to make the intracellular contents of the microorganisms more readily accessible to the base. This can help to facilitate the conversion of TAGs or fatty acid esters to fatty acid salts. Although acid-induced lysis can be used to disrupt the biomass prior to saponification, other methods may be more desirable to reduce the possibility that additional base will be consumed to neutralize any remaining acid during the alkaline hydrolysis reaction, which may impact the conversion efficiency to fatty acid salts. Because the application of heat can expedite the alkaline hydrolysis reaction, heat-induced lysis can be used prior to or during the saponification reaction to produce the fatty acid salts.

In some embodiments, the biomass is not subjected to any treatment, or any treatment other than disruption, prior to being subjected to the alkaline hydrolysis reaction. In some embodiments, prior enrichment of the biomass to increase the ratio of lipid to non-lipid material in the biomass to more than 50% (or by more than 50%) by weight, is performed. In other embodiments, the biomass is subjected to the alkaline hydrolysis reaction without a step of prior enrichment. In some cases, the biomass subjected to the alkaline hydrolysis reaction contains components other than water in the same relative proportions as the biomass at the point of harvesting. In those cases in which substantially all of the water has been removed, the biomass comprises a cellular emulsion or substantially-dried emulsion concentrate.

Any of the microorganisms described herein can be used to produce lipid-containing biomass for the production of saponified oils. In some cases, the microorganisms can also impart other characteristics to the saponified-oil compositions produced from the methods described herein. For example, microalgae of different species, as well as microalgae grown under different conditions, vary in color, including green, yellow, orange, red, and the like. Small quantities of the compounds that impart these colors to the microalgae can contaminate (e.g., by purposefully retaining some of these materials) the resulting saponified-oil compositions and thereby provide natural colorants. In some cases, other constituents of the biomass, including carotenoids and xanthophylls, can also be retained in small quantities in the saponified-oil compositions.

The extent of saponification of the biomass can vary in the methods of the invention. In some cases it is desirable to produce a saponified-oil composition that also includes glycerolipid constituents of the biomass. The appropriate quantity of base (e.g., NaOH) for use in the alkaline hydrolysis reaction can be determined based on an analysis of the glycerolipid and fatty acid ester content of the biomass. In some cases, it is preferable to use an excess of base to directly saponify lipid-containing biomass because some of the base may be consumed by reaction with other constituents of the biomass. In some cases, the use of excess quantities of base to saponify the ester-containing lipid constituents of the biomass results in a saponified oil composition that is undesirably alkaline. In these instances, the composition can be purified to reduce the alkalinity of the composition by boiling the saponified oil composition in water and re-precipitating the fatty acid salts via addition of salts such as NaCl, KCl, or the like. The purified soap composition can then be subjected to further processing, such as removing excess water, introducing various additives into the soap composition, moulding the soap in bars or other shapes, or the like.

In some cases, the fatty acid salts (also referred to as saponified oils) generated from the methods described herein can be combined with microalgal biomass, microalgal oil, and/or other cosmetic ingredients as described herein.

The degree of saponification of extracted lipid constituents of the biomass is more readily controlled because of a reduced probability that the base will be consumed through interaction with components other than glycerolipids or fatty acid esters present in the extracted oil. Extraction of the lipid constituents can be performed via conventional hexane-extraction procedures, or via an oil-extraction or solventless-extraction procedure.

Conventional hexane-extraction (other suitable organic solvents can also be used) generally comprises contacting the biomass or lysate with hexane in an amount and for a period of time sufficient to allow the lipid to form a solution with the hexane. The mixture can then be filtered and the hexane removed by, for example, rotoevaporation. Hexane extraction methods are well known in the art.

Oil extraction includes the addition of an oil directly to a lysate without prior separation of the lysate components. After addition of the oil, the lysate separates either of its own accord or as a result of centrifugation or the like into different layers. The layers can include in order of decreasing density: a pellet of heavy solids, an aqueous phase, an emulsion phase, and an oil phase. The emulsion phase is an emulsion of lipids and aqueous phase. Depending on the percentage of oil added with respect to the lysate (w/w or v/v), the force of centrifugation if any, volume of aqueous media and other factors, either or both of the emulsion and oil phases can be present. Incubation or treatment of the cell lysate or the emulsion phase with the oil is performed for a time sufficient to allow the lipid produced by the microorganism to become solubilized in the oil to form a heterogeneous mixture.

In various embodiments, the oil used in the extraction process is selected from the group consisting of oil from soy, rapeseed, canola, palm, palm kernel, coconut, corn, waste vegetable oil, Chinese tallow, olive, sunflower, cotton seed, chicken fat, beef tallow, porcine tallow, microalgae, macroalgae, *Cuphea*, flax, peanut, choice white grease (lard), *Camelina sativa* mustard seedcashew nut, oats, lupine, kenaf, calendula, hemp, coffee, linseed, hazelnut, euphorbia, pumpkin seed, coriander, camellia, sesame, safflower, rice, tung oil tree, cocoa, copra, pium poppy, castor beans, pecan, jojoba, jatropha, macadamia, Brazil nuts, and avocado. The amount of oil added to the lysate is typically greater than 5% (measured by v/v and/or w/w) of the lysate with which the oil is being combined. Thus, a preferred v/v or w/w of the oil is greater than 5%, or at least 6%, at least 7%, at least 10%, at least 20%, at least 25%, at least 30%, at least 40%, at least 50%, at least 60%, at least 70%, at least 80%, at least 90%, and at least 95% of the cell lysate.

Lipids can also be extracted from a lysate via a solventless extraction procedure without substantial or any use of organic solvents or oils by cooling the lysate. In such methods, the lysate is preferably produced by acid treatment in combination with above room temperature. Sonication can also be used, particularly if the temperature is between room temperature and 65° C. Such a lysate on centrifugation or settling can be separated into layers, one of which is an aqueous:lipid layer. Other layers can include a solid pellet, an aqueous layer, and a lipid layer. Lipid can be extracted from the emulsion layer by freeze thawing or otherwise cooling the emulsion. In such methods, it is not necessary to add any organic solvent or oil. If any solvent or oil is added, it can be below 5% v/v or w/w of the lysate.

The extracted lipids are then subjected to an alkaline hydrolysis reaction as described above, in which the amount of base added to the reaction mixture can be tailored to saponify a desired amount of the glycerolipid and fatty acid ester constituents of the lipid composition. A close approximation or quantification of the amount of esterified lipid in the composition can be used to tailor the amount of base needed to saponify a specified portion of the oil, thereby providing an opportunity to modulate the amount of unsaponified oil remaining in the resulting composition. In some cases, at least 1%, at least 2%, at least 3%, at least 4%, at least 5%, at least 6%, at least 7%, at least 8%, at least 9%, or at least 10% of the oil, by weight, remains unsaponified in the resulting composition. In other cases, it may be desirable to saponify all or substantially all of the oil, such that the resulting composition contains no more than 10%, no more than 9%, no more than 8%, no more than 7%, no more than 6%, no more than 5%, no more than 4%, no more than 3%, no more than 2%, no more than 1%, or no more than 0.5% unsaponified oil by weight.

In various embodiments of the invention, the microbial biomass can contain lipids with varying carbon chain lengths, and with varying levels of saturation. The characteristics of the lipids can result from the natural glycerolipid profiles of the one or more microorganism populations used to generate the biomass subjected to the saponification reaction, or can be the result of lipid pathway engineering, as described herein, in which transgenic strains of microorganisms are designed to produce particular lipids in greater proportions.

D. Cosmetic Compositions of Microalgal Biomass and Algal Oil

In one aspect, the present invention is directed to cosmetic compositions comprising at least 1% w/w microalgal biomass and/or microalgal oil. In some embodiments, the cosmetic compositions comprise at least 2%, at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95% microalgal biomass and/or microalgal oil. The remainder of a cosmetic composition in accordance with the present invention comprises water or other conventional cosmetic ingredients, including those identified herein.

Cosmetic compositions of the present invention can be in the form of finished cosmetic products for use in skin care, bathing, and/or other applications pertaining to the maintenance or improvement of an individual's appearance or health. In other cases, the cosmetic compositions of the invention are in the form of cosmetic ingredients themselves, for use in combination with other cosmetic ingredients in the production of finished cosmetic products.

In some embodiments, cosmetic compositions of the present invention comprise at least 1% w/w microalgal biomass, or a greater percentage as described above. The microalgal biomass comprises at least 10% microalgal oil by dry weight, and can include greater amounts of microalgal oil as well as other constituents as described herein.

The microalgal biomass useful in the cosmetic compositions of the invention can be derived from one or more species of microalgae cultured and/or genetically engineered as described herein.

In various embodiments, cosmetic compositions comprising microalgal biomass can be formulated as decorative or care cosmetics with one or more other cosmetic ingredients. Exemplary cosmetic compositions include, without limitation, skin-care creams, lotions, powders, perfumes and deodorants, lipsticks, bath oils, bath scrubs and cleansing products, masks, and the like.

In some embodiments, cosmetic compositions of the present invention comprise at least 1% w/w microalgal oil, or a greater percentage as described above. The microalgal oil is derived from cultures of microalgae grown under heterotrophic conditions or those comprising at least 10% oil by dry cell weight, as described herein. In some cases, the microalgae can be genetically engineered.

In various embodiments, cosmetic compositions comprising microalgal oil can be formulated as decorative or care cosmetics with one or more other cosmetic ingredients. Exemplary cosmetic compositions include, without limitation, skin-care creams, lotions, beauty oils, perfumes and deodorants, lipsticks, bath oils, bath scrubs and cleansing products, masks, and the like.

E. Use in Conventional Finished Cosmetic Products

In some cases, microalgal cosmetic compositions in accordance with the present invention can be used in otherwise conventional finished cosmetic products. In these instances, the cosmetic composition comprising microalgal biomass and/or microalgal oil is combined with one or more other cosmetic ingredients, as described herein, to form a cosmetic composition that may be packaged as a finished cosmetic product. In some cases, microalgal cosmetic compositions of the present invention can be packaged as a cosmetic ingredient with optional instructions for combining the microalgal composition with conventional cosmetic ingredients to create finished cosmetic products.

In at least one embodiment, the present invention is directed to a method of preparing a finished cosmetic composition, e.g., a skin-care product, comprising (i) culturing a population of microalgae under conditions to generate microalgal biomass comprising at least 10% microalgal oil by dry weight, (ii) harvesting the biomass from the microalgal culture, (iii) performing one or more optional processing steps, e.g., drying the biomass or extracting oil from the biomass, (iv) combining the biomass or the extracted oil with at least one other cosmetic ingredient to form a cosmetic composition, and (v) packaging the cosmetic composition with optional instructions for its use as a finished cosmetic product.

In one aspect, the present invention is directed to a method of using a microalgal biomass composition to soften and impart pliability to skin. In one embodiment, the microalgal biomass composition comprises predominantly intact microalgal cells containing at least 10% microalgal oil by dry weight. Preferably, the algal oil present in the composition is predominantly encapsulated in cells of the biomass. The microalgal biomass composition is applied to human skin and retained in contact with the skin for a period of time sufficient to permit release of a specified percentage of the oil from the intact microalgal cells by enzymatic degradation of the cells. For example, the composition can be retained in contact with the skin for a period of time sufficient to release at least 50% of the microalgal oil from the predominantly intact cells. In some cases, this period may be from 3-4 hours.

Without intending to be bound by any particular theory, it is believed that enzymes present on human skin will slowly degrade the intact microalgal cells, thereby releasing the intracellular contents, including microalgal oil, over a period of time. In some embodiments, the microalgal biomass composition is retained in contact with the skin for at least 15 minutes, for at least 30 minutes, for at least 45 minutes, for at least 1 hour, for at least 2 hours, for at least 3 hours, or for at least 4 hours or more.

Microalgal biomass compositions useful in the above method can also comprise cells containing at least 25%, at least 35%, or at least 45% oil by dry weight. In other cases, the cells may contain other percentages of oil as described herein. In some cases, mixtures of microalgal cells having different glycerolipid profiles can be combined together to form the microalgal biomass composition.

All references cited herein, including patents, patent applications, and publications, are hereby incorporated by reference in their entireties, whether previously specifically incorporated or not. The publications mentioned herein are cited for the purpose of describing and disclosing reagents, methodologies and concepts that may be used in connection with the present invention. Nothing herein is to be construed as an admission that these references are prior art in relation to the inventions described herein. In particular, the following patent applications are hereby incorporated by reference in their entireties for all purposes: U.S. Provisional Application No. 61/074,610, filed Jun. 20, 2008, entitled "Soaps and Cosmetics Products Produced from Oil-Bearing Microbial Biomass and Oils"; U.S. Provisional Application No. 61/105,121, filed Oct. 14, 2008, entitled "Food Compositions of Microalgal Biomass"; PCT Patent Application No. PCT/US2008/065563, filed Jun. 2, 2008, entitled "Production of Oil in Microorganisms"; PCT Patent Application No. PCT/US2007/001653, filed Jan. 19, 2007, entitled "Microalgae-Derived Composition for Improving Health and Appearance of Skin"; and U.S. patent application Ser. No. 12/176,320, filed Jul. 18, 2008, entitled "Compositions for Improving the Health and Appearance of Skin".

Although this invention has been described in connection with specific embodiments thereof, it will be understood that it is capable of further modifications. This application is intended to cover any variations, uses, or adaptations of the invention following, in general, the principles of the invention and including such departures from the present disclosure as come within known or customary practice within the art to which the invention pertains and as may be applied to the essential features hereinbefore set forth.

V. Examples

The following examples are offered to illustrate, but not to limit, the claimed invention.

EXAMPLE 1

Cultivation of Microalgae to Achieve High Oil Content

Microalgae strains were cultivated to achieve a high percentage of oil by dry cell weight. Cryopreserved cells were thawed at room temperature and 500 ul of cells were added to 4.5 ml of medium (4.2 g/L $K_2HPO_4$, 3.1 g/L $NaH_2PO_4$, 0.24 g/L $MgSO_4 \cdot 7H_2O$, 0.25 g/L Citric Acid monohydrate, 0.025 g/L $CaCl_2$ $2H_2O$, 2 g/L yeast extract) plus 2% glucose and grown for 7 days at 28° C. with agitation (200 rpm) in a 6-well plate. Dry cell weights were determined by centrifuging 1 ml of culture at 14,000 rpm for 5 min in a pre-weighed Eppendorf tube. The culture supernatant was discarded and the resulting cell pellet washed with 1 ml of deionized water. The culture was again centrifuged, the supernatant discarded, and the cell pellets placed at −80° C. until frozen. Samples were then lyophyllized for 24 hrs and dry cell weights calculated. For determination of total lipid in cultures, 3 ml of culture was removed and subjected to analysis using an Ankom system (Ankom Inc., Macedon, N.Y.) according to the manufacturer's protocol. Samples were subjected to solvent extraction with an Amkom XT10 extractor according to the manufacturer's protocol. Total lipid was determined as the difference in mass between acid hydrolyzed dried samples and solvent extracted, dried samples. Percent oil dry cell weight measurements are shown in Table 1.

TABLE 1

Percent oil by dry cell weight.

| Species | Strain | % oil | Strain # |
|---|---|---|---|
| Chlorella kessleri | UTEX 397 | 39.42 | 4 |
| Chlorella kessleri | UTEX 2229 | 54.07 | 5 |
| Chlorella kessleri | UTEX 398 | 41.67 | 6 |
| Parachlorella kessleri | SAG 11.80 | 37.78 | 7 |
| Parachlorella kessleri | SAG 14.82 | 50.70 | 8 |
| Parachlorella kessleri | SAG 21.11 H9 | 37.92 | 9 |
| Prototheca stagnora | UTEX 327 | 13.14 | 10 |
| Prototheca moriformis | UTEX 1441 | 18.02 | 11 |
| Prototheca moriformis | UTEX 1435 | 27.17 | 12 |
| Chlorella minutissima | UTEX 2341 | 31.39 | 13 |
| Chlorella protothecoides | UTEX 250 | 34.24 | 1 |
| Chlorella protothecoides | UTEX 25 | 40.00 | 2 |
| Chlorella protothecoides | CCAP 211/8D | 47.56 | 3 |
| Chlorella sp. | UTEX 2068 | 45.32 | 14 |
| Chlorella sp. | CCAP 211/92 | 46.51 | 15 |
| Chlorella sorokiniana | SAG 211.40B | 46.67 | 16 |
| Parachlorella beijerinkii | SAG 2046 | 30.98 | 17 |
| Chlorella luteoviridis | SAG 2203 | 37.88 | 18 |
| Chlorella vulgaris | CCAP 211/11K | 35.85 | 19 |
| Chlorella reisiglii | CCAP 11/8 | 31.17 | 20 |
| Chlorella ellipsoidea | CCAP 211/42 | 32.93 | 21 |
| Chlorella saccharophila | CCAP 211/31 | 34.84 | 22 |
| Chlorella saccharophila | CCAP 211/32 | 30.51 | 23 |

EXAMPLE 2

Fermentation of Microalgae to Generate High Oil Content Biomass

Three fermentation processes were performed with three different media formulations with the goal of generating algal biomass with high oil content. The first formulation (Media 1) was based on medium described in Wu et al. (1994 *Science in China*, vol. 37, No. 3, pp. 326-335) and consisted of per liter: $KH_2PO_4$, 0.7 g; $K_2HPO_4$, 0.3 g; $MgSO_4$-$7H_2O$, 0.3 g; $FeSO_4$-$7H_2O$, 3 mg; thiamine hydrochloride, 10 μg; glucose, 20 g; glycine, 0.1 g; $H_3BO_3$, 2.9 mg; $MnCl_2$-$4H_2O$, 1.8 mg; $ZnSO_4$-$7H_2O$, 220 μg; $CuSO_4$-$5H_2O$, 80 μg; and $NaMoO_4$-$2H_2O$, 22.9 mg. The second medium (Media 2) was derived from the flask media described in Example 1 and consisted of per liter: $K_2HPO_4$, 4.2 g; $NaH_2PO_4$, 3.1 g; $MgSO_4$-$7H_2O$, 0.24 g; citric acid monohydrate, 0.25 g; calcium chloride dehydrate, 25 mg; glucose, 20 g; yeast extract, 2 g. The third medium (Media 3) was a hybrid and consisted of per liter: $K_2HPO_4$, 4.2 g; $NaH_2PO_4$, 3.1 g; $MgSO_4$-$7H_2O$, 0.24 g; citric acid monohydrate, 0.25 g; calcium chloride dehydrate, 25 mg; glucose, 20 g; yeast extract, 2 g; $H_3BO_3$, 2.9 mg; $MnCl_2$-$4H_2O$, 1.8 mg; $ZnSO_4$-$7H_2O$, 220 μg; $CuSO_4$-$5H_2O$, 80 μg; and $NaMoO_4$-$2H_2O$, 22.9 mg. All three media formulations were prepared and autoclave sterilized in lab scale fermentor vessels for 30 minutes at 121° C. Sterile glucose was added to each vessel following cool down post autoclave sterilization.

Inoculum for each fermentor was *Chlorella protothecoides* (UTEX 250), prepared in two flask stages using the medium and temperature conditions of the fermentor inoculated. Each fermentor was inoculated with 10% (v/v) mid-log culture. The three lab scale fermentors were held at 28° C. for the duration of the experiment. The microalgal cell growth in Media 1 was also evaluated at a temperature of 23° C. For all fermentor evaluations, pH was maintained at 6.6-6.8, agitations at 500 rpm, and airflow at 1 vvm. Fermentation cultures were cultivated for 11 days. Biomass accumulation was measured by optical density at 750 nm and dry cell weight.

Lipid/oil concentration was determined using direct transesterification with standard gas chromatography methods. Briefly, samples of fermentation broth with biomass was blotted onto blotting paper and transferred to centrifuge tubes and dried in a vacuum oven at 65-70° C. for 1 hour. When the samples were dried, 2 mL of 5% $H_2SO_4$ in methanol was added to the tubes. The tubes were then heated on a heat block at 65-70° C. for 3.5 hours, while being vortexed and sonicated intermittently. 2 ml of heptane was then added and the tubes were shaken vigorously. 2M1 of 6% $K_2CO_3$ was added and the tubes were shaken vigorously to mix and then centrifuged at 800 rpm for 2 minutes. The supernatant was then transferred to GC vials containing $Na_2SO_4$ drying agent and ran using standard gas chromatography methods. Percent oil/lipid was based on a dry cell weight basis. The dry cell weights for cells grown using: Media 1 at 23° C. was 9.4 g/L; Media 1 at 28° C. was 1.0 g/L, Media 2 at 28° C. was 21.2 g/L; and Media 3 at 28° C. was 21.5 g/L. The lipid/oil concentration for cells grown using: Media 1 at 23° C. was 3 g/L; Media 1 at 28° C. was 0.4 g/L; Media 2 at 28° C. was 18 g/L; and Media 3 at 28° C. was 19 g/L. The percent oil based on dry cell weight for cells grown using: Media 1 at 23° C. was 32%; Media 1 at 28° C. was 40%; Media 2 at 28° C. was 85%; and Media 3 at 28° C. was 88%. The lipid profiles (in area %, after normalizing to the internal standard) for algal biomass generated using the three different media formulations at 28° C. are summarized below in Table 2.

TABLE 2

Lipid profiles for *Chlorella protothecoides* grown under different media conditions.

| | Media 1 28° C. (in Area %) | Media 2 28° C. (in Area %) | Media 3 28° C. (in Area %) |
|---|---|---|---|
| C14:0 | 1.40 | 0.85 | 0.72 |
| C16:0 | 8.71 | 7.75 | 7.43 |
| C16:1 | — | 0.18 | 0.17 |
| C17:0 | — | 0.16 | 0.15 |
| C17:1 | — | 0.15 | 0.15 |
| C18:0 | 3.77 | 3.66 | 4.25 |
| C18:1 | 73.39 | 72.72 | 73.83 |
| C18:2 | 11.23 | 12.82 | 11.41 |
| C18:3 alpha | 1.50 | 0.90 | 1.02 |
| C20:0 | — | 0.33 | 0.37 |
| C20:1 | — | 0.10 | 0.39 |
| C20:1 | — | 0.25 | — |
| C22:0 | — | 0.13 | 0.11 |

EXAMPLE 3

Culture of *Chlorella protothecoides* to Generate High Oil Algal Flakes

*Chlorella protothecoides* (UTEX 250) biomass was produced using 5,000 L fermentation tanks using processes described in Example 2. Glucose (corn syrup) concentration was between was monitored throughout the run. When the glucose concentration was low, more glucose was added to the fermentation tank. After all nitrogen was consumed, the cells began accumulating lipid. Samples of biomass were taken throughout the run to monitor lipid levels and the run was stopped when the biomass reached the desired lipid content (over 40% lipid by dry cell weight). In this case, the biomass was harvested when it reached approximately 50% lipid by dry cell weight.

To process the microaglal biomass into algal flakes, the harvested *Chlorella protothecoides* biomass was separated from the culture medium using centrifugation and dried on a drum dryer using standard methods at approximately 150-170° C. The resulting drum-dried *Chlorella protothecoides* biomass with approximately 50% lipid by dry cell weight (high lipid) was packaged and stored for use as algal flakes.

EXAMPLE 4

Production of Algal Powder (High Lipid)

High lipid containing *Chlorella protothecoides* grown using the fermentation methods and conditions described in Example 3 was processed into a high lipid algal powder. To process the microaglal biomass into algal powder, the harvested *Chlorella protothecoides* biomass was separated from the culture medium and then concentrated using centrifugation and dried using a spray dryer according to standard methods. The resulting algal powder (whole algal cells that have been spray dried into a powder form) was packaged and stored until use.

EXAMPLE 5

Production of Algal Flour (High Lipid)

High lipid containing *Chlorella protothecoides* grown using the fermentation methods and conditions described in Example 3 was processed into a high lipid algal flour. To process the microaglal biomass into algal flour, the harvested *Chlorella protothecoides* biomass was separated from the culture medium using centrifugation. The resulting concentrated biomass, containing over 40% moisture, was micronized using a high pressure homogenizer ((GEA model NS1001) operating at a pressure level of 1000-1200 Bar until the average particle size of the biomass was less than 10 µm. The algal homogenate was then spray dried using standard methods. The resulting algal flour (micronized algal cell that have been spray dried into a powder form) was packaged and stored until use.

EXAMPLE 6

Chemical Mutagenesis to Generate Algal Color Mutants

*Chlorella protothecoides* (UTEX 250) was grown according to the methods and conditions described in Example 1. Chemical mutagenesis was performed on the algal strain using N-methyl-N'-nitro-N-nitroguanidine (NTG). The algal culture was subjected to the mutagen (NTG) and then selected through rounds of reisolation on 2.0% glucose agar plates. The colonies were screened for color mutants. *Chlorella protothecoides* (wildtype) appears to be a golden color when grown heterotophically. The screen produced one strain that appeared white in color on the agar plate. This color mutant was named 33-55 (deposited on Oct. 13, 2009 in accordance with the Budapest Treaty at the American Type Culture Collection at 10801 University Boulevard, Manassas, Va. 20110-2209 with a Patent Deposit Designation of PTA-XXXX). Another colony was also isolated and went through three rounds of reisolation to confirm that this mutation was stable. This mutant appeared to be light yellow in color on the agar plate and was named 25-32 (deposited on Oct. 13, 2009 in accordance with the Budapest Treaty at the American Type Culture Collection at 10801 University Boulevard, Manassas, Va. 20110-2209 with a Patent Deposit Designation of PTA-XXXX).

Lipid Profile of *Chlorella protothecoides* 33-55

*Chlorella protothecoides* 33-55 and the parental *Chlorella protothecoides* (UTEX 250) were grown according to the methods and conditions described in Example 1. The percent lipid (by dry cell weight) was determined for both strains: *Chlorella protothecoides* 33-55 was at 68% lipid and the parental strain was at 62% lipid. The lipid profiles were determined for both strains and were as follows (expressed as area %): *Chlorella protothecoides* 33-55, C14:0 (0.81); C16:0 (10.35); C16:1 (0.20); C18:0 (4.09); C18:1 (72.16); C18:2 (10.60); C18:3 (0.10); and others (1.69); for the parental strain, C14:0 (0.77); C16:0 (9.67); C16:1 (0.22); C18:0 (4.73); C18:1 (71.45); C18:2 (10.99); C18:3 (0.14); and others (2.05).

EXAMPLE 7

Preparation of Biomass

Microalgal biomass is generated by culturing microalgae as described herein. The microalgal biomass is then harvested from the culture bioreactor, and washed with water to remove residual salts and culture media. The microalgal biomass is then optionally subjected to a cell disruption procedure to generate a lysate and/or optionally dried to form a microalgal biomass composition.

GMP procedures are followed. Any person who, by medical examination or supervisory observation, is shown to have, or appears to have, an illness, open lesion, including boils, sores, or infected wounds, or any other abnormal source of microbial contamination by which there is a reasonable possibility of the microalgal biomass, biomass-contact surfaces, or biomass-packaging materials becoming contaminated, is to be excluded from any operations which may be expected to result in such contamination until the condition is corrected. Personnel are instructed to report such health conditions to their supervisors. All persons working in direct contact with the microalgal biomass, biomass-contact surfaces, and biomass-packaging materials conform to hygienic practices while on duty to the extent necessary to protect against contamination of the microalgal biomass. The methods for maintaining cleanliness include, but are not limited to: (1) Wearing outer garments suitable to the operation in a manner that protects against the contamination of biomass, biomass-contact surfaces, or biomass packaging materials; (2) Maintaining adequate personal cleanliness; (3) Washing hands thoroughly (and sanitizing if necessary to protect against contamination with undesirable microorganisms) in an adequate hand-washing facility before starting work, after each absence from the work station, and at any other time when the hands may have become soiled or contaminated; (4) Removing all unsecured jewelry and other objects that might fall into biomass, equipment, or containers, and removing hand jewelry that cannot be adequately sanitized during periods in which biomass is manipulated by hand. If such hand jewelry cannot be removed, it may be covered by material which can be maintained in an intact, clean, and sanitary condition and which effectively protects against the contamination by these objects of the biomass, biomass-contact surfaces, or biomass-packaging materials; (5) Maintaining gloves, if they are used in biomass handling, in an intact, clean, and sanitary condition. The gloves should be of an impermeable material; (6) Wearing, where appropriate, in an effective manner, hair nets, headbands, caps, beard covers, or other effective hair restraints; (7) Storing clothing or other personal belongings in areas other than where biomass is exposed or where equipment or utensils are washed; (8) Confining the following to areas other than where biomass may be exposed or where equipment or utensils are washed: eating biomass, chewing gum, drinking beverages, or using tobacco; and (9) Taking any other necessary precautions to protect against contamination of biomass, biomass-contact surfaces, or biomass-packaging materials with microorganisms or foreign substances including, but not limited to, perspiration, hair, cosmetics, tobacco, chemicals, and medicines applied to the skin. The microalgal biomass can optionally be subjected to a cell disruption procedure to generate a lysate and/or optionally dried to form a microalgal biomass composition.

EXAMPLE 8

Solvent Extraction of Oil from Biomass

Algal oil is extracted from microalgal biomass prepared as described in Example 1 by physically disrupting the biomass and contacting the disrupted biomass with an organic solvent, e.g., hexane, for a period of time sufficient to allow the oil to form a solution with the hexane. The solution is then filtered and the hexane removed by roto-evaporation to recover the extracted oil.

EXAMPLE 9

Solventless Extraction of Oil from Biomass

In an alternative to the solvent extraction procedure described in Example 8, algal oil is extracted from microalgal biomass prepared as described in Example 7 following lysis of the cells by applying physical pressure to the biomass in a press. The oil thus separated from the cellular material is then recovered.

EXAMPLE 10

Diversity of Lipid Chains in Algal Species

Lipid samples from a subset of strains grown in Example 1 were analyzed for lipid profile using standard HPLC techniques. The results expressed as a percentage of total lipids and are summarized below in Table 3.

TABLE 3

Diversity of lipid chains in algal species.

| Strain | C:14:0 | C:16:0 | C:16:1 | C:18:0 | C:18:1 | C:18:2 | C:18:3 | C:20:0 | C:20:1 |
|---|---|---|---|---|---|---|---|---|---|
| *Chlorella prototheocoides* (UTEX 250) | 0.57 | 10.30 | 0 | 3.77 | 70.52 | 14.24 | 1.45 | 0.27 | 0 |
| *Chlorella prototheocoides* (UTEX 25) | 0.61 | 8.70 | 0.30 | 2.42 | 71.98 | 14.21 | 1.15 | 0.20 | 0.24 |
| *Chlorella kessleri* (UTEX 397) | 0.68 | 9.82 | 0 | 2.83 | 65.78 | 12.94 | 1.46 | 0 | 0 |
| *Chlorella kessleri* (UTEX 2229) | 1.47 | 21.96 | 0 | 4.35 | 22.64 | 9.58 | 5.2 | 3.88 | 3.3 |
| *Prototheca stagnora* (UTEX 327) | 0 | 12.01 | 0 | 0 | 50.33 | 17.14 | 0 | 0 | 0 |
| *Prototheca moriformis* (UTEX 1441) | 1.41 | 29.44 | 0.70 | 3.05 | 57.72 | 12.37 | 0.97 | 0.33 | 0 |
| *Prototheca moriformis* (UTEX 1435) | 1.09 | 25.77 | 25.77 | 2.75 | 54.01 | 11.90 | 2.44 | 0 | 0 |

EXAMPLE 11

Carotenoid, Phospholipid, Tocotrienol and Tocopherol Composition of *Chlorella protothecoides* UTEX 250 Biomass A sample of algal biomass produced using methods described in Example 7 was analyzed for tocotrienol and tocopherol content using normal phase HPLC, AOCS Method Ce 8-89. The tocotrienol and tocopherol-containing fraction of the biomass was extracted using hexane or another non-polar solvent. The complete tocotrienol and tocopherol composition results are summarized in Table 4.

TABLE 4

Tocotrienol and tocopherol content in algal biomass.
Tocotrienol and tocopherol composition of *Chlorella protothecoides* UTEX 250

| Tocopherols | |
| --- | --- |
| Alpha tocopherol | 6.29 mg/100 g |
| Delta tocopherol | 0.47 mg/100 g |
| Gamma tocopherol | 0.54 mg/100 g |
| Total tocopherols | 7.3 mg/100 g |
| Tocotrienols | |
| Alpha tocotrienol | 0.13 mg/g |
| Beta tocotrienol | 0 |
| Gamma tocotrienol | 0.09 mg/g |
| Delta tocotrienol | 0 |
| Total tocotrienols | 0.22 mg/g |

The carotenoid-containing fraction of the biomass was isolated and analyzed fpr carotenoids using HPLC methods. The carotenoid-containing fraction was prepared by mixing lyophilized algal biomass (produced using methods described in Example 8) with silicon carbide in an aluminum mortar and ground four times for 1 minute each time, with a mortar and pestle. The ground biomass and silicon mixture was then rinsed with tetrahydrofuran (THF) and the supernatant was collected. Extraction of the biomass was repeated until the supernatant was colorless and the THF supernatant from all of the extractions were pooled and analyzed for carotenoid content using standard HPLC methods. The carotenoid content for algal biomass that was dried using a drum dryer was also analyzed using the methods described above.

The carotenoid content of freeze dried algal biomass was: total lutein (66.9-68.9 mcg/g: with cis-lutein ranging from 12.4-12.7 mcg/g and trans-lutein ranging from 54.5-56.2 mcg/g); trans-zeaxanthin (31.427-33.451 mcg/g); cis-zeaxanthin (1.201-1.315 mcg/g); t-alpha cryptoxanthin (3.092-3.773 mcg/g); t-beta cryptoxanthin (1.061-1.354 mcg/g); 15-cis-beta carotene (0.625-0.0675 mcg/g); 13-cis-beta carotene (0.0269-0.0376 mcg/g); t-alpha carotene (0.269-0.0376 mcg/g); c-alpha carotene (0.043-0.010 mcg/g); t-beta carotene (0.664-0.741 mcg/g); and 9-cis-beta carotene (0.241-0.263 mcg/g). The total reported carotenoids ranged from 105.819 mcg/g to 110.815 mcg/g.

The carotenoid content of the drum-dried algal biomass was significantly lower: total lutein (0.709 mcg/g: with trans-lutein being 0.091 mcg/g and cis-lutein being 0.618 mcg/g); trans-zeaxanthin (0.252 mcg/g); cis-zeaxanthin (0.037 mcg/g); alpha-cryptoxanthin (0.010 mcg/g); beta-cryptoxanthin (0.010 mcg/g) and t-beta-carotene (0.008 mcg/g). The total reported carotenoids were 1.03 mcg/g.

These data suggest that the method used for drying the algal biomass can significantly affect the carotenoid content.

Phospholipid analysis was also performed on the algal biomasss. The phospholipid containing fraction was extracted using the Folch extraction method (chloroform, methanol and water mixture) and the oil sample was analyzed using AOCS Official Method Ja 7b-91, HPLC determination of hydrolysed lecithins (International Lecithin and Phopholipid Society 1999), and HPLC analysis of phospholipids with light scatting detection (International Lecithin and Phospholipid Society 1995) methods for phospholipid content. The total phospholipids by percent w/w was 1.18%. The phospholipid profile of algal oil was phosphatidylcholine (62.7%), phosphatidylethanolamine (24.5%), lysophosphatidiylcholine (1.7%) and phosphatidylinositol (11%). Similar analysis using hexane extraction of the phospholipid-containing fraction from the algal biomass was also performed. The total phospholipids by percent w/w was 0.5%. The phospholipid profile was phosphatidylethanolamine (44%), phosphatidylcholine (42%) and phosphatidylinositol (14%).

EXAMPLE 12

Saponification of Microalgal Biomass

Biomass having a high-oil content (at least ~15% oil by dry weight) is generated by the methods described herein. The biomass comprises dried whole algal cells containing lipid globules encapsulated in partially dehydrated cell mass.

Preparation of a Liquid Cellular Soap: The biomass is dispersed in water to form an oil-in-cell emulsion concentrate. An excess of KOH sufficient to convert the desired amount of glycerolipids and fatty acid esters to fatty acid salts is then dissolved in the aqueous solution comprising the biomass. The mixture is then stirred to facilitate completion of the alkaline hydrolysis reaction, and heated to a temperature between 80-90° C. for from 30 minutes to 12 hours to complete the conversion of lipids to fatty acid salts. Water lost to evaporation is replaced as necessary throughout the reaction process. Additives are combined with the saponified composition, including glycerin (for clarity and to impart a moisturizing characteristic), ethylenediamine ((EDTA) as a chelating agent to enhance performance when used in hard water conditions), cocoamidopropyl betaine (an amphoteric surfactant used to impart cleansing and rinsing properties), and a fragrance to produce a soap product. In some embodiments, the soap product comprises a cellular soap with components as shown in Table 5 below. An example of whole microalgae cells used in a soap composition is show in the FIGURE.

TABLE 5

Components of cellular soap made directly from biomass.

| Component | Quantity |
| --- | --- |
| Biomass (Whole Cells) | 10-60% |
| KOH | 1-5% |
| Glycerin | 5-25% |
| Fragrance | 1-2% |
| EDTA | 1-5% |
| Water | to 100% |

The cellular soaps described in this example include natural hydrating and skin softening characteristics imparted by the presence of carbohydrates and proteins from the algal cells, as well as antioxidant properties derived from the incorporation of algal carotenoids, tocotrienols, tocopherls, and other compounds into the composition.

Alternatively, an organic base such as triethanolamine is used in the alkaline hydrolysis reaction to produce a clearer product. The use of triethanolamine or another organic base produces a milder product, less likely to cause irritation to skin.

Optionally, the fatty acid salts are precipitated from the mixture by addition of NaCl or KCl salts, and separated for use in compositions in combination with various additives as described herein.

EXAMPLE 13

Saponification of Hexane-Extracted Oil from Microalgal Biomass

Biomass is generated according to the methods described herein. Conventional hexane extraction of the lipids from the biomass is performed. The hexane extracted lipids are then saponified by mixing the lipids with an aqueous solution of NaOH or KOH containing an amount of base sufficient to convert the desired amount of lipid to fatty acid salts, and optionally heating the mixture to expedite the reaction. The fatty acid salts are then precipitated by addition of NaCl or KCl. Compositions of saponified oils derived from hexane-extracted biomass contain higher proportions of contaminating carotenoids than solventless-extracted oils due to the efficiency with which hexane extracts such compounds from the microbial biomass.

EXAMPLE 14

Saponification of Solventless-Extracted Oil from Microalgal Biomass

Biomass is generated according to the methods described herein. A solventless extraction of the lipids from the biomass is performed by lysis and pressing of the biomass through the use of physical pressure, or alternatively through methods such as those described in U.S. Pat. No. 6,750,048. The extracted lipids are saponified by mixing the lipids with an aqueous solution of NaOH or KOH containing an amount of base sufficient to convert the desired amount of lipid to fatty acid salts, and optionally heating the mixture to expedite the reaction. The fatty acid salts are then precipitated by addition of NaCl or KCl. Compositions of saponified oils derived from hexane-extracted biomass contain relatively lower proportions of contaminating carotenoids, as compared to solventless-extracted lipids, due to the decreased efficiency with which such compounds are extracted from the microbial biomass using the solventless procedure.

EXAMPLE 15

Algal Soap

Biomass is generated and prepared according to the methods described herein. Algal oil is extracted from the biomass by conventional hexane extraction, or by a solventless extraction procedure. The algal oil is combined with other cosmetic ingredients, as shown in Tables 6 and 7, as described below, to form a liquid or solid algal soap.

Liquid Formula: Lauric acid and sucrose cocoate are heated to form a melted mixture to which potassium hydroxide and algal oil are added to form an algal soup mix. Water is heated to 90° C. and the algal soup mix is added to the water to form a solution. Lauryl glucoside, cocoamidopropyl betaine, coco hydrolyzed soy protein, arginine and salicylic acid are then added to the solution, which is mixed until the solution is clear. The clear solution is then allowed to cool and the fragrance/flavor is added. The liquid algal soap is then bottled.

TABLE 6

Components of liquid algal soap.

| Component | Quantity |
|---|---|
| Lauryl Glucoside | 25% |
| Cocoamidopropyl Betaine | 10% |
| Coco Hydrolyzed Soy Protein | 5% |
| Lauric Acid | 2% |
| Algal Oil | 1% |
| Sucrose Cocoate | 5% |
| Potassium Hydroxide | 0.5% |
| Arginine | 0.5% |
| Salicylic Acid | 0.5% |
| Fragrance/Flavor | 0.5% |
| Water | to 100% |

Solid Formula: Soap noodles (potassium cocoate and potassium stearate) are added to a soap plodder. Algal oil and fragrance are added to the plodder and mixed with the noodles. Soap is extruded and die cut into bars of a desired shape.

TABLE 7

Components of solid algal soap.

| Component | Quantity |
|---|---|
| Soap Noodles (potassium cocoate and potassium stearate) | 94.5% |
| Algal Oil | 5% |
| Fragrance | 0.5% |

EXAMPLE 16

Algal Clay Mask

Biomass is generated and prepared according to the methods described herein, preferably containing at least 15% oil dry cell weight. Algal oil is extracted from the biomass by conventional hexane extraction, or by a solventless extraction procedure. Biomass comprising predominantly intact whole algal cells is used in the whole cell formulation. The biomass or algal oil is combined with other cosmetic ingredients, as shown in Tables 10 and 11, as described below, to form algal oil or whole cell algal clay masks.

Algal Oil Formulation: Gums (acacia, cellulose and PVP) are dispersed in a mixture of water and aloe juice along with propylene glycol. EDTA is added to the dispersion, and the dispersion is heated to 70° C. In a separate container, the oils (glyceryl stearate, lecithin, vitamin E, and algal oil) are heated to 70° C. The heated oils are added to the dispersion containing the gums and mixed to form an emulsion. Bentonite is added to the emulsion as it cools, and with continued mixing the allantoin, benzyl alcohol, capryl glycol and phenoxyethanol are added to the mixture to form the algal oil clay mask.

TABLE 8

Components of algal oil clay mask.

| Component | Quantity |
| --- | --- |
| Bentonite | 5-20% |
| Glyceryl Stearate SE | 1-10% |
| Algae Oil | 1-20% |
| Propylene Glycol | 1-10% |
| Lecithin | 1-5% |
| Cellulose Gum | 0.1-1% |
| *Acacia* Senegal Gum | 0.1-1% |
| Polyvinylpyrrolidone (PVP) | 0.1-1% |
| Vitamin E | 0.1-1% |
| Allantoin | 0.1-1% |
| *Aloe Barbadensis* Leaf Juice | 1-50% |
| Ethylenediaminetetraacetic acid (EDTA) | 0.1-0.5% |
| Phenoxyethanol | 0.1-1% |
| Capryl Glycol | 0.1-2% |
| Benzyl Alcohol | 0.1-1% |
| Water | to 100% |

Whole Cell Formulation: Gums (acacia, cellulose and PVP) are dispersed in a mixture of the water and aloe juice along with the propylene glycol. EDTA is added to the dispersion, and the dispersion is heated to 70° C. In a separate container, the oils (glyceryl stearate, lecithin, and vitamin E) are heated to 70° C. The heated oils are added to the dispersion containing the gums and mixed to form an emulsion. Bentonite and whole algae cells are added to the emulsion as it cools, and with continued mixing the allantoin, benzyl alcohol, capryl glycol and phenoxyethanol are added to the mixture to form the whole cell algal clay mask.

TABLE 9

Components of whole cell algal clay mask.

| Component | Quantity |
| --- | --- |
| Bentonite | 5-20% |
| Glyceryl Stearate SE | 1-10% |
| Whole Algae Cells | 1-20% |
| Propylene Glycol | 1-10% |
| Lecithin | 1-5% |
| Cellulose Gum | 0.1-1% |
| *Acacia* Senegal Gum | 0.1-1% |
| Polyvinylpyrrolidone (PVP) | 0.1-1% |
| Vitamin E | 0.1-1% |
| Allantoin | 0.1-1% |
| *Aloe Barbadensis* Leaf Juice | 1-50% |
| Ethylenediaminetetraacetic acid (EDTA) | 0.1-0.5% |
| Phenoxyethanol | 0.1-1% |
| Capryl Glycol | 0.1-2% |
| Benzyl Alcohol | 0.1-1% |
| Water | to 100% |

EXAMPLE 17

Beauty Biomass Emulsion/Beauty Serum

Biomass comprising cells having at least 50% oil by dry weight is generated and prepared according to the methods described herein including a drying step. The biomass is combined with other cosmetic ingredients, as shown in Table 10, as described below, to form the beauty biomass emulsion.

Xanthum gum is dispersed in water heated to 50° C., and upon dissolution the B vitamins, salicylic acid, lysine, arginine, and superoxide dismutase are added. The composition is mixed until clear. Into this composition is dispersed the algae cells and the composition is mixed to form a homogenous dispersion. Fragrance is added and the dispersion is bottled.

TABLE 10

Components of beauty biomass emulsion.

| Component | Quantity |
| --- | --- |
| Whole Dried Algae Cells | 30% |
| Xanthum Gum | 0.3% |
| Vitamin B1 | 0.1% |
| Vitamin B2 | 0.1% |
| Vitamin B3 | 0.1% |
| Vitamin B5 | 0.1% |
| Vitamin B6 | 0.1% |
| Salicylic Acid | 0.5% |
| Lysine | 0.1% |
| Arginine | 0.5% |
| Superoxide Dismutase | 0.1% |
| Fragrance | 0.2% |
| Water | to 100% |

Whole Cell Beauty Serum: A whole cell dispersion is made using 15% high oil (approx. 49% lipid DCW) Algal Flour in 85% deionized water and a high pressure homogenizer (Niro). The other ingredients, shown in Table 11 below, were combined with the whole cell dispersion and homogenized until smooth.

TABLE 11

Components of whole cell beauty serum.

| Component | Quantity |
| --- | --- |
| Whole Cell Dispersion (15% Algal Flour in deionized water) | 50% |
| Xanthan Gum | 0.03% |
| Vitamin B3 | 0.1% |
| Vitamin B5 | 0.1% |
| Phenoxyethanol & Capryl glycol & Chlorphenesin (Mikrokill CO5) | 0.5% |
| Deionized Water | 49% |

EXAMPLE 18

Algal Beauty Oil

Biomass is generated and prepared according to the methods described herein. Algal oil is extracted from the biomass by conventional hexane extraction or by a solventless extraction procedure. The algal oil is combined with other cosmetic ingredients, as shown in Table 12, as described below, to form the algal beauty oil.

Approximately 20% of the algal oil is heated to 120° C. and the hydrogenated lecithin, cholesterol, and the sterols are dissolved therein. The remaining algal oil is blended with the vitamins and coenzyme Q10 until a clear composition is formed. The heated oil solution is added to the blended oil composition and stirred. Fragrance is added, and the composition is cooled and bottled.

TABLE 12

Components of algal beauty oil.

| Component | Quantity |
| --- | --- |
| Algal Oil | 98.0% |
| Vitamin E | 0.5% |
| Vitamin A | 0.1% |
| Vitamin D | 0.2% |
| Coenzyme Q10 | 0.1% |
| Phytosterol/Phycosterol | 0.5% |
| Hydrogenated Lecithin | 0.3% |

TABLE 12-continued

Components of algal beauty oil.

| Component   | Quantity |
|-------------|----------|
| Cholesterol | 0.1%     |
| Fragrance   | 0.2%     |

EXAMPLE 19

Oil/Salt Scrub

Biomass comprising cells having at least 20% oil by dry weight is generated and prepared according to the methods described herein. Algal oil is extracted from the biomass by conventional hexane extraction, or by a solventless extraction procedure. The algal oil is combined with other cosmetic ingredients, as shown in Table 13, as described below, to form the oil/salt scrub.

Hydrogenated lecithin, sucrose cocoate and hydrogenated castor oil are dissolved in the algal oil by heating the mixture to 110° C. The solution is then cooled to 45° C. and the salt crystals are stirred in. Fragrance is added and the composition is cooled and bottled.

TABLE 13

Components of algal oil/salt scrub.

| Component              | Quantity |
|------------------------|----------|
| Algal Oil              | 60%      |
| Salt Crystals          | 30%      |
| Sucrose Cocoate        | 5%       |
| Hydrogenated Lecithin  | 2%       |
| Hydrogenated Castor Oil| 2%       |
| Fragrance              | 1%       |

EXAMPLE 20

Marine Infusion Algal Beauty Oil

Biomass is generated and prepared according to the methods described herein. Algal oil is extracted from the biomass by methods described herein. The algal oil is combined with other cosmetic ingredients, as shown in Table 14, as described below, to form the marine infusion algal beauty oil.

Squalane is mixed with the algal oil. The mixture is heated to 60° C., and the algal carotenoids (xeaxanthin, asthaxanthin, pytoene, phytofluene) and phycosterols are dissolved in the mixture. The solution is cooled to 40° C. and the algal DHA oil, vitamin E and fragrance are added. The composition is stirred, cooled and bottled.

TABLE 14

Components of marine infusion algal beauty oil.

| Component          | Quantity |
|--------------------|----------|
| Algal Oil          | 57%      |
| Algal Xeaxanthin   | 0.1%     |
| Algal Phytoene     | 0.1%     |
| Algal Phytofluene  | 0.1%     |
| Algal Asthaxanthin | 0.1%     |
| Phycosterols       | 0.1%     |
| Vitamin E          | 1%       |

TABLE 14-continued

Components of marine infusion algal beauty oil.

| Component                     | Quantity |
|-------------------------------|----------|
| Squalene                      | 40%      |
| docosahexanoic acid (DHA) oil | 1%       |
| Fragrance                     | 0.5%     |

EXAMPLE 21

Algal Whole Cell Shampoo and Conditioner

Biomass is generated and prepared according to the methods described herein.

Whole Cell Shampoo: A whole cell dispersion (1% algal solids, made using algal flakes containing approx. 50% lipid DCW) was made first using a Niro homogenizer on the lowest setting as not to break the cell walls of the algal biomass, and set aside for later combination with the ingredients shown in Table 15, below. Water was combined with the glycerin and warmed (so that the glycerin will go into solution) and the Polyquaternium 11 was added into the warmed glycerin/water solution. The guar gum was added and mixed followed by the Surfapon AG-20, Mackam 2C and Foamsoy C. The solution was warmed to between 60-70° C. and the Optiphen was added. The Monadmin CMA and Cerasynt IP was melted together and added to the hot shampoo mixture. The algal dispersion was added and the remaining water was added. The shampoo was cooled and bottled.

TABLE 15

Components of algal whole cell shampoo.

| Component                                            | Quantity (by weight) |
|------------------------------------------------------|----------------------|
| Deionized Water                                      | 20.67%               |
| Glycerin                                             | 9.96%                |
| Surfapon AG-20                                       | 39.84%               |
| Foam Soy C                                           | 2.99%                |
| Mackam 2C                                            | 9.96%                |
| Keltrol T                                            | 0.6%                 |
| Guar Gum                                             | 0.6%                 |
| Whole Cell Algal Dispersion (algal flakes at 1% solids) | 3%                |
| Polyquaternium 11                                    | 0.2%                 |
| Cerasynt IP                                          | 0.7%                 |
| Monamid CMA                                          | 2%                   |
| Optiphen                                             | 0.5%                 |
| Deionized Water                                      | 8.9%                 |
| Fragrance                                            | 0.6%                 |

Whole Cell Conditioner: A whole cell dispersion (1.5% algal solids, algal flakes containing approx. 50% lipid DCW) was made first using a Niro homogenizer on the lowest setting as not to break the cell walls of the algal biomass. The remaining ingredients shown in Table 16, below, were combined with the whole cell dispersion until smooth. A sample of the finished conditioner was kept at room temperature for over 6 months and the product is stable and does not separate.

TABLE 16

Components of algal whole cell conditioner.

| Description | % By Weight | Ingredient's Role In Formulation |
|---|---|---|
| Whole Cell Dispersion (1.5% algal cells in deionized water) | 5.00% | Naturally increases softness Nutritive and conditioning Increased bio-moisturization All natural and sustainably grown Natural protectant/nourisher of the scalp |
| Water | 81.20% | Aqua-based system |
| Cetyl Alcohol | 6.00% | Emollient and Emulsifying ingredient |
| Stearyl Alcohol | 0.50% | Emollient and Emulsifying ingredient |
| Glycerin | 3.00% | Moisturizer |
| Isopropanol | 1.70% | |
| Parfum | 0.50% | |
| Polyquaternium 11 | 0.10% | Thickening and styling agent |
| Parfum | 0.40% | |
| Nicotineic Acid | 0.05% | Styling agent |
| *Aloe Barbadensis* Leaf Juice | 0.10% | Soothing and moisturizing ingredient |
| Pantothenic Acid/Yeast Polypeptide | 0.05% | Bio-Moisturizer |
| Sucrose | 1.00% | Softening and styling agent |
| Fragrance | 0.40% | Emulsifier |
| Citric Acid | Q.S | |

EXAMPLE 22

Absence of Algal Toxins in Dried *Chlorella protothecoides* Biomass

A sample of dried *Chlorella protothecoides* (UTEX 250) biomass was analyzed using liquid chromatography-mass spectrometry/mass spectrometry (LC-MS/MS) analysis for the presence of contaminating algal and cyanobacterial toxins. The analyses covered all groups of algal and cyanobacterial toxins published in the literature and mentioned in international food regulations. The analyses were directed to exclude very low concentrations of a certain toxin using both LC-MS/MS methods and bioassays. The results show that the biomass sample did not contain any detectable levels of any of the aglal or cyanobacterial toxins that were tested. The results are summarized below in Table 17.

TABLE 17

LC-MS/MS analytical results for algal and cyanobacterial toxins.

| Toxin Category | Toxin | Result | Limit of detection (LC/MS) |
|---|---|---|---|
| Amnesic Shellfish Poisoning (ASP) Toxins | Domoic Acid | Not detectable | 1 µg/g |
| Diarrhetic Shellfish Poisoning (DSP) Toxins | Okadaic acid and Dinophysistoxins | Not detectable | 0.1 µg/g |
| | Pectenotoxins | Not detectable | 0.1 µg/g |
| | Yessotoxins | Not detectable | 0.1 µg/g |
| | Azaspiracides | Not detectable | 0.1 µg/g |
| | Gymnodimines | Not detectable | 0.1 µg/g |
| Paralytic Shellfish Poisoning (PSP) Toxins | Saxitoxin | Not detectable | (HPLC/FD) 0.3 µg/g |
| | Neosaxitoxin | Not detectable | (HPLC/FD) 0.3 µg/g |
| | Decarbamoylsaxitoxin | Not detectable | (HPLC/FD)) 0.3 µg/g |
| | Gonyautoxins | Not detectable | (HPLC/FD) 0.3 µg/g |
| Neurotoxic Shellfish Poisoning (NSP) Toxins | Brevetoxins | Not detectable | 0.1 µg/g |
| Cyanobacterial toxins | Microsystins MC-RR, MC-LR, MC-YR, MC-LA, MC-LW and MC-LF | Not detectable | 0.1 µg/g |
| | Nodularin | Not detectable | 0.1 µg/g |
| | Anatoxin-a | Not detectable | 0.5 µg/g |
| | Cylindrospermopsins | Not detectable | 0.2 µg/g |
| | Beta-Methylamino-L-Alanine | Not detectable | 2.5 µg/g |

EXAMPLE 23

Genotyping of Microalgae

Genomic DNA was isolated from algal biomass as follows. Cells (approximately 200 mg) were centifuged from liquid cultures 5 minutes at 14,000×g. Cells were then resuspended in sterile distilled water, centrifuged 5 minutes at 14,000×g and the supernatant discarded. A single glass bead ~2 mm in diameter was added to the biomass and tubes were placed at −80° C. for at least 15 minutes. Samples were removed and 150 µl of grinding buffer (1% Sarkosyl, 0.25 M Sucrose, 50 mM NaCl, 20 mM EDTA, 100 mM Tris-HCl, pH 8.0, RNase A 0.5 ug/ul) was added. Pellets were resuspended by vortexing briefly, followed by the addition of 40 ul of 5M NaCl. Samples were vortexed briefly, followed by the addition of 66 µl of 5% CTAB (Cetyl trimethylammonium bromide) and a final brief vortex. Samples were next incubated at 65° C. for 10 minutes after which they were centrifuged at 14,000×g for 10 minutes. The supernatant was transferred to a fresh tube and extracted once with 300 µl of Phenol:Chloroform:Isoamyl alcohol 12:12:1, followed by centrifugation for 5 minutes at 14,000×g. The resulting aqueous phase was transferred to a fresh tube containing 0.7 vol of isopropanol (~190 µl), mixed by inversion and incubated at room temperature for 30 minutes or overnight at 4° C. DNA was recovered via centrifugation at 14,000×g for 10 minutes. The resulting pellet was then washed twice with 70% ethanol, followed by a final wash with 100% ethanol. Pellets were air dried for 20-30 minutes at room temperature followed by resuspension in 50 µl of 10 mM TrisCl, 1 mM EDTA (pH 8.0).

Five µl of total algal DNA, prepared as described above, was diluted 1:50 in 10 mM Tris, pH 8.0. PCR reactions, final volume 20 µl, were set up as follows. Ten µl of 2×iProof HF master mix (BIO-RAD) was added to 0.4 µl primer SZ02613 (5'-TGTTGAAGAATGAGCCGGCGAC-3' (SEQ ID NO:24) at 10 mM stock concentration). This primer sequence runs from position 567-588 in Gen Bank accession no. L43357 and is highly conserved in higher plants and algal plastid genomes. This was followed by the addition of 0.4 µl primer SZ02615 (5'-CAGTGAGCTATTACG-CACTC-3' (SEQ ID NO:25) at 10 mM stock concentration). This primer sequence is complementary to position 1112-1093 in Gen Bank accession no. L43357 and is highly conserved in higher plants and algal plastid genomes. Next, 5 µl of diluted total DNA and 3.2 µl dH$_2$O were added. PCR reactions were run as follows: 98° C., 45"; 98° C., 8"; 53° C., 12"; 72° C., 20" for 35 cycles followed by 72° C. for 1 min and holding at 25° C. For purification of PCR products, 20 µl of 10 mM Tris, pH 8.0, was added to each reaction, followed by extraction with 40 µl of Phenol:Chloroform: isoamyl alcohol 12:12:1, vortexing and centrifuging at 14,000×g for 5 minutes. PCR reactions were applied to S-400 columns (GE Healthcare) and centrifuged for 2 minutes at 3,000×g. Purified PCR products were subsequently TOPO cloned into PCR8/GW/TOPO and positive clones selected for on LB/Spec plates. Purified plasmid DNA was sequenced in both directions using M13 forward and reverse primers. Sequences from strains 1-23 (designated in Example 1, Table 1) are listed as SEQ ID NOs:1-23 in the attached Sequence Listing.

EXAMPLE 24

Genotyping Analysis of Commercially Purchased *Chlorella* Samples

Three commercially purchased *Chlorella* samples, *Chlorella regularis* (New Chapter, 390 mg/gelcap), Whole Foods Broken Cell Wall *Chlorella* (Whole Foods, 500 mg/pressed tablet) and NutriBiotic CGF *Chlorella* (NutriBiotic, 500 mg/pressed tablet), were genotyped using the methods described in Example 22. Approximately 200 mg of each commercially purchased *Chlorella* samples were resuspended and sterile distilled water for genomic DNA isolation.

The resulting PCR products were isolated and cloned into vectors and sequenced using M13 forward and reverse primers. The sequences were compared to known sequences using a BLAST search.

Comparison of 23s rRNA DNA sequences revealed that two out of the three commercially purchased *Chlorella* samples had DNA sequences matching *Lyngbya aestuarii* present (Whole Foods Broken Wall *Chlorella* and NutriBiotic CGF). *Lyngbya aestuarii* is a marine-species cynobacteria. These results show that some commercially available *Chlorella* contain other species of contaminating microorganisms, including organisms from genera such as *Lyngbya* that are known to produce toxins (see for example Teneva et. al, Environmental Toxicology, 18(1)1, pp. 9-20 (2003); Matthew et al., J Nat Prod., 71(6): pp. 1113-6 (2008); and Carmichael et al., Appl Environ Microbiol, 63(8): pp. 3104-3110 (1997).

EXAMPLE 25

Oil Content Analysis of Commercially Purchased *Chlorella* Samples

The three commercially purchased *Chlorella* samples described above were analyzed for total lipid content (% w/w) and total fatty acid content using gas chromatography analysis (GC/FID). Results were confirmed using mass spectrometry. Results are summarized below in Table 18. The difference between total lipid content and total fatty acid content is likely due to phospholipids, pigments and sterols, which would be included in the total lipid content, but not in the total fatty acid content. A detailed analysis of the individual fatty acid content of each sample is summarized in Table 19 below.

TABLE 18

Oil content of commercially purchased *Chlorella* samples.

| Manufacturer | Total Lipid Content (%) | Total Fatty Acid Content (%) |
|---|---|---|
| Whole Foods | 8.8 | 6.2 |
| New Chapter | 5.0 | 3.8 |
| Nutribiotic | 14.0 | 9.4 |

TABLE 19

Fatty acid content of commercially purchased *Chlorella* samples.

| Manufacturer | C14:0 | C16:0 | C16:1 | C18:0 | C18:1 | C18:2 |
|---|---|---|---|---|---|---|
| Whole Foods | 0.41% | 28.77% | 1.10% | 7.16% | 47.53% | 15.03% |
| New Chapter | 3.58% | 45.84% | 0.00% | 14.03% | 30.05% | 6.49% |
| Nutribiotic | 0.00% | 33.14% | 0.00% | 12.46% | 36.78% | 17.63% |

What is claimed is:

1. A topical cosmetic composition comprising microalgal biomass of heterotrophically cultivated *Chlorella protothecoides* and at least one other cosmetic ingredient, wherein the microalgal biomass (i) is not green in color, (ii) comprises less than 5% DHA and at least 10% microalgal oil by dry weight, and (iii) further comprises phytosterols, tocopherols, tocotrienols, or xanthophylls.

2. The topical cosmetic composition of claim 1, wherein the biomass comprises at least 5 mg of tocopherols per 100 grams of biomass.

3. The topical cosmetic composition of claim 1, wherein the biomass comprises at least 0.1 mg of tocotrienols per gram of biomass.

4. The topical cosmetic composition of claim 1, wherein the biomass comprises predominantly intact or lysed cells.

5. The cosmetic composition of claim 1, wherein the at least one other cosmetic ingredient is an ingredient selected from the group consisting of an absorbent, abrasive, anticaking agent, antifoaming agent, soluble polysaccharide, insoluble polysaccharide, partially soluble polysaccharide, microalgal polysaccharide, antimicrobial agent, binder, biological additive, buffering agent, bulking agent, chemical additive, cosmetic biocide, denaturant, cosmetic astringent, drug astringent, external analgesic, film former, humectant, opacifying agents, fragrance, flavor oil, pigment, coloring, essential oil, skin sensate, emollients, skin soothing agent, skin healing agent, pH adjuster, plasticizer, preservative, preservative enhancer, propellant, reducing agent, skin-conditioning agent, skin penetration enhancing agent, skin protectant, solvent, suspending agent, emulsifier, thickening agent, solubilizing agent, soap, sunscreen, sunblock, ultraviolet light absorber, ultraviolet light scattering agent, sunless tanning agent, antioxidant, radical scavenger, chelating agent, sequestrant, anti-acne agent, anti-inflammatory agent, anti-androgen, depilation agent, desquamation agent, exfoliant, organic hydroxy acid, vitamin, vitamin derivative, and natural plant extract.

6. A topical cosmetic composition comprising microalgal oil isolated from microalgal biomass of heterotrophically cultivated *Chlorella protothecoides*, the cosmetic composition comprising at least one other cosmetic ingredient, wherein the microalgal biomass (i) is not green in color, (ii) comprises less than 5% DHA and at least 10% microalgal oil by dry weight, and (iii) further comprises phytosterols, tocopherols, tocotrienols, or xanthophylls.

7. The topical cosmetic composition of claim 6, wherein the biomass comprises at least 5 mg of tocopherols per 100 grams of biomass.

8. The topical cosmetic composition of claim 6, wherein the biomass comprises at least 0.1 mg of tocotrienols per gram of biomass.

9. The cosmetic composition of claim 7, wherein the at least one other cosmetic ingredient is an ingredient selected from the group consisting of an absorbent, abrasive, anticaking agent, antifoaming agent, soluble polysaccharide, insoluble polysaccharide, partially soluble polysaccharide, microalgal polysaccharide, antimicrobial agent, binder, biological additive, buffering agent, bulking agent, chemical additive, cosmetic biocide, denaturant, cosmetic astringent, drug astringent, external analgesic, film former, humectant, opacifying agents, fragrance, flavor oil, pigment, coloring, essential oil, skin sensate, emollients, skin soothing agent, skin healing agent, pH adjuster, plasticizer, preservative, preservative enhancer, propellant, reducing agent, skin-conditioning agent, skin penetration enhancing agent, skin protectant, solvent, suspending agent, emulsifier, thickening agent, solubilizing agent, soap, sunscreen, sunblock, ultraviolet light absorber, ultraviolet light scattering agent, sunless tanning agent, antioxidant, radical scavenger, chelating agent, sequestrant, anti-acne agent, anti-inflammatory agent, anti-androgen, depilation agent, desquamation agent, exfoliant, organic hydroxy acid, vitamin, vitamin derivative, and natural plant extract.

10. A method of making a topical cosmetic composition comprising combining microalgal biomass with at least one other cosmetic ingredient, wherein the microalgal biomass (i) is not green in color, (ii) comprises less than 5% DHA and at least 10% microalgal oil by dry weight, and (iii) further comprises phytosterols, tocopherols, tocotrienols, or xanthophylls.

11. The method of claim 10, wherein the biomass comprises at least 5 mg of tocopherols per 100 grams of biomass.

12. The method of claim 10, wherein the biomass comprises at least 0.1 mg of tocotrienols per gram of biomass.

13. The method of claim 10, wherein the biomass comprises predominantly intact or lysed cells.

14. The method of claim 10, wherein the at least one other cosmetic ingredient is an ingredient selected from the group consisting of an absorbent, abrasive, anticaking agent, antifoaming agent, soluble polysaccharide, insoluble polysaccharide, partially soluble polysaccharide, microalgal polysaccharide, antimicrobial agent, binder, biological additive, buffering agent, bulking agent, chemical additive, cosmetic biocide, denaturant, cosmetic astringent, drug astringent, external analgesic, film former, humectant, opacifying agents, fragrance, flavor oil, pigment, coloring, essential oil, skin sensate, emollients, skin soothing agent, skin healing agent, pH adjuster, plasticizer, preservative, preservative enhancer, propellant, reducing agent, skin-conditioning agent, skin penetration enhancing agent, skin protectant, solvent, suspending agent, emulsifier, thickening agent, solubilizing agent, soap, sunscreen, sunblock, ultraviolet light absorber, ultraviolet light scattering agent, sunless tanning agent, antioxidant, radical scavenger, chelating agent, sequestrant, anti-acne agent, anti-inflammatory agent, anti-androgen, depilation agent, desquamation agent, exfoliant, organic hydroxy acid, vitamin, vitamin derivative, and natural plant extract.

15. A method of making a topical cosmetic composition comprising combining microalgal oil isolated from microalgal biomass of heterotrophically cultivated *Chlorella prototheocoides* with at least one other cosmetic ingredient, wherein the microalgal biomass (i) is not green in color, (ii) comprises less than 5% DHA and at least 10% microalgal oil by dry weight, and (iii) further comprises phytosterols, tocopherols, tocotrienols, or xanthophylls.

16. The method of claim 15, wherein the biomass comprises at least 5 mg of tocopherols per 100 grams of biomass.

17. The method of claim 15, wherein the biomass comprises at least 0.1 mg of tocotrienols per gram of biomass.

18. The method of claim 15, wherein the at least one other cosmetic ingredient is an ingredient selected from the group consisting of an absorbent, abrasive, anticaking agent, antifoaming agent, soluble polysaccharide, insoluble polysaccharide, partially soluble polysaccharide, microalgal polysaccharide, antimicrobial agent, binder, biological additive, buffering agent, bulking agent, chemical additive, cosmetic biocide, denaturant, cosmetic astringent, drug astringent, external analgesic, film former, humectant, opacifying agents, fragrance, flavor oil, pigment, coloring, essential oil, skin sensate, emollients, skin soothing agent, skin healing agent, pH adjuster, plasticizer, preservative, preservative enhancer, propellant, reducing agent, skin-conditioning agent, skin penetration enhancing agent, skin protectant, solvent, suspending agent, emulsifier, thickening agent, solubilizing agent, soap, sunscreen, sunblock, ultraviolet light absorber, ultraviolet light scattering agent, sunless tanning agent, antioxidant, radical scavenger, chelating agent, sequestrant, anti-acne agent, anti-inflammatory agent, anti-androgen, depilation agent, desquamation agent, exfoliant, organic hydroxy acid, vitamin, vitamin derivative, and natural plant extract.

\* \* \* \* \*